US009102960B2

(12) United States Patent
Botes et al.

(10) Patent No.: US 9,102,960 B2
(45) Date of Patent: *Aug. 11, 2015

(54) METHODS OF PRODUCING 6-CARBON CHEMICALS VIA COA-DEPENDENT CARBON CHAIN ELONGATION ASSOCIATED WITH CARBON STORAGE

(71) Applicant: INVISTA North America S.á r.l., Wilmington, DE (US)

(72) Inventors: Adriana Leonora Botes, Rosedale East (GB); Alex Van Eck Conradie, Eaglescliffe (GB)

(73) Assignee: INVISTA North America S.á.r.l., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/106,124

(22) Filed: Dec. 13, 2013

(65) Prior Publication Data
US 2014/0186902 A1 Jul. 3, 2014

Related U.S. Application Data

(63) Continuation-in-part of application No. 13/715,981, filed on Dec. 14, 2012.

(60) Provisional application No. 61/576,401, filed on Dec. 16, 2011.

(51) Int. Cl.
| C12P 7/18 | (2006.01) |
| C12P 7/44 | (2006.01) |
| C12P 7/42 | (2006.01) |
| C12P 17/10 | (2006.01) |
| C12P 13/00 | (2006.01) |
| C12N 15/52 | (2006.01) |

(52) U.S. Cl.
CPC ............... C12P 13/001 (2013.01); C12N 15/52 (2013.01); C12P 7/18 (2013.01); C12P 7/42 (2013.01); C12P 7/44 (2013.01); C12P 13/005 (2013.01); C12P 17/10 (2013.01)

(58) Field of Classification Search
None
See application file for complete search history.

(56) References Cited

U.S. PATENT DOCUMENTS

| 2,439,513 A | 4/1948 | Hamblet et al. |
| 2,557,282 A | 6/1951 | Hamblet et al. |
| 2,791,566 A | 5/1957 | Jeffers |
| 2,840,607 A | 6/1958 | Attane, Jr. et al. |
| 2,971,010 A | 2/1961 | Gilby, Jr. et al. |
| 3,023,238 A | 2/1962 | Chapman et al. |
| 3,338,959 A | 8/1967 | Sciance et al. |
| 3,365,490 A | 1/1968 | Arthur et al. |
| 3,515,751 A | 6/1970 | Oberster |
| 3,719,561 A | 3/1973 | Tanaka et al. |
| 4,058,555 A | 11/1977 | Mims |
| 6,255,451 B1 | 7/2001 | Koch et al. |
| 6,372,939 B1 | 4/2002 | Bunnel et al. |
| 8,088,607 B2 | 1/2012 | Buggard et al. |
| 2004/0054235 A1 | 3/2004 | Fodor et al. |
| 2010/0035309 A1 | 2/2010 | Havemen et al. |
| 2010/0151536 A1 | 6/2010 | Baynes et al. |
| 2010/0203600 A1 | 8/2010 | Dubois |
| 2010/0317069 A1 | 12/2010 | Burk et al. |
| 2011/0171699 A1 | 7/2011 | Raemakers-Franken et al. |
| 2011/0256599 A1 | 10/2011 | Hu et al. |
| 2012/0064252 A1 | 3/2012 | Beatty |
| 2012/0101009 A1 | 4/2012 | Beatty |
| 2013/0065279 A1 | 3/2013 | Burk et al. |
| 2013/0183728 A1 | 7/2013 | Botes et al. |
| 2013/0210090 A1 | 8/2013 | Pearlman et al. |
| 2013/0217081 A1 | 8/2013 | Pearlman et al. |
| 2013/0224807 A1 | 8/2013 | Pearlman et al. |
| 2014/0186904 A1 | 7/2014 | Botes et al. |
| 2014/0193861 A1 | 7/2014 | Botes et al. |
| 2014/0193862 A1 | 7/2014 | Botes et al. |
| 2014/0193863 A1 | 7/2014 | Botes et al. |
| 2014/0193864 A1 | 7/2014 | Botes et al. |
| 2014/0193865 A1 | 7/2014 | Botes et al. |
| 2014/0196904 A1 | 7/2014 | Fontenelle et al. |
| 2014/0199737 A1 | 7/2014 | Botes et al. |
| 2014/0248673 A1 | 9/2014 | Botes et al. |

FOREIGN PATENT DOCUMENTS

| WO | WO 2008/006037 | 1/2008 |
| WO | WO 2008/145737 | 12/2008 |
| WO | WO 2009/113855 | 9/2009 |
| WO | WO 2009/140695 | 11/2009 |
| WO | WO 2009/140696 | 11/2009 |
| WO | WO 2009/151728 | 12/2009 |
| WO | WO 2010/068944 | 6/2010 |
| WO | WO 2010/068953 | 6/2010 |
| WO | WO 2010/071759 | 6/2010 |
| WO | WO 2010/104390 | 9/2010 |

(Continued)

OTHER PUBLICATIONS

"Enterococcus faecalis V583 bifuntional acetaldehyde-CoA/Alcohol Dehydrogenase," biocyc.org, retrieved on Jun. 19, 2014, http://biocyc.org/EFAE226185/N EW-IMAGE?type=ENZYME &object=GH11-877-MONOMER, 9 pages.

(Continued)

Primary Examiner — Suzanne M Noakes
(74) Attorney, Agent, or Firm — Fish & Richardson P.C.

(57) ABSTRACT

This document describes biochemical pathways for producing adipic acid, caprolactam, 6-aminohexanoic acid, 6-hydroxyhexanoic acid, hexamethylenediamine or 1,6-hexanediol by forming two terminal functional groups, comprised of carboxyl, amine or hydroxyl groups, in a C6 aliphatic backbone substrate. These pathways, metabolic engineering and cultivation strategies described herein rely on CoA-dependent elongation enzymes or analogs enzymes associated with the carbon storage pathways from polyhydroxyalkanoate accumulating bacteria.

26 Claims, 28 Drawing Sheets

(56) References Cited

FOREIGN PATENT DOCUMENTS

| | | |
|---|---|---|
| WO | WO 2010/104391 | 9/2010 |
| WO | WO 2010/129936 | 11/2010 |
| WO | WO 2010/132845 | 11/2010 |
| WO | WO 2011/003034 | 1/2011 |
| WO | WO 2011/031146 | 3/2011 |
| WO | WO 2011/031147 | 3/2011 |
| WO | WO 2012/031910 | 3/2012 |
| WO | WO 2012/071439 | 5/2012 |
| WO | WO 2012/094425 | 7/2012 |
| WO | WO 2012/174430 | 12/2012 |
| WO | WO 2012/177721 | 12/2012 |
| WO | WO 2013/003744 | 1/2013 |
| WO | WO 2013/082542 | 6/2013 |
| WO | WO 2013/090837 | 6/2013 |
| WO | WO 2013/096898 | 6/2013 |
| WO | WO 2014/105788 | 7/2014 |

OTHER PUBLICATIONS

"Information on EC 1.2.1.57—butanal dehydrogenase," brenda-enzymes.org, retrieved on Jun. 19, 2014, http://www.brenda-enzymes.org/php/result_flat.php4?ecno=1.2.1.57, 6 pages.

"BRENDA—The comprehensive Enzyme Information System," Jul. 2011, retrieved on Aug. 19, 2014, http://web.archive.org/web/20111009205602/http://www.brenda-enzymes.org/, 1 page.

Alber et al., "Malonyl-coenzyme A reductase in the modified 3-hydroxypropionate cycle for autotrophic carbon fixation in archaeal *Metallosphaera* and *Sulfolobus* spp.," J. Bacteriology, 2006, 188:8551-8559.

Anton et al., Polyamides, Fibers, Encyclopedia of Polymer Science and Engineering, 2001, 11:409-445.

Azuma et al., "Naphthalene—a constituent of Magnolia flowers," Phytochemistry, 1996, 42:999-1004.

Barker et al., "Enzymatic reactions in the degradation of 5-aminovalerate by *Clostridium aminovalercum*," J Biol Chem., 1987, 262(19):8994- 9003.

Becker et al., "Metabolic flux engineering of L-lysine production in *Corynebacterium glutamicum*—over expression and modification of G6P dehydrogenase," J Biotechnol. 2007, 132(2):99-109.

Bellmann et al., "Expression control and specificity of the basic amino acid exporter LysE of *Corynebacterium glutamicum*," Microbiology 2001, 147:1765-1774.

Bennett et al., "Purification and properties of ε-caprolactone hydrolases from *Acinetobacter* NCIB 9871 and *Nocardia globevula* CL1," Journal of General Microbiology, 1988 134: 161-168.

Bernstein et al., "Transfer of the high-GC cyclohexane caboxylate degradation pathway from *Rhodopseudomonas palustris* to *Escherichia coli* for production of biotin," Metabolic Engineering, May 2008, 10(3-4):131-140.

Berthold et al., "Structure of the branched-chain keto acid decarboxylase (KdcA) from *Lactococcus lactis* provides insights into the structural basis for the chemoselective and enantioselective carboligation reaction," Acta Crystallographica Sec. D, 2007, D63:1217-1224.

Binieda et al., "Purification, characterization, DNA Sequence and cloning of a pimeloyl-CoA synthetase from *Pseudomonas medocin* 35," Biochem J., 1999, 340:793-801.

Bond-Watts et al., "Biochemical and Structural Characterization of the trans-Enoly-CoA Reductase from *Treponema denticola*," Biochemistry, 2012, 51:6827-6837.

Bordes et al., "Isolation of a thermostable variant of Lip2 lipase from *Yarrowia lipolytica* by directed evolution and deeper insight into the denaturation mechanisms," Journal of Biotechnology, 2011, 156: 117-124.

Botting, "Substrate Specificity of the 3-Methylaspartate Ammonia-Lyase Reaction: Observation of Differential Relative Reaction Rates for Substrate-Product Pairs," Biochemistry, 1988, 27:2953-2955.

Boylan et al., "Functional identification of the fatty acid reductase components encoded in the luminescence operon of *Vibrio fischeri*," Journal of Bacteriology, 1985, 163(3):1186-1190.

Boylan et al., "Lux C, D and E genes of the *Vibrio fischeri* luminescence operon code for the reductase, transferase, and synthetase enzymes involved in aldehyde biosynthsis," Photochemistry and photobiology, 1989, 49:681-688.

Bramer et al., "The methylcitric acid pathway in *Ralstonia eutropha*: new genes identified involved in propionate metabolism," Microbiology 2001, 147:2203-2214.

Breithaupt et al., "Crystal structure of 12-oxophytodienoate reductase 3 from tomato: self-inhibition by dimerization," Proc Natl. Acad Sci. USA, 2006, 103:14337-14342.

Brigham et al., "Engineering *Ralstonia eutropha* for Production of Isobutanol from CO2, H2, and 02," Advanced Biofuels and Bioproducts 2013, Chapter 39, pp. 1065-1090.

Brzostowicz et al., "mRNA differential display in a microbial enrichment culture: simultaneous identification of three cyclohexanonemonooxygenases from three species," Applied and Environmental Microbiology, 2003, 69: 334-342.

Brzostowicz et al., "Identification of two gene clusters involved in cyclohexanone oxidation in *Brevibacterium epidermidis* strain HCU," Applied and Microbiological Biotechnology, 2002, 58:781-789.

Buckel et al., "Glutaconate CoA-transferase from *Acidaminococcus fermentans*," Eur J. Biochem, 1981, 118:315-321.

Budde et al., "Roles of Multiple Acetoacetyl Coenzyme A Reductases in Polyhydroxybutyrate Biosynthesis in *Ralstonis eutropha* H16," J Bacteriol. 2010, 192(20):5319-5328.

Bugg et al., "The emerging role for bacteria in lignin degradation and bio-product formation," Curr Opin Biotechnol 2011, 22(3):394-400.

Buhler et al., "Occurrence and the possible physiological role of 2-enoate reductases," FEBS Letters, 1980, 109:244-246.

Bult et al., "Complete genome sequence of the methanogenicarchaeon, *Methanococcus jannaschii*," Science, 1996, 273: 1058-1073.

Bunik et al., "Kinetic properties of the 2-oxoglutarate dehydrogenase complex from *Azotobacter vinelandii* evidence for the formation of a precatalytic complex with 2-oxoglutarate," Eur J Biochem., 267(12):3583-3591, Jun. 2000.

Cantu et al., "Thioesterases: A new perspective based on their primary and tertiary structures," Protein Science 2010, 19:1281-1295.

Chayabutra and Ju, "Degradation of n-hexadecane and its metabolites by *Pseudomonas aeruginosa* under microaerobic and anaerobic denitrifying conditions," Appl Environ Microbiol., 66(2):493-498, Feb. 2000.

Cheesbrough and Kolattukudy, "Alkane biosynthesis by decarbonylation of aldehydes catalyzed by a particulate preparation from *Pisum sativum*," PNAS USA, 1984, 81(21):6613-7.

Chen et al., "*Termites fumigate* their nests with naphthalene," Nature, 1998, 392:558-559.

Cheng et al., "Genetic Analysis of a Gene Cluster for Cyclohexanol Oxidation in *Acinetobacter* sp. Strain SE19 by In Vitro Transposition," Journal of Bacteriology, 2000, 182(17):4744-4751.

Coon, "Omega oxygenases: nonheme-iron enzymes and P450 cytochromes," Biochemical & Biophysical Research Communications, 2005,338:378-385.

Cronan and Lin, "Synthesis of the α,ω-dicarboxylic acid precursor of biotin by the canonical fatty acid biosynthetic pathway," Current Opinion in Chem Biol., 2011, 15:407-413.

Cryle and Schlichting, "Structural insights from a P450 Carrier Protein complex reveal how specificity is achieved in the P450BioI Acp complex," Proceedings of the National Academy of Sciences, Oct. 2008, 105(41):15696-15701.

Cryle et al., "Carbon-carbon bond cleavage by cytochrome P450BioI (CYP107H1) E1," Chemical Communications, Jan. 2004, 86-87.

Cryle, "Selectivity in a barren landscape: the P450BioI-ACP complex," Biochemical Society Transactions, Aug. 2010, 38(4):934-939.

Da Silva et al., "Glycerol: A promising and abundant carbon source for industrial microbiology," Biotechnology Advances, 2009, 27:30-39.

Daisy et al., "Naphthalene, an insect repellent, is produced by *Muscodor vitigenus*, a novel endophytic fungus," Microbiology, 2002, 148:3737-3741.

Dalby, "Optimizing enzyme function by directed evolution," Current Opinion in Structural Biology, 2003, 13, 500-505.

(56) References Cited

OTHER PUBLICATIONS

Davis et al., "Overproduction of acetyl-CoA carboxylase activity increases the rate of fatty acid biosynthesis in *Escherichia coli*," J. Biol. Chem., 2000, 275(37): 28593-28598.
Day et al., "Partial purification and properties of acyl-CoA reductase from *Clostridum butyricum*," Archives of Biochemistry and Biophysics, 1978, 190(1):322-331.
Deana et al., "Substrate specificity of a dicarboxyl-CoA: Dicarboxylic acid coenzyme A transferase from rat liver mitochondria," Biochem Int., 1992, 26:767-773.
Dekishima et al., "Extending Carbon Chain Length of 1-Butanol Pathway for 1-Hexanol Synthesis from Glucose by Engineered *Escherichia coli*," J. Am. Chem. Soc., Aug. 2011, 133(30):11399-11401.
Dellomonaco et al., "Engineered reversal of the [beta]-oxidation cycle for the synthesis of fuels and chemicals," Nature, Jan. 2011, 476(7360):355-359.
Deshmukh and Mungre, "Purification and properties of 2-aminoadipate: 2-oxoglutarate aminotransferase from bovine kidney," Biochem J, 1989, 261(3):761-768.
Doan et al., "Functional expression of five *Arabidopsis* fatty acyl-CoA reductase genes in *Escherichia coli*," J. Plant Physiology, 2009, 166:787-796.
Dobritzsch et al., "High resolution crystal structure of pyruvate decarboxylase from *Zymomonas mobilis*. Implications for substrate activation in pyruvate decarboxylases," J. Biol. Chem., 1998, 273:20196-20204.
Donoghue and Trudgill, "The Metabolism of Cyclohexanol by Acinetobacter NCIB9871," Eur J Bochem., 1975, 60:1-7.
Drevland et al., "Enzymology and Evolution of the Pyruvate Pathway to 2-Oxobutyrate in *Methanocaldococcus jannaschii*," J. Bacteriol., Apr. 2007, 189(12):4391-4400.
Drevland et al., "Methanogen homoaconitase catalyzes both hydrolyase reactions in coenzyme B biosynthesis," J Biol Chem., Oct. 2008, 283: 28888-28896.
Egmond et al., "*Fusarium solani* pisi cutinase," Biochimie, Nov. 2000, 82(11):1015-1021.
Elkins et al., "Substrate Specificity of the RND-Type Multidrug Efflux Pumps AcrB and AcrD of *Esherichia coli* Is Determined Predominately by Two Large Periplasmic Loops," J Bacteriol. 2002, 184(23):6490-6499.
Elshahed et al., "Benzoate Fermentation by the Anaerobic bacterium *Syntrophus aciditrophicus* in the Absence of Hydrogen-Using Microorganisms," Applied and Environ Microbiology, 2001, 67(12):5520-5525.
Elshahed et al., "Metabolism of Benzoate, Cyclohex-l-ene Carboxylate, and Cyclohexane Carboxylate by *Syntrophus aciditrophicus* Strain SB in Syntrophic Association with H2-Using Microorganisms," Applied and Environ. Microbiol., Apr. 2001, 67(4):1728-1738.
Eurich et al., "Cloning and characterization of three fatty alcohol oxidase genes from *Candida tropicalis* strain ATCC 20336," Applied & Environmental Microbiology, 2004, 70(8): 4872-4879.
Ferreira et al. "A member of the sugar transporter family, Stl1p is the glycerol/H= symporter in *Saccharomyces cerevisiae*," Molecular Biology of the Cell, American Society for Cell Biology, Apr. 1, 2005, 16(4):2068-2076.
Fickers et al., "Carbon and nitrogen sources modulate lipase production in the yeast *Yarrowia lipolytica*," Journal of Applied Microbiology , 2004, 96:742-9.
Fickers et al., "The lipases from *Yarrowia lipolytica*: Genetics, production, regulation, biochemical characterization and biotechnological applications," Biotechnology Advances, 2011, 29: 632-644.
Fuchs et al., "Microbial degradation of aromatic compounds—from one strategy to four," Nat Rev Microbiol., Oct. 3, 2011;9(11):803-816, Oct. 2011.
Fukui et al., "Expression and Characterization of ®-Specific Enoly Coenzyme A Hydratase Involved in Polyhydroxyalkanoate Biosynthesis by *Aeromonas caviae*," J Bacteriol. 1998, 180(3):667-673.

Funhoff et al., "CYP153A6, a Soluble P450 Oxygenase Catalyzing Terminal-Alkane Hydroxylation," J Bacteriol. 2006, 188(14):5220-5227.
Funhoff et al., "Expression and Characterization of (R)-Specific Enoyl Coenzyme A Hydratase Involved in Polyhydroxyalkanoate Biosynthesis by *Aeromonas caviae*," J. Bacteriol., 2006, 188(14):5220-5227.
Gallus and Schink, "Anaerobic degradation of pimelate by newly isolated denitrifying bacteria," Microbiology, 1994, 140:409-416.
Gasmi et al., "A molecular approach to optimize hIFN α2b expression and secretion in *Yarrowia lipolytica*," Appl Microbiol Biotechnol, 2011, 89:109-119.
GenBank Accession No. AAA24664.1, Mar. 25, 1993, 1 page.
GenBank Accession No. AAA24665.1, Apr. 26, 1993, 1 page.
GenBank Accession No. AAA57874.1, Nov. 21, 2011, 2 pages.
GenBank Accession No. AAA69178.1, Jul. 1, 1995, 1 page.
GenBank Accession No. AAB35106, Nov. 1995, 1 page.
GenBank Accession No. AAB60068.1, dated Jul. 1995, 1 page.
GenBank Accession No. AAB98494.1, Oct. 23, 2009, 2 pages.
GenBank Accession No. AAB99007.1, Oct 23, 2009, 2 pages.
GenBank Accession No. AAB99277.1, Oct. 23, 2009.
GenBank Accession No. AAC23921, Apr. 23, 2003, 2 pages.
GenBank Accession No. AAC76437.1, dated Oct. 2010, 2 pages.
GenBank Accession No. AAF02538.1, Oct. 20, 1999, 2 pages.
GenBank Accession No. AAG08191.1, Jan. 31, 2014, 2 pages.
GenBank Accession No. AAK73167.2, retrieved May 19, 2014, 1 page.
GenBank Accession No. AAN37290.1, retrieved May 19, 2014, 1 page.
GenBank Accession No. AAO77182, Mar. 28, 2003, 1 page.
GenBank Accession No. AAQ59697.1, Jan. 31, 2014, 2 pages.
GenBank Accession No. AAS11092.1, Mar. 5, 2010, 1 page.
GenBank Accession No. AAS43086.1, dated Nov. 2011, 1 page.
GenBank Accession No. AAT43726, retrieved May 19, 2014, 1 page.
GenBank Accession No. AAW66853.1, Feb. 12, 2005, 1 page.
GenBank Accession No. AAY39893.1, Jan. 31, 2014, 2 pages.
GenBank Accession No. AB005294, Feb. 2000, 2 pages.
GenBank Accession No. ABA81135.1, Jan. 28, 2014, 2 pages.
GenBank Accession No. ABC76100.1, Mar. 11, 2010, 1 page.
GenBank Accession No. ABC76101.1, Mar. 11, 2010, 1 page.
GenBank Accession No. ABC76114.1, Mar. 11, 2010, 1 page.
GenBank Accession No. ABC76260.1, Mar. 11, 2010, 1 page.
GenBank Accession No. ABC76948.1, Mar. 11, 2010, 1 page.
GenBank Accession No. ABC76949.1, Mar. 11, 2010, 1 page.
GenBank Accession No. ABC77793.1, Mar. 11, 2010, 1 page.
GenBank Accession No. ABC77794.1, Mar. 11, 2010, 1 page.
GenBank Accession No. ABC77898.1, Mar. 11, 2010, 1 page.
GenBank Accession No. ABC77899.1, Mar. 11, 2010, 1 page.
GenBank Accession No. ABC77900.1, Mar. 11, 2010, 1 page.
GenBank Accession No. ABC78517.1, Mar. 11, 2010, 1 page.
GenBank Accession No. ABC78756.1, Mar. 11, 2010, 1 page.
GenBank Accession No. ABC78863.1, Mar. 11, 2010, 1 page.
GenBank Accession No. ABC78881.1, Mar. 11, 2010, 1 page.
GenBank Accession No. ABC78950.1, Mar. 11, 2010, 1 page.
GenBank Accession No. ABE47158.1, Jan. 26, 2014, 1 page.
GenBank Accession No. ABE47159.1, Jan. 28, 2014, 2 pages.
GenBank Accession No. ABE47160.1, Jan. 28, 2014, 1 page.
GenBank Accession No. ABI83656.1, Jan. 3, 2007, 1 page.
GenBank Accession No. ABJ63754.1, dated Mar. 2010, 1 page.
GenBank Accession No. ABK71854.1, Jan. 31, 2014, 2 pages.
GenBank Accession No. ABK75684.1, Jan. 31, 2014, 2 pages.
GenBank Accession No. ACC40567.1, Jan. 31, 2014, 2 pages.
GenBank Accession No. ACJ06772.1, Dec. 4, 2009, 1 page.
GenBank Accession No. ADG98140.1, Jan. 28, 2014, 2 pages.
GenBank Accession No. ADK19581.1, Sep. 20, 2010, 2 pages.
GenBank Accession No. AEA39183.1, Apr. 4, 2011, 1 page.
GenBank Accession No. AJ012480.1, Apr. 2005, 2 pages.
GenBank Accession No. AY143338, Apr. 2003, 5 pages.
GenBank Accession No. AY495697, Mar. 2004, 3 pages.
GenBank Accession No. BAB91331.1, retrieved May 19, 2014, 1 page.
GenBank Accession No. BAC06606, Aug. 1, 2002, 1 page.
GenBank Accession No. BAD69624, Sep. 2005, 1 page.

(56) References Cited

OTHER PUBLICATIONS

GenBank Accession No. BAF92773, Nov. 27, 2007, 1 page.
GenBank Accession No. BAF94304.1, retrieved May 19, 2014, 1 page.
GenBank Accession No. CAA44858.1, Apr. 28, 1992, 1 page.
GenBank Accession No. CAA81612.1, Apr. 18, 2005, 2 pages.
GenBank Accession No. CAA90836.1, Apr. 18, 2005, 2 pages.
GenBank Accession No. CAB13029.2, Nov. 20, 1997, 2 pages.
GenBank Accession No. CAC48239.1, Apr. 15, 2005, 2 page.
GenBank Accession No. CAE26094.1, Apr. 17, 2005, 2 pages.
GenBank Accession No. CAE26097.1, Apr. 17, 2005, 2 pages.
GenBank Accession No. CAH04396.1, Apr. 7, 2005, 1 page.
GenBank Accession No. CAH04397.1, Apr. 7, 2005, 2 pages.
GenBank Accession No. CAH04398.1, Apr. 7, 2005, 1 page.
GenBank Accession No. CCC78182.1, dated Jul. 2011, 1 page.
GenBank Accession No. D84432, replaced by Q9SKC9.1, Feb. 2005, 2 pages.
GenBank Accession No. EFV11917.1, Sep. 9, 2013, 2 pages.
GenBank Accession No. EIV11143.1, Jun. 19, 2012, 2 pages.
GenBank Accession No. JA114148, Apr. 2011, 1 page.
GenBank Accession No. JA114151, Apr. 2011, 1 page.
GenBank Accession No. JA114154, Apr. 2011, 1 page.
GenBank Accession No. JA114157, Apr. 2011, 1 page.
GenBank Accession No. L42023, Oct. 2009, 285 pages.
GenBank Accession No. NM_001246944, Dec. 2011, 2 pages.
GenBank Accession No. NM_001247852, Dec. 2011, 2 pages.
GenBank Accession No. NM_133240, Feb. 25, 2002, 2 pages.
GenBank Accession No. P22822, Mar. 1, 1992, 1 page.
GenBank Accession No. P94129 (replaced by Q6F7B8), Mar. 1, 2004, 1 page.
GenBank Accession No. S48141, May 1993, 2 pages.
GenBank Accession No. XM_001827609, Mar. 2011, 2 pages.
GenBank Accession No. YP_001394144.1, Jul. 26, 2007, 1 page.
GenBank Accession No. YP_400611, Nov. 10, 2005, 2 pages.
GenBank Accession No. YP_959486, Jan. 3, 2007, 2 pages.
GenBank Accession No. YP_959769, Jan. 3, 2007, 2 pages.
Gerbling et al., "A new acyl-CoA synthetase, located in higher plant cytosol," J Plant Physiol, 1994, 143:561-564.
Gloeckler et al., "Cloning and characterization of the *Bacillus sphaericus* genes controlling the bioconversion of pimlate into dethiobiotin," Gene, 1990, 87:63-70.
Gloerich et al., "Peroxisomal trans-2-enoyl-CoA reductase is involved in phytol degradation," FEBS Letters 2006, 580:2092-2096.
Gocke et al., "Comparative characterization of ThPP-dependent decarboxylases," J. Mol. Cat. B: Enzymatic, 2009, 61:30-35.
Gonzalez-Lopez, "Genetic control of extracellular protease synthesis in the yeast *Yarrowia lipolytica*," Genetics, 2002, 160: 417-427.
Graupner et al., "Identification of the gene encoding sulfopyruvate decarboxylase, an enzyme involved in biosynthesis of coenzyme M," J Bacterial., 2000, 182: 4862-4867.
Guerrillot et al., "Purification and Characterization of Two Aldehyde Dehydrogenases from *Pseudomonas aeruginosa*," Eur. J. Biochem. 1977, 81:185-192.
Hall, "The Contribution of Horizontal Gene Transfer to the Evolution of Fungi," Duke University Libraries, May 10, 2007, 163 pages.
Hall, "Asymmetric bioreduction of activated alkenes using cloned 12-oxophytodienoate reductase isoenzymes OPR-1 and OPR-3 from *Lycopersicon esculentum* (tomato): a striking change of stereoselectivity," Agnew Chem Int. Ed., 2007, 46:3934-3937.
Han et al., "Oxaloacetate hydrolase, the C—C bond lyase of oxalate secreting fungi," J. Biol. Chem. 2007, 282:9581-9590.
Harrison and Harwood, "The pimFABCDE operon from *Phodopseudomonas palustris* mediates dicarboxylic acid degradation and participates in anaerobic benzoate degradation," Microbiology, 2005, 151:727-736.
Harwood and Parales, "The beta-ketoadipate pathway and the biology of self-identity," Ann. Rev. Microbiol., 1996, 50:553-590.
Harwood et al., "Anaerobic metabolism of aromatic compounds via the benzoyl-CoA pathway," FEMS Microbiology Reviews, 1999, 22:439-458.

Hasson et al., "The crystal structure of benzoylformate decarboxylase at 1.6A resolution—Diversity of catalytic residues in ThDP-dependent enzymes," Biochemistry, 1998, 37:9918-9930.
Hayaishi et al., "Enzymatic Studies on the Metabolism of β-Alanine," J. Biol. Chem., 1961, 236, p. 781-790.
Haywood et al., "Characterization of two 3-ketothiolases possessing differing substrate specificities in the polyhydroxyalkanoate synthesizing organism *Alcaligenes eutrophus*," FEMS Microbiology Letters 1988, 52(1-2):91-96.
He et al., "*Nocardia* sp. carboxylic acid reductase: cloning, expression, and characterization of a new aldehyde oxidoreductase family," Applied and Environmental Microbiology, 2004, 70:1874-1881.
Heath et al., "The enoyl-[acyl-carrier-protein] reductases FabI and FabL from *Bacillus subtilis*," J Biol Chem., 275(51):40128-40133, Dec. 22, 2000.
Hermann et al, "Industrial production of amino acids by coryneform bacteria," J Biotechnol. 2003, 104(1-3):155-172.
Hess et al., "Extremely thermostable esterases from the thermoacidophilic euryarchaeon *Picrophilus torridus*," Extremophiles, 2008, 12:351-364.
Ho and Weiner, "Isolation and characterization of an aldehyde dehydrogenase encoded by the aldB gene of *Escherichia coli*," J. Bacteriol., 2005, 187(3):1067-1073.
Hoffmeister et al., "Mitochondrial trans-2-enoyl-CoA reductase of wax ester fermentation from *Euglena gracilis* defines a new family of enzymes involved in lipid synthesis," J Biol Chem., 280(6):4329-4338. Epub Nov. 29, 2004.
Hofvander et al., "A prokaryotic acyl-CoA reductase performing reduction of fatty acyl-CoA to fatty alcohol," FEBS Letters, 2001, 585:3538-3543.
Holden et al., "Chorismate lyase: kinetics and engineering for stability," Biochim Biophys Acta., Jan. 31, 2002, 1594(1):160-167.
Hooks et al., "Long-chain acyl-CoA oxidases of *Arabidopsis*," Plant J., 1999, 20:1-13.
Hotta et al., "Extremely Stable and Versatile Carboxylesterase from a Hyperthermophilic Archaeon," Applied and Environmental Microbiology, 2002, 68(8):3925-3931.
Howell et al., "Alpha-keto acid chain elongation reactions involved in the biosynthesis of coenzyme B (7-mercaptoheptanoyl threonine phosphate) in methanogenic Archaea," Biochemistry, 1989, 37: 10108-10117.
Howell et al., "Identification of enzymes homologous to isocitrate dehydrogenase that are involved in coenzyme B and leucine biosynthesis in methanoarchaea," J Bacteriol., Sep. 2000, 182: 5013-5016.
Hugler et al., "Malonyl-coenzyme A reductase from *Chloroflexus aurantiacus*, a key enzyme of the 3-hydroxypropionate cycle for autotrophic CO(2) fixation," J. Bacteriology, 2002, 184:2404-2410.
Huhn et al., "Identification of the membrane protein SucE and its role in succinate transport in *Corynebacterium glutamicum*," Appl Microbiol Biotechnol. 2011, 89(2):327-335.
Hunt et al., "Characterization of an acyl-CoA thioesterase that functions as a major regulator of peroxisomal lipid metabolism," J. Biol Chem, 2002, 277:1128-1138.
International Preliminary Report on Patentability for International Application No. PCT/US2012/069934, mailed Jun. 17, 2014, 15 pages.
International Preliminary Report on Patentability in International Application No. PCT/US2012/042777, mailed Jan. 10, 2013, 22 pages.
International Preliminary Report on Patentability in International Application No. PCT/US2012/044984, mailed Jan. 28, 2014, 11 pages.
International Search Report and Written Opinion for International Application No. PCT/US2012/069934, mailed Jan. 17, 2014, 21 pages.
International Search Report and Written Opinion in International Application No. PCT/US2012/042747, mailed Jan. 14, 2013, 19 pages.
International Search Report and Written Opinion in International Application No. PCT/US2012/042777, mailed Sep. 11, 2012, 9 pages.

(56) References Cited

OTHER PUBLICATIONS

International Search Report and Written Opinion in International Application No. PCT/US2012/044984, mailed Dec. 17, 2013, 17 pages.
International Search Report and Written Opinion in International Application No. PCT/US2012/071472, mailed Dec. 17, 2013, 17 pages.
International Search Report and Written Opinion in International Application No. PCT/US2013/075058, mailed Sep. 15, 2014, 17 pages.
International Search Report and Written Opinion in International Application No. PCT/US2013/075087, mailed Aug. 4, 2014, 18 pages.
International Search Report and Written Opinion in International Application No. PCT/US2013/077413, mailed Jul. 22, 2014, 20 pages.
International Search Report and Written Opinion in International Application No. PCT/US2013/077419, mailed Jun. 16, 2014, 19 pages.
International Search Report and Written Opinion in International Application No. PCT/US2013/077420, mailed Jul. 21, 2014, 21 pages.
International Search Report and Written Opinion in International Application No. PCT/US2013/077411, mailed Sep. 24, 2014, 18 pages.
International Search Report and Written Opinion in International Application No. PCT/US2013/077423, mailed Jul. 21, 2014, 22 pages.
International Search Report and Written Opinion in International Application No. PCT/US2013/077445, mailed Sep. 15, 2014, 17 pages.
Invitation to Pay Additional Fees in International Application No. PCT/US2013/075058, mailed Jul. 7, 2014, 7 pages.
Invitation to Pay Additional Fees in International Application No. PCT/US2013/07745, mailed Jul. 7, 2014, 9 pages.
Invitation to Pay Fees in International Application No. PCT/US2013/075087, mailed May 16, 2014, 9 pages.
Invitation to Pay Fees in International Application No. PCT/US2013/077411, mailed Jul. 16, 2014, 9 pages.
Invitation to Pay Fees in International Application No. PCT/US2013/077413, mailed May 12, 2014, 9 pages.
Invitation to Pay Fees in International Application No. PCT/US2013/077419, mailed Apr. 16, 2014, 9 pages.
Invitation to Pay Fees in International Application No. PCT/US2013/077420, mailed May 13, 2014, 9 pages.
Invitation to Pay Fees in International Application No. PCT/US2013/077423, mailed May 13, 2014, 10 pages.
Invitation to Pay Fees in International Application No. PCT/US2013/077430, mailed Aug. 25, 2014, 9 pages.
Ishige et al., "Wax Ester Production from n-Alkanes by *Acinetobacter* sp. Strain M-1: Ultrastructure of Cellular Inclusions and Role of Acyl Coenzyme A Reductase," Appl. Envtl. Microbilogy, 2002, 68:1192-1195.
Ishikawa et al., "The pathway via D-galacturonate/L-galactonate is significant for ascorbate biosynthesis in *Euglena gracilis*: identification and functional characterization of aldonolactonase," Journal of Biologiocal Chemistry, 2008, 283:31133-31141.
Iwaki et al., "Cloning and Characterization of a Gene Cluster Involved in Cyclopentanol Metabolism in *Comamonas* sp. Strain NCIMB 9872 and Biotransformations Effected by *Escherichia coli*-Expressed Cyclopentanone 1,2-Monooxygenase," Appl Environ Microbiol., 2002, 68(11):5671-5684, 14 pages.
Iwaki et al., "Identification of a Transcriptional Activator (ChnR) and a 6-Oxohexanoate Dehydrogenase (ChnE) in the Cyclohexanol Catabolic Pathway in *Acinetobacter* sp. Strain NCIMB 9871 and Localization of the Genes That Encode Them," Appl. Environ. Microbiol., 1999, 65(11):5158-5162.
Izumi et al., "Structure and Mechanism of HpcG, a Hydratase in the Homoprotocatechuate Degradation Pathway of *Escherichia coli*," J. Mol. Biol., 2007, 370:899-911.

Izumi et al., "The pimeloyl-CoA synthetase responsible for the first step in biotin biosythesis by microorganisms," Agr. Biol. Chem., 1974, 38:2257-2262.
Jacob et al., "Glutaconate CoA-transferase from *Acidamiococcus fermentans*: the crystal structure reveals homology with other CoA-transferases," Structure, 1997, 5:415-426.
Jang et al., "Bio-based production of C2-C6 platform chemicals," Biotechnol. & Bioengineering, 2012, 109(10):2437-2459.
Jarboe, "YqhD: a broad-substrate range aldehyde reductase with various applications in production of biorenewable fuels and chemicals," Appl Microbiol Biotechnol., 2011, 89(2):249-257.
Jaremko et al., "The initial metabolic conversion of levulinic acid in *Cupriavidus nector*," J. Biotechnol., 2011, 155(3):293-298.
Jeyakanthan et al., "Substrate specificity determinants of the methanogen homoaconitase enzyme: structure and function of the small subunit," Biochemistry, 2010, 49:2687-2696.
Jing et al., "Phylogenetic and experimental characterization of an acyl-ACP thioesterase family reveals significant diversity in enzymatic specificity and activity," BMC Biochemistry, 2011, 12:44, 16 pages.
Joon-Young et al., "Production of 1,2-Propanediol from Glycerol in *Saccharomyces cerevisiae*," J. Microbiology and Biotechnology, May 19, 2011, 21(8):846-853.
Kakugawa et al., "Purification and Characterization of a Lipase from the Glycolipid-Producing Yeast *Kurtzmanomyces* sp I-11," Bioscience Biotechnology Biochemistry, 2002, 66(5): 978-985.
Kato and Asano, "Cloning, nucleotide sequencing, and expression of the 2-methylasparatate ammonia-lyase gene from *Citrobacter amalonaticus* strain YG-1002," Appl. Microbiol Biotechnol, 1998, 50:468-474.
Kaulmann et al., "Substrate spectrum of omega-transaminase from *Chromobacterium violaceum* DSM30191 and its potential for biocatalysis," Enzyme Microb Technol. 2007, 41:628-637.
Kikuchi et al., "Characterization of a second lysine decarboxylase isolated from *Escherichia coli*," J Bacteriol, 1997, 179(14): 4486-4489.
Kim et al., "Cloning and characterization of a cyclohexanone monooxygenase gene from *Arthrobacter* sp. L661," Biotechnology Bioprocess Engineering, 2008, 13:40-47.
Kim, "Purification and properties of a diamine alpha-ketoglutarate transaminase from *Escherichia coli*," J Biol Chem 1964, 239(3):783-786.
Kitzing et al., "The 1.3 A crystal structure of the flavoprotein YqjM reveals a novel class of Old Yellow Enzymes," J. Biol. Chem., 2005, 280:27904-27913.
Koch et al., "Products of Enzymatic Reduction of Benzoyl-CoA, A Key Reaction in Anaerobic Aromatic Metabolism," Eur. J. Biochemistry, Jan. 1993, 211(3):649-661.
Koch et al., "In Vivo Evolution of Butane Oxidation by Terminal Alkane Hydroxylases AlkB and CYP153A6," Appl. Environ. Microbiol., 2009, 75(2):337-344.
Kockelkorn and Fuchs, "Malonic semialdehyde reductase, succinic semialdehyde reductase, and succinyl-coenzyme A reductase from *Metallosphaera sedula*: enzymes of the autotrophic 3-hydroxypropionate/4-hydroxybutyrate cycle in Sulfolobales," J. Bacteriology, 2009, 191:6352-6362.
Kolattukudy, "Enzymatic synthesis of fatty alcohols in *Brassica oleracea*," Archives of Biochemistry and Biophysics, 1971, 142(2):701-709.
Köpke et al., "2,3-Butanediol Production by Acetogenic Bacteria, an Alternative Route to Chemical Synthesis, Using Industrial Waste Gas," Appl Environ Microbiol., 2011, 77(15):5467-5475.
Kulkarni and Kanekar, "Bioremediation of epsilon-caprolactam from nylon-6 waste water by use of *Pseudomonas aeruginosa* MCM B-407," Curr. Microbiol., 1998, 37:191-194.
Kung et al., "Cyclohexanecarboxyl-coenzyme A (CoA) and cyclohex-1-ene-1-carboxyl-CoA dehydrogenases, two enzymes involved in the fermentation of benzoate and crotonate in *Syntrophus aciditrophicus*," J Bacteriol., 195(14):3193-3200, Epub May 10, 2013.

(56) References Cited

OTHER PUBLICATIONS

Lan et al., "Oxygen-tolerant coenzyme A-acylating aldehyde dehydrogenase facilitates efficient photosynthetic n-butanol biosynthesis in cyanobacteria," Energy Environ Sci, 2013, 6:2672-2681.

Larroy et al., "Characterization of the *Saccharomyces cerevisiae* YMR318C (ADH6) gene product as a broad specificity NADPH-dependent alcohol dehydrogenase: relevance in aldehyde reduction," Biochem J., 2002, 361(Pt 1):163-172.

Le Dall et al., "Multiple-copy integration in the yeast *Yarrowia lipolytica*," Current Genetics, 1994 26:38-44.

Lee and Meighen, "Cysteine-286 as the site of acylation of the LUX-specific fatty acyl-CoA reductase," Biochim Biophys Acta, 1997, 1338:215-222.

Lee et al., "Metabolic Engineering of Pentose Phosphate Pathway in *Ralstonia eutropha* for Enhanced Biosynthesis of Poly-β-hydroxybutyrate," Biotechnology Progress, 2003, 19(5):1444-1449.

Lee et al., "Synthesis of pure meso-2,3-butanediol from crude glycerol using an engineered metabolic pathway in *Escherichia coli*," Appl Biochem Biotechnol., 2012, 166(7):1801-1813.

Li et al., "*Cupriavidus necator* JMP 134 rapidly reduces furfural through a Zn-dependent alcohol dehydrogenase," Biodegradation, 2011, 22:1215-1225.

Lim et al., "Amplification of the NADPH-related genes zwf and gnd for the oddball biosynthesis of Phb in an *E. coli* transformant harboring a cloned phbCAB operon," J Bioscience and Bioengineering, 2002, 93(6):543-549.

Lin and Cronan, "Closing in on complete pathways of biotin biosynthesis," Molecular Biosystems, 2011, 7:1811-1821.

Lin et al., "Biotin Sythesis Begins by Hijacking the Fatty Acid Synthetic Pathway," Nature Chem Biol., Sep. 2010, 6:682-688.

Lin et al., "The BioC O-Methyltransferase Catalyzed Methyl Esterification of Malonyl-Acyl Carrier Protein, an Essential Step in Biotin Synthesis," Journal of Biological Chemistry, Sep. 2012, 287(44):37010-37020.

Lin, "Biotin Synthesis in *Escherichia coli*," PhD Dissertation, University of Illinois at Urbana-Champaign, 2012, 140 pages.

Liu and Chen, "Production and characterization of medium-chain-length polyhydroxyalkanoate with high 3-hydroxytetradecanoate monomer content by fadB and fadA knockout mutant of *Pseudomonas putida* KT2442," Appl. Microbiol. Biotechnol., 2007, 76(5):1153-1159.

Liu et al., "Two novel metal-independent long-chain alkyl alcohol dehydrogenases from *Geobacillus thermodenitrificans* NG80-2," Microbiology, 2009, 155:2078-2085.

Lopez-Sanchez et al., "Tetralin-Induced and ThnR-Regulated Aldehyde Dehydrogenase and β-Oxidation Genes in *Sphingomonas macrogolitabida* Strain TFA," Appl. Environ. Microbiol., 2010, 76(1):110-118.

Luo et al., "Production of 3-hydroxypropionic acid through propionaldehyde dehydrogenase PduP mediated biosynthetic pathway in *Klebsiella pneumoniae*," Bioresource Technology, 2012, 103:1-6.

Lütke-Eversloh & Steinbüchel, "Biochemical and molecular characterization of a succinate semialdehyde dehydrogenase involved in the catabolism of 4-hydroxybutyric acid in *Ralstonia eutropha*," FEMS Microbiology Letters, 1999, 181(1):63-71.

Mack and Buckel, "Conversion of glutaconate CoA-transferase from *Acidaminococcus fermentans* into an acyl-CoA hydrolase by site-directed mutagenesis," FEBS Letters, 1997, 405:209-212.

Maeda et al., "Purification and characterisation of a biodegradable plastic-degrading enzyme from *Aspergillus oryzae*," Applied and Environmental Biotechnology, 2005, 67: 778-788.

Mahadik et al., "Production of acidic lipase by *Aspergillus niger* in solid state fermentation," Process Biochemistry, 2002, 38: 715-721.

Martin and Prather, "High-titer production of monomeric hydroxyvalerates from levulinic acide *Pseudomonas putida*," J. Biotechnol., 2009, 139: 61-67.

Martinez et al., "*Fusarium solani* cutinase is a lipolytic enzyme with a catalytic serine accessible to solvent," Nature, 1992, 356:615-618.

Matsumoto et al., "A new pathway for poly(3-hydroxybutyrate) production in *Escherichia coli* and *Corynebacterium glutamicum* by functional expression of a new acetoacetyl-coenzyme a synthase," Biosci. Biotechnol. Biochem., 2011, 75(2):364-366.

Mawal and Deshmukh, "Alpha-aminoadipate and kynurenine aminotransferase activities from rat kidney. Evidence for separate identity," J. Biol Chem, 1991, 266(4):2573-2575.

McAndrew et al., "Structural basis for substrate fatty acyl chain specificity: crystal structure of human very-long-chain acyl-CoA dehydrogenase," J. Biol. Chem., 2008, 283:9435-9443.

Meijnen et al., "Improved p-hydroxybenzoate production by engineered *Pseudomonas putida* S12 by using a mixed-substrate feeding strategy," Appl. Microbiol. Biotechnol., 2011, 90:885-893.

Mhetras et al., "Purification and characterization of acidic lipase from *Aspergillus niger* NCIM 1207," Bioresource Technology, 2009, 100: 1486-1490.

Millar et al., "CUT1, an *Arabidopsis* Gene Required for Cuticular Wax Biosynthesis and Pollen Fertility, Encodes a Very-Long-Chain Fatty Acid Condensing Enzyme," The Plant Cell, May 1999, 11(5):825-838, retrieved on Sep. 30, 2014, http://www.plantcell.org/content/11/5/825.full.

Miyazaki et al., "Alpha-Aminoadipate aminotransferase from an extremely thermophilic bacterium, *Thermus thermophilus*," Microbiology, 2004, 150(7): 2327-2334.

Mo et al., "Connecting extracellular metabolomic measurements to intracellular flux states in yeast," BMC Systems Biology, 2009, 3(37):1-17.

Mouttaki et al., "Cyclohexane Carboxylate and Benzoate Formation from Crotonate in *Sytrophus aciditrophicus*," Applied and Environ Microbiology, Feb. 2007, 73(3):930-938.

Murphy et al., "*Fusarium* polycaprolactone depolymerase is cutinase," Appl. Environm. Microbiol., 1996, 62:456-460.

Naggert et al., "Cloning, sequencing, and characterization of *Escherichia coli* thioesterase II," J. Biol. Chem., 1991, 266(17):11044-11050.

Neyfakh, "The Multidrug Efflux Transporter of *Bacillus subtilis* is a Structural and Functional Homolog of the *Staphylococcus* NorA Protein," Antimicrob Agents Chemother, 1992, 36(2):484485.

Ng et al., "Quinolone Resistance Mediated by norA: Physiologic Characterization and Relationship to flqB, a Quinolone Resistance Locus on the *Staphylococcus aureus* Chromosome," Antimicrob Agents Chemother, 1994, 38(6):1345-1355.

Nicol et al., "Bioconversion of crude glycerol by fungi," Applied Microbiology and Biotechnology, Feb. 10, 2012, 93(5):1865-1875.

Nieder and Shapiro, "Physiological function of the *Pseudomonas putida* PpG6 (*Pseudomonas oleovorans*) alkane hydroxylase: monoterminal oxidation of alkanes and fatty acids," J. Bacteriol., 1975, 122(1):93-98.

Nishimaki et al., "Studies on the Metabolism of Unsaturated Fatty Acids. XIV.1 Purification and Properties of NADPH-Dependent trans-2-Enoyl-CoA Reductase of *Escherichia coli* K-12," J. Biochem., 1984, 95:1315-1321.

Nomura et al., "Expression of 3-Ketoacyl-Acyl Carrier Protein Reductase (fabG) Genes Enhances Production of Polyhydroxyalkanoate Copolymer from Glucose in Recombinant *Escherichia coli* JM109," Appl. Environ. Microbiol., 2005, 71(8):4297-4306.

Ohashi et al., "Continuous production of lactic acid from molasses by perfusion culture of *Lactococcus lactis* using a stirred ceramic membrane reactor," J. Bioscience and Bioengineering, 1999, 87(5):647-654.

Okuhara et al., "Formation of Glutaric and Adipic Acids from n-Alkanes with Odd and Even Numbers of Carbons by *Candida tropicalis* OH23," Agr. Biol. Chem., 1971, 35(9):1376-1380.

Onakunle et al., "The formation and substrate specificity of bacterial lactonases capable of enantioselective resolution of racemic lactones," Enzyme and Microbial Technology, 1997, 21: 245-251.

Oppenheim and Dickerson, "Adipic Acid," Kirk-Othmer Encyclopedia of Chemical Technology, 2003.

Ouchi et al., "Dual roles of a conserved pair, Arg23 and Ser20, in recognition of multiple substrates in alpha-aminoadipate aminotransferase from *Thermus thermophilus*," Biochem Biophys Res Commun, 2009, 388(1):21-27.

(56) References Cited

OTHER PUBLICATIONS

Palosaari and Rogers, "Purification and properties of the inducible coenzyme A-linked butyraldehyde dehydrogenase from *Clostridium acetobutylicum*," J. Bacteriol., 1988, 170(7):2971-2976.

Papanikolaou et al., "Citric acid production by *Yarrowia lipolytica* cultivated on olive-mill wastewater-based media," Bioresource Technol., 2008, 99(7):2419-2428.

Parthasarthy et al., "Substrate specificity of 2-hydroxyglutaryl-CoA dehydratase from *Clostiridium symbiosum*: Toward a bio-based production of adipic acid," Biochemistry, 2011, 50:3540-3550.

Pelletier and Harwood et al., "2-Hydroxycyclohexanecarboxyl coenzyme A dehydrogenase, an enzyme characteristic of the anaerobic benzoate degradation pathway used by *Rhodopseudomonas palustris*," J Bacteriol., 182(10):2753-2760, May 2000.

Perez-Pantoja et al., "Metabolic reconstruction of aromatic compounds degradation from the genome of the amazing pollutant-degrading bacterium Cupriavidus necator JMP134," FEMS Microbiol. Rev., 2008, 32:736-794.

Peterson et al., "The Thermal Stability of the *Fusarium solani* pisi Cutinase as a Function of pH," BioMed Research International, 2001, 1.2:62-69.

Pignede et al., "Autocloning and Amplification of LIP2 in *Yarrowia lipolytica*," Appl. Environ. Microbiol, 2000 66:3283-3289.

Pignede et al., "Characterization of an extracellular lipase encoded by LIP2 in *Yarrowia lipolytica*," Journal of Bacteriology, 2000, 182:2802-2810.

Ploux et al., "Investigation of the first step of biotin biosynthesis in *Bacillus sphaericus*: Purification and characterization of the pimloyl-CoA sythase, and uptake of pimelate," Biochem J., 1992, 287:685-690.

Prybylski et al., "Third-generation feed stocks for the clean and sustainable biotechnological production of bulk chemicals: synthesis of 2-hydroxyisobutyric acid," Energy, Sustainability and Society, 2012, 2:11.

Qian et al., "Metabolic engineering of *Escherichia coli* for the production of cadaverine: a five carbon diamine," Biotechnol Bioeng, 2011, 108(1):93-103.

Qiu et al., "Crystal structure and substrate specificity of the β-ketoacyl-acyl carrier protein synthase III (FabH) from *Staphylococcus aureus*," Protein Sci, 2005, 14(8):2087-2094.

Rajashekhara et al., "Propionyl-coenzyme A synthetases of *Ralstonia solanacearum* and *Salmonella choleraesuis* display atypical kenetics," FEBS Letters, 2004, 556:143-147.

Ramsay et al., "Use of a Nylon Manufacturing Waste as an Industrial Fermentation Substrate," Applied and Environmental Microbiology, 1986, 52(1):152-156.

Ray et al., "Cocrystal structures of diaminopimelate decarboxylase: mechanism, evolution, and inhibition of an antibiotic resistance accessory factor," Structure, 2002, 10(11):1499-1508.

Rea et al., "Structure and Mechanism of HpcH: A Metal Ion Dependent Class II Aldolase from the Homoprotocatechuate Degradation Pathway of *Escherichia coli*," J. Mol. Bio., 2007, 373:866-876.

Rohdich et al., "Enoate reductases of Clostridia. Cloning, sequencing, and expression," J. Biol. Chem., 2001, 276:5779-5787.

Roje, "Vitamin B biosynthesis in plants," Phytochemistry, 2007, 68:1904-1921.

Roujeinikova et al., "Structural studies of fatty acyl-(acyl carrier protein) thioesters reveal a hydrophobic binding cavity that can expand to fit longer substrates," J Mol Biol., 365(1):135-145, Epub Sep. 23, 2006.

Ryu et al., "A novel synthesis of .beta.-trichlorostannyl ketones from siloxycyclopropanes and their facile dehydrostannation affording 2-methylene ketones," JOC, 1986, 51:2389-2391.

Salcher and Lingens, "Regulation of phospho-2-keto-3-deoxyheptonate aldolase (DAHP synthase) and anthranilate synthase of *Pseudomonas aureofaciens*," J Gen Microbiol., 121(2):473-476, Dec. 1980.

Sambrook et al., Molecular Cloning—a Laboratory Manual, Cold Spring Harbor Laboratory Press, 2001.

Samsonova et al., "Molecular cloning and characterization of *Escherichia coli* K12 ygjG gene," BMC Microbiology, 2003, 3:2.

Sanders et al., "Characterization of the human ω-oxidation pathway for ω-hydroxy-very-long-chain fatty acids," FASEB Journal, 2008, 22(6):2064-2071.

Sanders et al., "Evidence for two enzymatic pathways for ω-oxidation of docosanoic acid in rat liver microsomes," J. Lipid Research, 2005, 46(5):1001-1008.

Satoh et al., "Enzyme-catalyzed poly(3-hydroxybutyrate) synthesis from acetate with CoA recycling and NADPH regeneration in vitro," J Bioscience and Bioengineering, 2003, 95(4):335-341.

Scheller et al., "Generation of the Soluble and Functional Cytosolic Domain of Microsomal Cytochrome P450 52A3," J Biol Chem., 1994, 269(17):12779-12783.

Schirmer et al., "Microbial Biosythesis of Alkanes," Science, 2010, 329:559-562.

Schwartz et al., "A proteomic view of the facultatively chemolithoautotrophic lifestyle of *Ralstonia eutropha* H16," Proteomics, 2009, 9:5132-5142.

Seedorf et al., "The genome of *Clostridium kluyveri*, a strict anaerobe with unique metabolic features," Proc. Natl. Acad. Sci. USA, 2008, 105(6):2128-2133.

Shapiro et al., "Remarkable Diversity in the Enzymes Catalyzing the Last Step in Synthesis of the Pimelate Moiety of Biotin," PLoSOne, Nov. 2012, 7(11):e49440, 11 pages.

Shen et al., "Driving Forces Enable High-Titer Anaerobic 1-Butanol Synthesis in *Escherichia coli*," Appl. Environ. Microbiol., 2011, 77(9):2905-2915.

Shikata et al., "A novel ADP-forming succinyl-CoA synthetase in *Thermococcus kodakaraensis* structurally related to the archaeal nucleoside diphosphate-forming acetyl-CoA synthetases," J. Biol. Chem, 2007, 282(37):26963-26970.

Siegert et al., "Exchanging the substrate specificities of pyruvate decarboxylase from *Zymomonas mobilis* and benzoylformate decarboxylase from *Pseudomonas putida*," Port. Eng. Des. Sel., 2005, 18:345-357.

Simon et al., "Chiral Compounds Synthesized by Biocatalytic Reductions [New Synthetic Methods (51)]," Angew Chem Ed Engl., 1985, 24:539-553.

Simon, "Properties and mechanistic aspects of newly found redox enzymes from anaerobes suitable for bioconversions on preparatory scale," Pure and Appl. Chem, 1992, 64:1181-1186.

Slater et al., "Multiple β-Ketothiolases Mediate Poly(β-Hydroxyalkanoate) Copolymer Synthesis in *Ralstonia eutropha*," J Bacteriol., 1998, 180(8):1979-1987.

Smith et al., "Complete genome sequence of *Methanobacterium thermoautotrophicum* deltaH: functional analysis and comparative genomics," J Bacteriol., 1997, 179: 7135-7155.

Smith et al., "Structural analysis of ligand binding and catalysis in chorismate lyase," Archives of Biochemistry and Biophysics, Jan. 2006, 445(1):72-80.

Stok et al., "Expression, Purification, and Characterization of BioI: A Carbon—Carbon Bond Cleaving Cytochrome P450 Involved in Biotin Biosynthesis in *Bacillus subtilis*," Archives of Biochemistry and Biophysics, Dec. 2000, 384(2):351-360.

Strassner et al., "A homolog of old yellow enzyme in tomato. Spectral properties and substrate specificity of the recombinant protein," J. Biol. Chem. 1999, 274:35067-35073.

Stueckler, "Stereocomplementary bioreduction of alpha,beta-unsaturated dicarboxylic acids and dimethyl esters using enoate reductases: enzyme- and substrate-based stereocontrol," Org. Lett., 2007, 9:5409-5411.

Suzuki et al., "Acetylputrescine deacetylase from *Micrococcus luteus* K-11," BBA—General Subjects, 1986, 882(1):140-142.

Suzuki et al., "Antimicrobial Activity of Meropenem Against Main Bacterial Species Isolated from Patient Blood in 2006," J. Antibiot., 2007, 60(6):380-387.

Suzuki et al., "GriC and GriD Constitute a Carboxylic Acid Reductase Involved in Grixazone Biosynthesis in *Streptomyces griseus*," J. Antibiot., 2007, 60(6):380-387.

Tomita et al., "Mechanism for multiple-substrates recognition of alpha-aminoadipate aminotransferase from *Thermus thermophilus*," Proteins, 2009, 75(2):348-359.

(56) References Cited

OTHER PUBLICATIONS

Tseng et al., "Biosynthesis of chiral 3-hydroxyvalerate from single propionate-unrelated carbon sources in metabolically engineered *E. coli*," Microbial Cell Factories, 2010, 9:96.
Vamecq et al., "The microsomal dicarboxylyl-CoA synthetase," Biochem J., 1985, 230:683-693.
Van Beilen and Funhoff, "Expanding the alkane oxygenase toolbox: new enzymes and Applications," Curr. Opin. Biotechnol., 2005, 16:308-314.
Venkitasubramanian et al., "Aldehyde oxidoreductase as a biocatalyst: Reductions of vanillic acid," Enzyme and Microbial Technology, 2008, 42:130-137.
Vioque et al., Resolution and purification of an aldehyde-generating and an alcohol-generating fatty-acyl-CoA reductase from Pea leaves (*Pisum sativum* L), Archives of Biochemistry and Biophysics, 1997, 340(1):64-72.
Wahlen et al., "Purification, characterization and potential bacterial wax production role of an NADPH-dependent fatty aldehyde reductase from *Marinobacter aquaeolei* VT8," Appl. Environ Microbiol, 2009, 75:2758-2764.
Wang and Kolattukudy, "Solubilization and purification of aldehyde-generation fatty acyl-CoA reductase from green alga *Botryococcus braunii*," FEBS Letters, 1995, 370:15-18.
Wee et al., "Biotechnological Production of Lactic Acid and Its Recent Applications," Food Technol. Biotechnol., 2006, 44(2):163-172.
Westin et al., "Molecular cloning and characterization of two mouse peroxisome proliferatoractivated receptor alpha (PPARalpha)-regulated peroxisomal acyl-CoA thioesterases," J. Biol Chem, 2004, 279:21841-21848.
Westin et al., "The identification of a succinyl-CoA thioesterase suggests a novel pathway for succinate production in peroxisomes," J. Biol Chem, 2005, 280:38125-38132.
White and Kelly, "Purification and Properties of Diaminopimelate Decarboxylase From *Escherichia coli*," Biochem J., 1965, 96:75-84.
White, "A novel biosynthesis of medium chain length alpha-ketodicarboxylic acids in methanogenic archaebacteria," Archivers of Biochemistry and Biophysics, 1989, 270: 691-697.
White, "Biosynthesis of the 7-mercaptoheptanoic acid subunit of component B [(7-mercaptoheptanoyl)threonine phosphate] of methanogenic bacteria," Biochemistry, 1989, 28: 860-865.
White, "Steps in the conversion of a-ketosuberate to 7-mercaptoheptanoic acid in methanogenic bacteria," Biochemistry, 1989, 28: 9417-9423.
Widmann et al., "Structural classification by the Lipase Engineering Database: a case study of *Candida antarctica* lipase A," BMC Genomics, 2010, 11:123-130.
Willis et al., "Characterization of a fatty acyl-CoA reductase from *Marinobacter aquaeolei* VT8: a bacterial enzyme catalyzing the reduction of fatty acyl-CoA to fatty alcohol," Biochemistry, 2011, 50:10550-10558.
Wilson and Bouwer, "Biodegradation of aromatic compounds under mixed oxygen/denitrifying conditions: a review," J Ind Microbiol Biotechnol., 18(2-3):116-130, Feb.-Mar. 1997.
Wischgoll et al., "Structural basis for promoting and preventing decarboxylation in glutarylcoenzyme, A dehydrogenases," Biochemistry, 2010, 49:5350-5357.
Woolridge et al., "Efflux of the natural polyamine spermidine facilitated by the *Bacillus subtilis* multidrug transporter Blt," J Biol Chem., 1997, 272(14):8864-8866.
Xiong et al., "A bio-catalytic approach to aliphatic ketones," Sci Rep., 2:311, Epub Mar. 13, 2012.
Yang et al., "Value-added uses for crude glycerol—a byproduct of biodiesel production," Biotechnology for Biofuels, 2012, 5:13.
Yonaha et al., "4-Aminobutyrate : 2-oxoglutarate aminotransferase of *Streptomyces griseus*: Purification and properties," Eur. J. Biochem., 1985, 146:101-106.
Zhang et al., "Expanding metabolism for biosynthesis of nonnatural alcohols," Proc Natl Acad Sci U S A., 105(52):20653-20658 Epub Dec. 8, 2008.
Zhuang et al., "Divergence of function in the hot dog fold enzyme superfamily: the bacterial thioesterase YciA," Biochemistry, 2008, 47(9):2789-2796.
Zomorrodi et al., "Improving the iMM904 *S. cerevisiae* metabolic model using essentiality and synthetic lethality data," BMC Systems Biology, Dec. 2010, 4(1):1-15.
Aimin et al., "Nocardia sp. carboxylic acid reductase: cloning, expression, and characterization of a new aldehyde oxidoreductase family," Appl. Environ. Microbiol., 2004, 70:1874-1881.
Aloulou et al., "Purification and biochemical characterization of the LIP2 lipase from Yarrowia lipolytica," Biochim. Biophys. Acta, 2007, 1771:228-237.
Atsumi et al., "Acetolactate synthase from Bacillus subtilisserves as a 2-ketoisovalerate decarboxylase from isobutanol synthesis in *Escherichi coli*," Applied and Environ. Microbiol., 2009, 75(19):6306-6311.
Bergler et al., "Protein EnvM is the NADH-dependent enoyl-ACP reductase (FabI) of *Escherichia coli*," J. Bio Chem, 1993, 269(8):5493-5496.
Eikmanns and Buckel, "Properties of 5-hydroxyvalerate CoA-transferase from Clostridium aminovalericum," Biol. Chem, 1990, 371:1077-1082.
Fonknechten et al., "Clostridium sticklandii, a specialist in amino acid degradation: revisiting its metabolism through its genome sequence," BMC Genomics, 2010, 11:1-12.
GenBank Accession No. AAA23536, Apr. 26, 1993, 1 page.
GENBANK Accession No. AAA92347.1, Mar. 15, 1996, 1 page.
GenBank Accession No. AAB99100, Aug. 27, 1996, 2 pages.
GenBank Accession No. AE000666.1, Jan. 5, 2006, 309 pages.
GenBank Accession No. D87518, Jul. 31, 1997, 2 pages.
GenBank Accession No. HQ418483.1, Apr. 4, 2011, 2 pages.
GenBank Accession No. JA114119.1, Apr. 19, 2011, 1 page.
GenBank Accession No. MJ0663, Oct. 1, 2014, 4 pages.
GenBank Accession No. NC_013156.1, Jun. 10, 2013, 2 pages.
GenBank Accession No. NC_014122.1, Jun. 10, 2013, 2 pages.
GenBank Accession No. NC_015562.1, Jun. 10, 2013, 2 Pages.
GenBank Accession No. NP_247129, Jun. 10, 2013, 2 pages.
GenBank Accession No. NP_247250, Jun. 10, 2013, 2 pages.
GenBank Accession No. NP_247647, Jun. 10, 2013, 2 pages.
GenBank Accession No. YP_003127480, Jun. 10, 2013, 2 pages.
GenBank Accession No. YP_003128272, Jun. 10, 2013, 2 pages.
GenBank Accession No. YP_003615747, Jun. 10, 2013, 1 page.
GenBank Accession No. YP_003615922, Jun. 10, 2013, 2 pages.
GenBank Accession No. YP_004483786, Jul. 6, 2013, 2 pages.
Horning et al., "α-Ketoglutaric Acid," Organic Syntheses, 1955, 3: 510-512.
International Search Report and Written Opinion in International Application No. PCT/US2014/052950, mailed Dec. 3, 2014, 15 pages.
International Search Report and Written Opinion in International Application No. PCT/US2013/077430, mailed Nov. 10, 2014, 23 pages.
Invitation to Pay Additional Fees in International Application No. PCT/US2014/053222, mailed Dec. 15, 2014, 8 pages.
Klatte et al., "Redox self-sufficient whole cell biotransformation for amination of alcohols," Bioorg & Medicinal Chem, May 2014, 22: 5578-5585.
Lea et al., "Long-chain acyl-CoA dehydrogenase is a key enzyme in the mitochondrial B-oxidation of unsaturated fatty acids," Biochmica et Biophysica Acta, 2000, 1485: 121-128.
Mutti et al., "Amination of ketones by employing two new (S)-selective w-transaminases and the His-tagged w-TA from Vibrio fluvialis," Eur. J. Org. Chem, 2012, 1003-1007 (Abstract).
Prabhu et al., "Lactate and Acrylate Metabolism by Megasphaera elsdenii under Batch and Steady-State Conditions," Applied and Environ. Microbiology, Sep. 2012, 78(24): 8564-8570.
Reiser and Somerville, "Isolation of mutants of *Acinetobacter calcoaceticus* deficient in wax ester synthesis and complementation of on mutation with gene encoding a fatty acyl coenzyme A reductase," J. Bacteriol., 1997, 179:2969-2975.
Rizzarelli et al., "Evidence for Selective Hydrolysis of Aliphatic Copolyesters Induced by Lipase Catalysis," Biomacromolecules, 2004, 5:433-444.

(56) References Cited

OTHER PUBLICATIONS

Uniprot Accession No. I5YEB8, Sep. 5, 2012, 1 page.
US Non-Final Office Action in U.S. Appl. No. 13/524,883, mailed Nov. 29, 2013, 13 pages.
US Non-Final Office Action in U.S. Appl. No. 13/715,981, mailed Jun. 27, 2014, 23 pages.
US Notice of Allowance in U.S. Appl. No. 13/524,883, mailed May 29, 2014, 7 pages.
US Notice of Allowance in U.S. Appl. No. 13/715,981, mailed Dec. 16, 2014, 23 pages.
US Non-Final Office Action in U.S. Appl. No. 13/715,826, mailed Jan. 30, 2015, 24 pages.
Vyazmensky et al., "Isolation and Characterization of Subunits of Acetohydroxy Acid Synthase Isozyme III and Reconstruction of the Holoenzyme," Biochemistry, 1996, 35:10339-10346.
Zhao et al., "Prediction and characterization of enzymatic activities guided by sequence similarity and genome neighborhood networks," E-Life, Jun. 2014, 3: 1-32.

FIGURE 9

| SEQ ID NO | Organism | GENBANK reference | Amino acid sequence |
|---|---|---|---|
| 1 | Escherichia coli | AAA24665.1 | MSQALKNLLTLLNLEKIEEGLFRGQSEDLGLRQVFGGQVVGQALYAAKETVPEERLVHSF HSYFLRPGDSKKPIIYDVETLRDGNSFSARRVAAIQNGKPIFYMTASFQAPEAGFEHQKT MPSAPAPDGLPSETQIAQSLAHLLPPVLKDKFICDRPLEVRPVEFHNPLKGHVAEPHRQV WIRANGSVPDDLRVHQYILGYASDLNFLPVALQPHGIGFLEPGIQIATIDHSMWFHRPFN LNEWLLYSVESTSASSARGFVRGEFYTQDGVLVASTVQEGVMRNHN |
| 2 | Mycobacterium marinum | ACC40567.1 | MSPITREERLERRIQDLYANDPQFAAAKPATAITAAIERPGLPLPQIIETVMTGYADRPA LAQRSVEFVTDAGTGHTTLRLLPHFETISYGELWDRISALADVLSTEQTVKPGDRVCLLG FNSVDYATIDMTLARLGAVAVPLQTSAAITQLQPIVAETQPTMIAASVDALADATELALS GQTATRVLVFDHHRQVDAHRAAVESARERLAGSAVVETLAEAIARGDVPRGASAGSAPGT DVSDDSLALLIYTSGSTGAPKGAMYPRRNVATFWRKRTWFEGGYEPSITLNFMPMSHVMG RQILYGTLCNGGTAYFVAKSDLSTLFEDLALVRPTELTFVPRVWDMVFDEFQSEVDRRLV DGADRVALEAQVKAEIRNDVLGGRYTSALTGSAPISDEMKAWVEELLDMHLVEGYGSTEA GMILIDGAIRRPAVLDYKLVDVPDLGYFLTDRPHPRGELLVKTDSLFPGYYQRAEVTADV FDADGFYRTGDIMAEVGPEQFVYLDRRNNVLKLSQGEFVTVSKLEAVFGDSPLVRQIYIY GNSARAYLLAVIVPTQEALDAVPVEELKARLGDSLQEVAKAAGLQSYEIPRDFIIETTPW TLENGLLTGIRKLARPQLKKHYGELLEQIYTDLAHGQADELRSLRQSGADAPVLVTVCRA AAALLGGSASDVQPDAHFTDLGGDSLSALSFTNLLHEIFDIEVPVGVIVSPANDLQALAD YVEAARKPGSSRPTFASVHGASNGQVTEVHAGDLSLDKFIDAATLAEAPRLPAANTQVRT VLLTGATGFLGRYLALEWLERMDLVDGKLICLVRAKSDTEARARLDKTFDSGDPELLAHY RALAGDHLEVLAGDKGEADLGLDRQTWQRLADTVDLIVDPAALVNHVLPYSQLFGPNALG TAELLRLALTSKIKPYSYTSTIGVADQIPPSAFTEDADIRVISATRAVDDSYANGYSNSK WAGEVLLREAHDLCGLPVAVFRCDMILADTTWAGQLNVPDMFTRMILSLAATGIAPGSFY ELAADGARQRAHYDGLPVEFIAEAISTLGAQSQDGFHTYHVMNPYDDGIGLDEFVDWLNE SGCPIQRIADYGDWLQRFETALRALPDRQRHSSLLIPLLHNYRQPERPVRGSIAPTDRFRA AVQEAKIGPDKDIPHVGAPIIVKYVSDLRLLGLL |

FIGURE 9 (continued)

| 3 | *Mycobacterium smegmatis* | ABK71854.1 | MTSDVHDATDGVTETALDDEQSTRRIAELYATDPEFAAAAPLPAVVDAAHKPGLRLAEIL QTLFTGYGDRPALGYRARELATDEGGRTVTRLLPRFDTLTYAQVWSRVQAVAAALRHNFA QPIYPGDAVATIGFASPDYLTLDLVCAYLGLVSVPLQHNAPVSRLAPILAEVEPRILTVS AEYLDLAVESVRDVNSVSQLVVFDHHPEVDOHRDALARAREQLAGKGIAVTTLDAIADEG AGLPAEPIYTADHDQRLAMILYTSGSTGAPKGAMYTEAMVARLWTMSFITGDPTPVINVN FMPLNHLGGRIPISTAVQNGGTSYFVPESDMSTLFEDLALVRPTELGLVPRVADMLYQHH LATVDRLVTQGADELTAEKQAGAELREQVLGGRVITGFVSTAPLAAEMRAFLDITLGAHI VDGYGLTETGAVTRDGVIVRPPVIDYKLIDVPELGYFSTDKPYPRGELLVRSQTLTPGYY KRPEVTASVFDRDGYYHTGDVMAETAPDHLVYDRRNNVLKLAQGEFVAVANLEAVFSGA ALVRQIFVYGNSERSFLLAVVVPTPEALEQYDPAALKAALADSLQRTARDAELQSYEVPA DFIVETEPFSAANGLLSGVGKLLRPNLKDRYGQRLEQMYADIAATQANQLRELRAAATQ PVIDTLTQAAATILGTGSEVASDAHFTDLGGDSLSALTLSNLLSDFFGFEVPVGTIVNPA TNLAQLAQHIEAQRTAGQRRPSFTTVHGADATEIRASELTLDKFIDAETLRAAPGLPKVT TEPRTVLLSGANGWLGRFLTLQWLERLAPVGGTLITIVRGRDDAAARARILTQAYDTDPEL SRRFAELADRHLRVVAGDIGDPNLGLTPEIWHRLAAEVDLVVHPAALVNHVLPYRQLFGP NVVGTAEVIKLALTERIKPVTYLSTVSVAMGIPDFEEDGDIRTVSPVRPLDGGYANGYGN SKWAGEVLLREAHDLCGLPVATFRSDMILAHPRYRGQVNVPDMFTRLLLSLLITGVAPRS FYIGDGERPRAHYPGLTVDFVAEAVTTLGAQQREGYVSYDVMNPHDDGISLDVFVDWLIR AGHPIDRVDDVDDWVRRFETALTALPEKRRAQTVLPLLHAFRAPQAPLRGAPEPTEVFHA AVRTAKVGPGDIPHLDEALIDKYIRDLREFGLI |

FIGURE 9 (continued)

| 4 | Segniliparus rugosus | EFV11917.1 | MGDGEERAKRFFQRIGELSATDPQFAAAAPDPAVVEAVSDPSLSFTRYLDTLMRGYAERP ALAHRVGAGYETISYGELWARVGAIAAAWQADGLAPGDFVATVGFTSPDYVAVDLAAARS GLVSVPLQAGASLAQLVGILEETEPKVLAASASSLEGAVACALAAPSVQRLVVFDLRGPD ASESAADERRGALADAEEQLARAGRAVVVETLADLAARGEALPEAPLFEPAEGEDPLALL IYTSGSTGAPKGAMYSQRLVSQLWGRTPVVPGMPNISLHYMPLSHSYGRAVLAGALSAGG TAHFTANSDLSTLFEDIALARPTFLALVPRVCEMLFQESQRGQDVAELRERVLGGRLLVA VCGSAPLSPEMRAFMEEVLGFPLLDGYGSTEALGVMRNGIIQRPPVIDYKLVDVPELGYR TTDKPYPRGELCIRSTSLISGYYKRPEITAEVFDAQGYYKTGDVMAEIAPDHLVYVDRSK NVLKLSQGEFVAVAKLEAAYGTSPYVKQIFVYGNSERSFLLAVVVPNAEVLGARDQEEAK PLIAASLQKIAKEAGLQSYEVPRDFLIETEPFTTQNGLLSEVGKLLRPKLKARYGEALEA RYDEIAHGQADELRALRDGAGQRPVVETVVRAAVAISGSEGAEVGPEANFADLGGDSLSA LSLANLLHDVFEVEVPVRIIIGPTASLAGIAKHIEAERAGASAPTAASVHGAGATRIRAS ELTLEKFLPEDLLAAAKGLPAADQVRTVLLTGANGWLGRFLALEQLERLARSGQDGGKLI CLVRGKDAAAARRRIEETLGTDPALAARFAELAEGRLEVVPGDVGEPKFGLDDAAWDRLA EEVDVIVHPAALVNHVLPYHQLFGPNVVGTAEIIRLAITAKRKPVTYLSTVAVAAGVEPS SFEEDGDIRAVVPERPLGDGYANGYGNSKWAGEVLLREAHELVGLPVAVFRSDMILAHTR YTGQLNVPDQFTRLVLSLLATGIAPKSFYQQGAAGERQRAHYDGIPVDFTAEAITTLGAE PSWFDGGAGFRSFDVFNPHHDGVGLDEFVDWLIEAGHPISRIDDHKEWFARFETAVRGLP EAQRQHSLLPLLRAYSFPHPPVDGSVYPTGKFQGAVKAAQVGSDHDVPHLGKALIVKYAD DLKALGLL |

FIGURE 9 (continued)

| 5 | Mycobacterium massiliense | EIV11143.1 | MTNETNPQCEQLSRRIESLRESDPQFRAAQPDPAVAEQVLRPGLHLSEAIAALMTGYAER
PALGERARELVIDQDGRTTLRLLPRFDTTTYGELWSRTTSVAAAWHHDATHPVKAGDLVA
TLGFTSIDYTVLDLAIMILGGVAVPLQTSAPASQWTTILAEAEPNTLAVSIELIGAAMES
VRATPSIKQVVVFDYTPEVDDQREAFEAASTQLAGTGIALETLDAVIARGAALPAAPLYA
PSAGDDPLALLIYTSGSTGAPKGAMHSENIVRRWWIREDVMAGTENLPMIGLNFMPMSH
MGRGTLTSTLSTGGTGYFAASSDMSTLFEDMELIRPTALALVPRVCDMVFQRFQTEVDRR
LASGDTASAEAVAAEVKADIRDNLFGGRVSAVMVGSAPLSEELGEFIESCFELNLTDGYG
STEAGMVFRDGIVQRPPVIDYKLVDVPELGYFSTDKPHPRGELLLKTDGMFLGYYKRPEV
TASVFDADGFYMTGDIVAELAHDNIEIIDRRNNVLKLSQGEFVAVATLEAEYANSPVVHQ
IYVYGSSERSYLLAVVVPTPEAVAAAKGDAAALKTTIADSLQDIAKEIQLQSYEVPRDFI
IEPQPFTQGNGLLTGIAKLARPNLKAHYGPRLEQMYAEIAEQQAAELRALHGVDPDKPAL
ETVLKAAQALLGVSSAELAADAHFTDLGGDSLSALSFSDLLRDIFAVEVPVGVVSAAND
LGGVAKFVDEQRHSGGTRPTAETVHGAGHTEIRAADLTLDKFIDEATLHAAPSLPKAAGI
PHTVLLTGSNGYLGHYLALEWLERLDKTDGKLIVIVRGKNAEAAYGRLEEAFDTGDTELL
AHFRSLADKHLEVLAGDIGDPNLGLDADTWQRLADTVDVIVHPAALVNHVLPYNQLFGPN
VVGTAEHIKLAITTKIKPVTYLSTVAVAAYVDPTTFDEESDIRLISAVRPIDDGYANGYG
NAKWAGEVLLREAHDLCGLPVAVFRSDMILAHSRYTGOLNVPDQFTRLILSLIATGIAPG
SFYQAQTTGERPLAHYDGLPGDFTAEAITTLGTQVPEGSEGFVTYDCVNPHADGISLDNF
VDWLIEAGYPIARIDNYTEWFTRFDTAIRGLSEKQCKQHSLLPLLHAFEQPSAAENHGVVP
AKRFQHAVQAAGIGPVGQDGTTTDIPHLSRRLIVKYAKDLEQLGLL |

FIGURE 9 (continued)

| | | |
|---|---|---|
| 6 | Segniliparus rotundus | ADG98140.1 | MTQSHTQGPQASAAHSRLARRAAELLATDPQAAATLPDPEVVRQATRPGLRLAERVDAIL SGYADRPALGQRSFQTVKDPHTGRSSVELLPTFDTITYRELRERATAIASDLAHHPQAPA KPGDFLASIGFISVDYVAIDIAGVFAGLTAVPLQTGATLATLTAITAETAPTLFAASIEH LPTAVDAVILATPSVRRLLVFDYRAGSDEDREAVEAAKRKIADAGSSVLVDVLDEVIARGK SAPKAPLPPATDAGDDSLSLLYTSGSTGTPKGAMYPERNVAHFWGGVWAAAFDEDAAPP VPAINTFLPLSHVASRLSLMPTLARGGLMHFVAKSDLSTLFEDLKLARPTNLFLVPRVV EMLYQHYQSELDRRGVQDGTREAEAVKDDLRTGLLGGRILTAGFGSAPLSAELAGFIESL LQIHLVDGYSGTEAGPVWRDGYLVKPVTDYKLIDVPELGYFSTDSPHPRGELAIKTQTI LPGYYKRPETTAEVFDEDGFYLTGDVVAQIGPEQFAYVDRRKNVLKLSQGEFVTLAKLEA AYSSSPLVRQLFVYGSSERSYLAVIVPTPDALKFGVGEAKAALGESLQKIARDEGLQ SYEVPRDFHETDPFTVENGLLSDARKSLRPKLKEHYGERLEAMYKELADGQANELRDIR RGVCQRPTLETVRRAAAAMLGSASAAEIKPDAHFTDLGGDSLSALTFSNFLHDLFEVDVPV GVIVSAANTLGSVAEHIDACLAGGRARPTFATVHGKGSTTIKASDLTLDKFIDEQTLEAA KHLPKPADPPRTVLLTGANGWLGRFLALEWLERLAPAGGKLITIVRGKDAAQAKARLDAA YESGDPKLAGHYQDLAATTLEVLAGDFSEPRLGLDEATWNRLADEVDFISHPGALVNHVL PYNQLFGPNVAGVAEIIKLAITTRIKPVTYLSTVAVAAGVEPSALDEDGDIRTVSAERSV DEGYANGYGNSKWGGEVLLREAHDRTGLPVRVFRSDMILAHQKYTGQVNATDQFTRLVQS LLATGLAPKSFYELDAQGNRQRAHYDGIPVDFTAESITTLGGDGLEGYRSYNVFNPHRDG VGLDEFVDWLIEAGHPITRIDDYDQWLSRFETSLRGLPESKRQASVLPLLHAFARPGPAV DGSPFRNTVFRTDVQKAKIGAEHDIPHLGKALVLKYADDIKQLGLL |
| 7 | Chromobacterium violaceum | AAQ59697.1 | MQKQRTTSQWRELDAAHHLHPFTDTASLNQAGARVMTRGEGVYLWDSEGNKIIDGMAGLW CVNVGYGRKDFAEAARRQMEELPYNTFFKTTHPAVVELSSLLAEVTPAGFDRVFYTNSG SESVDTMIRMVRRYWDVQGKPEKKTLIGRWNGYHGSTIGGASLGGMKYMHEQGDLPIPGM AHIEQPWWYKHGKDMTPDEFGVVAARWLEEKILEIGADKVAAFVGEPIQGAGGVIVPPAT YWPEIERICRKYDVLLVADEVICGFGRTGEWFGHQHFGFQPDLFTAAKGLSSGYLPIGAV FVGKRVAEGLIAGGDFNHGFTYSGHPVCAAVAHANVAALRDEGIVQRVKDDIGPYMQKRW RETFSRFEHVDDVRGVGMVQAFTLVKNKAKRELFPDFGEIGTLCRDIFFRNNLIMRACGD HIVSAPPLVMTRAEVDEMLAVAERCLEEFEQTLKARGLA |
| 8 | Pseudomonas aeruginosa | AAG08191.1 | MNARLHATSPLGDADLVRADGAHYMHGYHVFDDHRVNGSLNIAAGDGAYIYDTAGNRYLD AVGGMWCTNIGLGREEMARTVAEQTRLLAYSNPFCDMANPRAIELCRKLAELAPGDLDHV FLTTGGSTAVDTAIRLMHYYQNCRGKRAKKHVITRINAYHGSTFLGMSLGGKSADRPAEF DFLDERIHHLACPYYYRAPEGLLGEAEFLDGLVDEFERKILELGADRVGAFISEPVFGSGG VIVPPAGYHRRMWELCQRYDVLYISDEVVTSFGRLGHFASQAVFGVQPDIILTAKGLTS GYQPLGACIFSRRIWEVIAEPDKGRCFSHGFTYSGHPVACAAALKNIEIEREGLLAHAD EVGRYFEERLQSLRDLPIVGDVYRGMRFMACVEFVADKASKALFPESLNIGEWVHLRAQKR GLLVRPIVHLNVMSPPLILTREQVDTVVRVLRESIEETVEDLVRAGHR |

FIGURE 9 (continued)

| | | | |
|---|---|---|---|
| 9 | Pseudomonas syringae | AAY39893.1 | MSANNPQTLEWQALSSEHHLAPFSDYKQLKEKGPRIITRAEGVYLWDSEGNKILDGMSGL WCVAIGYGREELADAASKQMRELPYYNLFFQTAHPPVLELAKAISDIAPEGMNHVFFTGS GSEGNDTMLRMVRHYWALKGQPNKKTIISRVNGYHGSTVAGASLGGMTYMHEQGDLPIPG VVHPQPYWFGEGGDMTPDEFGIWAAEQLEKKILELGVENVGAFIAEPIQGAGGVIVPPD SYWPKKEILSRYDILFAADEVICGFGRTSEWFGSDFYGLRPDMMTIAKGLTSGYVPMGG LIVRDENAVLNEGGDFNHGFTYSGHPVAAAVALENIRILREEKIVERVRSETAPYLCKR LRELSDHPLVGEVRGVGLLGAIELVKDKTTRERYTDKGAGMICRTFCFDNGLIMRAVGDT MIIAPPLVISFAQIDELVEKARTCLDLTLAVLQG |
| 10 | Rhodobacter sphaeroides | ABA81135.1 | MTRNDATNAAGAVGAAMRDHILLPAQEMAKLGKSAQPVLTHAEGIYVHTEDGRRLIDGPA GMWCAQVGYGRREIVDAMAHQAMVLPYASPWYMATSPAARLAEKIATLTPGDINRIFFTT GGSTAVDSALRFSEPYNNVLGRPQKKRIIVRDYGHGSTALTAACTGRTGNWPNFDIAQD RISFLSSPNPRHAGNRSQEAFLDDLVQEFEDRIESLGPDTAAFLAEPILASGGVIIPPA GYHARFKAICEKHDILYISDEVVTGFGRCGEWFASEKVFGVVPDIITFAKGVTSGYVPLG GLAISEAVLARISGENAKGSWFTNGYTYSNQPVACAAALANIELMEREGIVDQAREMADY FAAALASLRDLPGVAEFTRSVGLVGCVQCLLDPTRADGTAEDKAFTLKIDERCFELGLIVR PLGDLCVISPPLISRAQIDEMVAIMRQAITEVSAAHGLTAKEPAAV |
| 11 | Escherichia coli | AAA57874.1 | MNRLPSSASALACSAHALNLIEKRTLDHEEMKALINREVIEYFKEHVNPGFLEYRKSVTAG GDYGAVEWQAGSLNTLVDTQGQEFIDCLGGFGIFNVGHRNPVVVSAVQNQLAKQPLHSQE LLDPLRAMLAKTLAALTPGKLKYSFFCNSGTESVEAALKLAKAYQSPRGKFTFIATSGAF HGKSLGALSATAKSTFRKPFMPLLPGFRHVPGNIEAMRTALNECKKTGDDVAAVILEPI QGEGGVILPPPGYLTAVRKLCDEFGALMILDEVQTGMGRTGKMFACEHENVQPDILCLAK ALGGVMPIGATIATEEVFSVLFDNPFLHTTTFGGNPLACAAALATINVLLEQNLPAGAE QKGDMLLDGFRQLAREYPDLVQEARGKGMLMAIEFVDNEIGYNFASEMFRQRVLVAGTLN NAKTIRIEPPLTLTIEQCELVIKAARKALAAMRVSVEEA |
| 12 | Vibrio Fluvialis | AEA39183.1 | MNKPQSWEARAETYSLYGFTDMPSLHQRGTVVTHGEGPYIVDVNGRRYLDANSGLWNMAV AGFDHKGLIDAAKAQYERFPGYHAFFGRMSDQTVMLSEKLVEVSPFDSGRVFYTNSGSEA NDTMVKMLWFLHAAEGKPQKRKILTRWNAYHGVTAVSASMTGKPYNSVFGLPLPGFVHLT CPHYWRYGEEGETEEQCVARLARELEETIQREGADTIAGFFAEPVMGAGGVIPPAKGYFQ AILPLRKYDIPVISDEVICGFGRTGNTWGCVTYDFTPDAIISSKNLTAGFFPMGAVILG PELSKRLETAIEAIEEFPHGFTASGHPVGCAIALKAIDVVMNEGLAENVRRLAPRFEERL KHIAERPNIGEYRGIGFMWALEAAVKDKASKTPFDGNLSVSERIANTCTDLGLICRPLGQS VVLCPPFILTEAQMDEMFDKLEKALDKVFAEVA |
| 13 | Polaromonas sp. JS666 | ABE47160.1 | MSEAIVVNNQNDCQSRAYAIPLEDIDVSNPELFRDNTMWGYFERLRREDPVHYCKDSLFGP YWSVTKFKDIMQVETHPEIFSSEGNITIMESNAAVTLPMFIAMDPPKHDVQRMAVSPIVA PENLAKLEGLRERTGRALDGLPINETFDWVKLVSINLTTQMLATLFDFPWEDRAKLTRW SDVATALVGTGIDSEEQRMEELKGCVQYMTRLWNERVNVPPGNDLISMIMAHTESMRNMT PEEFLGNLILILVGGNDTTRNSMTGGVLAINENPDEYRKLCANPALIASMVPEIVRWQTP LAHMRRTALQDTELGGKSIRKGDKVIMWVYSGNRDPEAIENPDAFIIDRAKPRHHLSFGF GIHRCVGNRLAELQLRIVWEELLKRWPNPGQHEVVGAPERVLSPVKGYESLPVRINA |

FIGURE 9 (continued)

| | | |
|---|---|---|
| 14 | Mycobacterium sp. HXN-1500 | CAH04396.1 | MTEMTVAASDATNAAYGMALEDIDVSNPVLFRDNTWHPYFKRLREEDPVHYCKSSMFGPY WSVTKYRDIMAVETNPKVFSSEAKSGGITIMDDNAAASLPMFIAMDPPKHDVQRKTVSPI VAPENLATMESVIRQRTADLLDLGLPINEEFDWVHRVSIELTTKMLATLFDFPWDDRAKLT RWSDVTTALPGGGIIDSEEQRMAELMECATYFTELWNQRVNAEPKNDLISMMAHSESTRH MAPEEYLGNIVLLIVGGNDTTRNSMTGGVLALNEFPDEYRKLSANPALISSMVSEIIRWQ TPLSHMRRTALEDIEFGGKHIRQGDKVVMMVVSGNRDPEAIDNPDTFHDRAKPRQHLSF GFGIHRCVGNRLAELQLNLILWEEILKRWPDPLQIQVLQEPTRVLSPFVKGYESLPVRINA |
| 15 | Mycobacterium austroafricanum | ACJ06772.1 | MTEMTVAANDATNAAYGMALEDIDVSNPVLFRDNTWHPYFKRLREEDPVHYCKSSMFGPY WSVTKYRDIMAVETNPKVFSSEAKSGGITIMDDNAAASLPMFIAMDPPKHDVQRKTVSPI VAPENLATMESVIRQRTADLLDLGLPINEEFDWVHRVSIDLTTKMLATLFDFPWDDRAKLT RWSDVTTALPGGGIIDSEEQRMAELMECATYFTELWNQRVNAEPKNDLISMMAHSESTRH MAPEEYLGNIVLLIVGGNDTTRNSMTGGVLALNEFPDEYRKLSANPALISSMVSEIIRWQ TPLSHMRRTALEDIEFGGKHIRQGDKVVMMVVSGNRDPEAIDNPDTFHDRAKPRQHLSF GFGIHRCVGNRLAELQLNLILWEEILKRWPDPLQIQVLQEPTRVLSPFVKGYESLPVRINA |
| 16 | Polaromonas sp. JS666 | ABE47159.1 | MSETVIIAGAGQAAGGQAVASLRQEGFDGRIVLVGAEPVLPYQRPPLSKAFLAGTLPLERL FLKPPAFYEQARVDTLLGVAVTTELDAARRQVRLDDGRELAFDHLLLATGGRARRLDCPGA DHPRLHYLRTVADVDGIRAALRPGARLVLIGSGYVGLEIAAVAAKLGLAVTVLEAAPTVL ARVTCPAVARFFESVHROAGVTIRCATTVSGIEGDASLARVVTGDGERIDADLVIAGIGL LPNVELAQAAGLVCDNGIVVDEECRTSVPGIFAAGDCTQHPNAIYDSRLRESVHNAIEQ GKTAAAAMCGKARPYRQVVMFWSDQYDLKLQTAGLNRGYDQVVMRGSTDNRSFAAFYLRD GRLLAVDAVNRPVEFMVAKALIANRTVIAPERLADERIAAKDLAG |
| 17 | Mycobacterium sp. HXN-1500 | CAH04397.1 | MIHTGVITEAVVVGAGQAGQTVTSLRQRGFEGQITLLGDEPALPYQRPPLSKAFLAGTIL PLDRLYLRPAAFYQQAHVDVMVDTGVSELDTENRRIRLTDGRAISFDHLVLATGGRPRPL ACPGADHPRVHYLRTVTDVDRIRSQFHPGTRLVLVGGGYIGLEIAAVAAELGLTVTVLEA QITVLARVTCPTVARFFEHTHRRAGVTIRCATTVTRIHDSSSTARIELDSGEYIDADLVI VGIGLLPNVDLASAAGLTCESGIVVDSRCQTSAPGIYAAGDCTQYPSPIYGRPLHLESVH NAIEQAKTAAAAILGRDEPFFRQVPWFWSDQYNIKLQTAGVNEGYDDVIIRGDPASASFAA FYLRAGKLLAVDAINRPREFMASKTLIAERAEVDPTQLADESLPPTALAAAVNGPTRATS PTSL |
| 18 | Polaromonas sp. JS666 | ABE47158.1 | MTKVTFIEHNGTVRNVDVDDGLSVMEAAVNNLVPGIDGDCGGACACATCHVHIDAAWLDK LPPMEAMEKSMLEFAEGRNESSRLGCQIKLSPALDGIVVRTPLGQH |
| 19 | Mycobacterium sp. HXN-1500 | CAH04398.1 | MPKITYIDYTGTSRCVDAENGMSLMEIAINNVPGIDGDCGGECACATCHVHVDADWLDK LPPSSDQEVSMLEFCDGVDHTSRLGCQIKICPTLDGIVVRTPAAQH |
| 20 | Bacillus subtilis | CAA44858.1 | MKIYGIYMDRPLSQEENERFMSFISPEKREKCRRFYHKEDAHRTLLGDVLVRSVISRQYQ LDKSDIRFSTQEYGKPCIPDLPDAHFNISHSGRWVICAFDSQPIGIDIEKTKPISLEIAK RFFSKTEYSDLLAKDKDEQTDYFYHLWSMKESFKQEGKGLSLPLDSFSVRLHQDGQVSI ELPDSHSPCYIKTYEVDPGYKMAVCAAHPFPEDITMVSYEELL |

FIGURE 9 (continued)

| 21 | Nocardia sp. NRRL 5646 | ABI83656.1 | MIETILPAGVESAELLEYPEDLKAHPAEEHLIAKSVEKRRDFIGARHCARLALAELGEP PVAIGKGERGAPIWPRGVVGSLTHCDGYRAAAVAHKMRFRSIGIDAEPHATLPEGVLDSV SLPPEREWLKTTDSALHLDRLLFCAKEATYKAWWPLTARWLGFEEAHITFEIEDGSADSG NGTFHSELLVPGQTNDGGTPLLSFDGRWLIADGFILTAIAYA |

SEQUENCE LISTING

<160> NUMBER OF SEQ ID NOS: 21

<210> SEQ ID NO 1
<211> LENGTH: 286
<212> TYPE: PRT
<213> ORGANISM: Escherichia coli

<400> SEQUENCE: 1

Met Ser Gln Ala Leu Lys Asn Leu Leu Thr Leu Leu Asn Leu Glu Lys
1               5                   10                  15

Ile Glu Glu Gly Leu Phe Arg Gly Gln Ser Glu Asp Leu Gly Leu Arg
            20                  25                  30

Gln Val Phe Gly Gly Gln Val Val Gly Gln Ala Leu Tyr Ala Ala Lys
        35                  40                  45

-continued

```
Glu Thr Val Pro Glu Glu Arg Leu Val His Ser Phe His Ser Tyr Phe
    50                  55                  60

Leu Arg Pro Gly Asp Ser Lys Lys Pro Ile Ile Tyr Asp Val Glu Thr
65                  70                  75                  80

Leu Arg Asp Gly Asn Ser Phe Ser Ala Arg Arg Val Ala Ala Ile Gln
                85                  90                  95

Asn Gly Lys Pro Ile Phe Tyr Met Thr Ala Ser Phe Gln Ala Pro Glu
            100                 105                 110

Ala Gly Phe Glu His Gln Lys Thr Met Pro Ser Ala Pro Ala Pro Asp
        115                 120                 125

Gly Leu Pro Ser Glu Thr Gln Ile Ala Gln Ser Leu Ala His Leu Leu
    130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
                165                 170                 175

His Arg Gln Val Trp Ile Arg Ala Asn Gly Ser Val Pro Asp Asp Leu
            180                 185                 190

Arg Val His Gln Tyr Leu Leu Gly Tyr Ala Ser Asp Leu Asn Phe Leu
        195                 200                 205

Pro Val Ala Leu Gln Pro His Gly Ile Gly Phe Leu Glu Pro Gly Ile
    210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
                245                 250                 255

Ala Arg Gly Phe Val Arg Gly Glu Phe Tyr Thr Gln Asp Gly Val Leu
            260                 265                 270

Val Ala Ser Thr Val Gln Glu Gly Val Met Arg Asn His Asn
        275                 280                 285
```

<210> SEQ ID NO 2
<211> LENGTH: 1174
<212> TYPE: PRT
<213> ORGANISM: Mycobacterium marinum

<400> SEQUENCE: 2

```
Met Ser Pro Ile Thr Arg Glu Glu Arg Leu Glu Arg Arg Ile Gln Asp
 1               5                  10                  15

Leu Tyr Ala Asn Asp Pro Gln Phe Ala Ala Ala Lys Pro Ala Thr Ala
            20                  25                  30

Ile Thr Ala Ala Ile Glu Arg Pro Gly Leu Pro Leu Pro Gln Ile Ile
        35                  40                  45

Glu Thr Val Met Thr Gly Tyr Ala Asp Arg Pro Ala Leu Ala Gln Arg
    50                  55                  60

Ser Val Glu Phe Val Thr Asp Ala Gly Thr Gly His Thr Thr Leu Arg
65                  70                  75                  80

Leu Leu Pro His Phe Glu Thr Ile Ser Tyr Gly Glu Leu Trp Asp Arg
                85                  90                  95

Ile Ser Ala Leu Ala Asp Val Leu Ser Thr Glu Gln Thr Val Lys Pro
            100                 105                 110

Gly Asp Arg Val Cys Leu Leu Gly Phe Asn Ser Val Asp Tyr Ala Thr
        115                 120                 125

Ile Asp Met Thr Leu Ala Arg Leu Gly Ala Val Ala Val Pro Leu Gln
    130                 135                 140
```

```
Thr Ser Ala Ala Ile Thr Gln Leu Gln Pro Ile Val Ala Glu Thr Gln
145                 150                 155                 160

Pro Thr Met Ile Ala Ala Ser Val Asp Ala Leu Ala Asp Ala Thr Glu
            165                 170                 175

Leu Ala Leu Ser Gly Gln Thr Ala Thr Arg Val Leu Val Phe Asp His
            180                 185                 190

His Arg Gln Val Asp Ala His Arg Ala Ala Val Glu Ser Ala Arg Glu
            195                 200                 205

Arg Leu Ala Gly Ser Ala Val Val Glu Thr Leu Ala Glu Ala Ile Ala
210                 215                 220

Arg Gly Asp Val Pro Arg Gly Ala Ser Ala Gly Ser Ala Pro Gly Thr
225                 230                 235                 240

Asp Val Ser Asp Asp Ser Leu Ala Leu Leu Ile Tyr Thr Ser Gly Ser
                245                 250                 255

Thr Gly Ala Pro Lys Gly Ala Met Tyr Pro Arg Arg Asn Val Ala Thr
            260                 265                 270

Phe Trp Arg Lys Arg Thr Trp Phe Glu Gly Gly Tyr Glu Pro Ser Ile
            275                 280                 285

Thr Leu Asn Phe Met Pro Met Ser His Val Met Gly Arg Gln Ile Leu
290                 295                 300

Tyr Gly Thr Leu Cys Asn Gly Gly Thr Ala Tyr Phe Val Ala Lys Ser
305                 310                 315                 320

Asp Leu Ser Thr Leu Phe Glu Asp Leu Ala Leu Val Arg Pro Thr Glu
                325                 330                 335

Leu Thr Phe Val Pro Arg Val Trp Asp Met Val Phe Asp Glu Phe Gln
            340                 345                 350

Ser Glu Val Asp Arg Arg Leu Val Asp Gly Ala Asp Arg Val Ala Leu
            355                 360                 365

Glu Ala Gln Val Lys Ala Glu Ile Arg Asn Asp Val Leu Gly Gly Arg
370                 375                 380

Tyr Thr Ser Ala Leu Thr Gly Ser Ala Pro Ile Ser Asp Glu Met Lys
385                 390                 395                 400

Ala Trp Val Glu Glu Leu Leu Asp Met His Leu Val Glu Gly Tyr Gly
                405                 410                 415

Ser Thr Glu Ala Gly Met Ile Leu Ile Asp Gly Ala Ile Arg Arg Pro
            420                 425                 430

Ala Val Leu Asp Tyr Lys Leu Val Asp Val Pro Asp Leu Gly Tyr Phe
            435                 440                 445

Leu Thr Asp Arg Pro His Pro Arg Gly Glu Leu Leu Val Lys Thr Asp
450                 455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
                485                 490                 495

Gly Pro Glu Gln Phe Val Tyr Leu Asp Arg Arg Asn Asn Val Leu Lys
            500                 505                 510

Leu Ser Gln Gly Glu Phe Val Thr Val Ser Lys Leu Glu Ala Val Phe
            515                 520                 525

Gly Asp Ser Pro Leu Val Arg Gln Ile Tyr Ile Tyr Gly Asn Ser Ala
530                 535                 540

Arg Ala Tyr Leu Leu Ala Val Ile Val Pro Thr Gln Glu Ala Leu Asp
545                 550                 555                 560
```

```
Ala Val Pro Val Glu Glu Leu Lys Ala Arg Leu Gly Asp Ser Leu Gln
            565                 570                 575
Glu Val Ala Lys Ala Ala Gly Leu Gln Ser Tyr Glu Ile Pro Arg Asp
            580                 585                 590
Phe Ile Ile Glu Thr Thr Pro Trp Thr Leu Glu Asn Gly Leu Leu Thr
            595                 600                 605
Gly Ile Arg Lys Leu Ala Arg Pro Gln Leu Lys Lys His Tyr Gly Glu
        610                 615                 620
Leu Leu Glu Gln Ile Tyr Thr Asp Leu Ala His Gly Gln Ala Asp Glu
625                 630                 635                 640
Leu Arg Ser Leu Arg Gln Ser Gly Ala Asp Ala Pro Val Leu Val Thr
                645                 650                 655
Val Cys Arg Ala Ala Ala Ala Leu Leu Gly Gly Ser Ala Ser Asp Val
            660                 665                 670
Gln Pro Asp Ala His Phe Thr Asp Leu Gly Gly Asp Ser Leu Ser Ala
            675                 680                 685
Leu Ser Phe Thr Asn Leu Leu His Glu Ile Phe Asp Ile Glu Val Pro
        690                 695                 700
Val Gly Val Ile Val Ser Pro Ala Asn Asp Leu Gln Ala Leu Ala Asp
705                 710                 715                 720
Tyr Val Glu Ala Ala Arg Lys Pro Gly Ser Ser Arg Pro Thr Phe Ala
                725                 730                 735
Ser Val His Gly Ala Ser Asn Gly Gln Val Thr Glu Val His Ala Gly
            740                 745                 750
Asp Leu Ser Leu Asp Lys Phe Ile Asp Ala Ala Thr Leu Ala Glu Ala
            755                 760                 765
Pro Arg Leu Pro Ala Ala Asn Thr Gln Val Arg Thr Val Leu Leu Thr
        770                 775                 780
Gly Ala Thr Gly Phe Leu Gly Arg Tyr Leu Ala Leu Glu Trp Leu Glu
785                 790                 795                 800
Arg Met Asp Leu Val Asp Gly Lys Leu Ile Cys Leu Val Arg Ala Lys
                805                 810                 815
Ser Asp Thr Glu Ala Arg Ala Arg Leu Asp Lys Thr Phe Asp Ser Gly
            820                 825                 830
Asp Pro Glu Leu Leu Ala His Tyr Arg Ala Leu Ala Gly Asp His Leu
            835                 840                 845
Glu Val Leu Ala Gly Asp Lys Gly Glu Ala Asp Leu Gly Leu Asp Arg
        850                 855                 860
Gln Thr Trp Gln Arg Leu Ala Asp Thr Val Asp Leu Ile Val Asp Pro
865                 870                 875                 880
Ala Ala Leu Val Asn His Val Leu Pro Tyr Ser Gln Leu Phe Gly Pro
                885                 890                 895
Asn Ala Leu Gly Thr Ala Glu Leu Leu Arg Leu Ala Leu Thr Ser Lys
            900                 905                 910
Ile Lys Pro Tyr Ser Tyr Thr Ser Thr Ile Gly Val Ala Asp Gln Ile
            915                 920                 925
Pro Pro Ser Ala Phe Thr Glu Asp Ala Asp Ile Arg Val Ile Ser Ala
        930                 935                 940
Thr Arg Ala Val Asp Asp Ser Tyr Ala Asn Gly Tyr Ser Asn Ser Lys
945                 950                 955                 960
Trp Ala Gly Glu Val Leu Leu Arg Glu Ala His Asp Leu Cys Gly Leu
                965                 970                 975
Pro Val Ala Val Phe Arg Cys Asp Met Ile Leu Ala Asp Thr Thr Trp
```

```
                980             985             990
Ala Gly Gln Leu Asn Val Pro Asp Met Phe Thr Arg Met Ile Leu Ser
            995                 1000                1005

Leu Ala Ala Thr Gly Ile Ala Pro Gly Ser Phe Tyr Glu Leu Ala Ala
        1010                1015                1020

Asp Gly Ala Arg Gln Arg Ala His Tyr Asp Gly Leu Pro Val Glu Phe
1025                1030                1035                1040

Ile Ala Glu Ala Ile Ser Thr Leu Gly Ala Gln Ser Gln Asp Gly Phe
                1045                1050                1055

His Thr Tyr His Val Met Asn Pro Tyr Asp Gly Ile Gly Leu Asp
            1060                1065                1070

Glu Phe Val Asp Trp Leu Asn Glu Ser Gly Cys Pro Ile Gln Arg Ile
        1075                1080                1085

Ala Asp Tyr Gly Asp Trp Leu Gln Arg Phe Glu Thr Ala Leu Arg Ala
        1090                1095                1100

Leu Pro Asp Arg Gln Arg His Ser Ser Leu Leu Pro Leu His Asn
1105                1110                1115                1120

Tyr Arg Gln Pro Glu Arg Pro Val Arg Gly Ser Ile Ala Pro Thr Asp
                1125                1130                1135

Arg Phe Arg Ala Ala Val Gln Glu Ala Lys Ile Gly Pro Asp Lys Asp
        1140                1145                1150

Ile Pro His Val Gly Ala Pro Ile Ile Val Lys Tyr Val Ser Asp Leu
        1155                1160                1165

Arg Leu Leu Gly Leu Leu
        1170

<210> SEQ ID NO 3
<211> LENGTH: 1173
<212> TYPE: PRT
<213> ORGANISM: Mycobacterium smegmatis

<400> SEQUENCE: 3

Met Thr Ser Asp Val His Asp Ala Thr Asp Gly Val Thr Glu Thr Ala
 1               5                  10                  15

Leu Asp Asp Glu Gln Ser Thr Arg Arg Ile Ala Glu Leu Tyr Ala Thr
            20                  25                  30

Asp Pro Glu Phe Ala Ala Ala Pro Leu Pro Ala Val Val Asp Ala
        35                  40                  45

Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175
```

```
Leu Thr Val Ser Ala Glu Tyr Leu Asp Leu Ala Val Glu Ser Val Arg
                180                 185                 190

Asp Val Asn Ser Val Ser Gln Leu Val Val Phe Asp His His Pro Glu
            195                 200                 205

Val Asp Asp His Arg Asp Ala Leu Ala Arg Ala Arg Glu Gln Leu Ala
        210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255

Leu Ala Met Ile Leu Tyr Thr Ser Gly Ser Thr Gly Ala Pro Lys Gly
            260                 265                 270

Ala Met Tyr Thr Glu Ala Met Val Ala Arg Leu Trp Thr Met Ser Phe
        275                 280                 285

Ile Thr Gly Asp Pro Thr Pro Val Ile Asn Val Asn Phe Met Pro Leu
290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
        355                 360                 365

Thr Gln Gly Ala Asp Glu Leu Thr Ala Glu Lys Gln Ala Gly Ala Glu
370                 375                 380

Leu Arg Glu Gln Val Leu Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415

Gly Ala His Ile Val Asp Gly Tyr Gly Leu Thr Glu Thr Gly Ala Val
            420                 425                 430

Thr Arg Asp Gly Val Ile Val Arg Pro Pro Val Ile Asp Tyr Lys Leu
        435                 440                 445

Ile Asp Val Pro Glu Leu Gly Tyr Phe Ser Thr Asp Lys Pro Tyr Pro
450                 455                 460

Arg Gly Glu Leu Leu Val Arg Ser Gln Thr Leu Thr Pro Gly Tyr Tyr
465                 470                 475                 480

Lys Arg Pro Glu Val Thr Ala Ser Val Phe Asp Arg Asp Gly Tyr Tyr
                485                 490                 495

His Thr Gly Asp Val Met Ala Glu Thr Ala Pro Asp His Leu Val Tyr
            500                 505                 510

Val Asp Arg Arg Asn Asn Val Leu Lys Leu Ala Gln Gly Glu Phe Val
        515                 520                 525

Ala Val Ala Asn Leu Glu Ala Val Phe Ser Gly Ala Ala Leu Val Arg
530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                565                 570                 575

Lys Ala Ala Leu Ala Asp Ser Leu Gln Arg Thr Ala Arg Asp Ala Glu
            580                 585                 590

Leu Gln Ser Tyr Glu Val Pro Ala Asp Phe Ile Val Glu Thr Glu Pro
```

```
                    595                 600                 605
        Phe Ser Ala Ala Asn Gly Leu Leu Ser Gly Val Gly Lys Leu Leu Arg
            610                 615                 620

Pro Asn Leu Lys Asp Arg Tyr Gly Gln Arg Leu Glu Gln Met Tyr Ala
        625                 630                 635                 640

Asp Ile Ala Ala Thr Gln Ala Asn Gln Leu Arg Glu Leu Arg Arg Ala
                        645                 650                 655

Ala Ala Thr Gln Pro Val Ile Asp Thr Leu Thr Gln Ala Ala Ala Thr
                    660                 665                 670

Ile Leu Gly Thr Gly Ser Glu Val Ala Ser Asp Ala His Phe Thr Asp
                675                 680                 685

Leu Gly Gly Asp Ser Leu Ser Ala Leu Thr Leu Ser Asn Leu Leu Ser
            690                 695                 700

Asp Phe Phe Gly Phe Glu Val Pro Val Gly Thr Ile Val Asn Pro Ala
        705                 710                 715                 720

Thr Asn Leu Ala Gln Leu Ala Gln His Ile Glu Ala Gln Arg Thr Ala
                        725                 730                 735

Gly Asp Arg Arg Pro Ser Phe Thr Thr Val His Gly Ala Asp Ala Thr
                    740                 745                 750

Glu Ile Arg Ala Ser Glu Leu Thr Leu Asp Lys Phe Ile Asp Ala Glu
                755                 760                 765

Thr Leu Arg Ala Ala Pro Gly Leu Pro Lys Val Thr Thr Glu Pro Arg
            770                 775                 780

Thr Val Leu Leu Ser Gly Ala Asn Gly Trp Leu Gly Arg Phe Leu Thr
        785                 790                 795                 800

Leu Gln Trp Leu Glu Arg Leu Ala Pro Val Gly Gly Thr Leu Ile Thr
                        805                 810                 815

Ile Val Arg Gly Arg Asp Asp Ala Ala Ala Arg Ala Arg Leu Thr Gln
                    820                 825                 830

Ala Tyr Asp Thr Asp Pro Glu Leu Ser Arg Arg Phe Ala Glu Leu Ala
                835                 840                 845

Asp Arg His Leu Arg Val Val Ala Gly Asp Ile Gly Asp Pro Asn Leu
            850                 855                 860

Gly Leu Thr Pro Glu Ile Trp His Arg Leu Ala Ala Glu Val Asp Leu
        865                 870                 875                 880

Val Val His Pro Ala Ala Leu Val Asn His Val Leu Pro Tyr Arg Gln
                        885                 890                 895

Leu Phe Gly Pro Asn Val Val Gly Thr Ala Glu Val Ile Lys Leu Ala
                    900                 905                 910

Leu Thr Glu Arg Ile Lys Pro Val Thr Tyr Leu Ser Thr Val Ser Val
                915                 920                 925

Ala Met Gly Ile Pro Asp Phe Glu Glu Asp Gly Asp Ile Arg Thr Val
            930                 935                 940

Ser Pro Val Arg Pro Leu Asp Gly Gly Tyr Ala Asn Gly Tyr Gly Asn
        945                 950                 955                 960

Ser Lys Trp Ala Gly Glu Val Leu Leu Arg Glu Ala His Asp Leu Cys
                        965                 970                 975

Gly Leu Pro Val Ala Thr Phe Arg Ser Asp Met Ile Leu Ala His Pro
                    980                 985                 990

Arg Tyr Arg Gly Gln Val Asn Val Pro Asp Met Phe Thr Arg Leu Leu
                995                 1000                1005

Leu Ser Leu Leu Ile Thr Gly Val Ala Pro Arg Ser Phe Tyr Ile Gly
            1010                1015                1020
```

```
Asp Gly Glu Arg Pro Arg Ala His Tyr Pro Gly Leu Thr Val Asp Phe
1025                1030                1035                1040

Val Ala Glu Ala Val Thr Thr Leu Gly Ala Gln Gln Arg Glu Gly Tyr
            1045                1050                1055

Val Ser Tyr Asp Val Met Asn Pro His Asp Asp Gly Ile Ser Leu Asp
        1060                1065                1070

Val Phe Val Asp Trp Leu Ile Arg Ala Gly His Pro Ile Asp Arg Val
    1075                1080                1085

Asp Asp Tyr Asp Asp Trp Val Arg Arg Phe Glu Thr Ala Leu Thr Ala
1090                1095                1100

Leu Pro Glu Lys Arg Arg Ala Gln Thr Val Leu Pro Leu Leu His Ala
1105                1110                1115                1120

Phe Arg Ala Pro Gln Ala Pro Leu Arg Gly Ala Pro Glu Pro Thr Glu
                1125                1130                1135

Val Phe His Ala Ala Val Arg Thr Ala Lys Val Gly Pro Gly Asp Ile
            1140                1145                1150

Pro His Leu Asp Glu Ala Leu Ile Asp Lys Tyr Ile Arg Asp Leu Arg
        1155                1160                1165

Glu Phe Gly Leu Ile
    1170

<210> SEQ ID NO 4
<211> LENGTH: 1148
<212> TYPE: PRT
<213> ORGANISM: Segniliparus rugosus

<400> SEQUENCE: 4

Met Gly Asp Gly Glu Glu Arg Ala Lys Arg Phe Phe Gln Arg Ile Gly
1               5                   10                  15

Glu Leu Ser Ala Thr Asp Pro Gln Phe Ala Ala Ala Pro Asp Pro
            20                  25                  30

Ala Val Val Glu Ala Val Ser Asp Pro Ser Leu Ser Phe Thr Arg Tyr
        35                  40                  45

Leu Asp Thr Leu Met Arg Gly Tyr Ala Glu Arg Pro Ala Leu Ala His
    50                  55                  60

Arg Val Gly Ala Gly Tyr Glu Thr Ile Ser Tyr Gly Glu Leu Trp Ala
65                  70                  75                  80

Arg Val Gly Ala Ile Ala Ala Trp Gln Ala Asp Gly Leu Ala Pro
                85                  90                  95

Gly Asp Phe Val Ala Thr Val Gly Phe Thr Ser Pro Asp Tyr Val Ala
            100                 105                 110

Val Asp Leu Ala Ala Ala Arg Ser Gly Leu Val Ser Val Pro Leu Gln
        115                 120                 125

Ala Gly Ala Ser Leu Ala Gln Leu Val Gly Ile Leu Glu Glu Thr Glu
    130                 135                 140

Pro Lys Val Leu Ala Ala Ser Ala Ser Ser Leu Glu Gly Ala Val Ala
145                 150                 155                 160

Cys Ala Leu Ala Ala Pro Ser Val Gln Arg Leu Val Val Phe Asp Leu
                165                 170                 175

Arg Gly Pro Asp Ala Ser Glu Ser Ala Ala Asp Glu Arg Arg Gly Ala
            180                 185                 190

Leu Ala Asp Ala Glu Glu Gln Leu Ala Arg Ala Gly Arg Ala Val Val
        195                 200                 205

Val Glu Thr Leu Ala Asp Leu Ala Ala Arg Gly Glu Ala Leu Pro Glu
```

```
            210                 215                 220
Ala Pro Leu Phe Glu Pro Ala Glu Gly Glu Asp Pro Leu Ala Leu Leu
225                 230                 235                 240

Ile Tyr Thr Ser Gly Ser Thr Gly Ala Pro Lys Gly Ala Met Tyr Ser
                245                 250                 255

Gln Arg Leu Val Ser Gln Leu Trp Gly Arg Thr Pro Val Val Pro Gly
            260                 265                 270

Met Pro Asn Ile Ser Leu His Tyr Met Pro Leu Ser His Ser Tyr Gly
            275                 280                 285

Arg Ala Val Leu Ala Gly Ala Leu Ser Ala Gly Gly Thr Ala His Phe
            290                 295                 300

Thr Ala Asn Ser Asp Leu Ser Thr Leu Phe Glu Asp Ile Ala Leu Ala
305                 310                 315                 320

Arg Pro Thr Phe Leu Ala Leu Val Pro Arg Val Cys Glu Met Leu Phe
                325                 330                 335

Gln Glu Ser Gln Arg Gly Gln Asp Val Ala Glu Leu Arg Glu Arg Val
            340                 345                 350

Leu Gly Gly Arg Leu Leu Val Ala Val Cys Gly Ser Ala Pro Leu Ser
            355                 360                 365

Pro Glu Met Arg Ala Phe Met Glu Glu Val Leu Gly Phe Pro Leu Leu
            370                 375                 380

Asp Gly Tyr Gly Ser Thr Glu Ala Leu Gly Val Met Arg Asn Gly Ile
385                 390                 395                 400

Ile Gln Arg Pro Pro Val Ile Asp Tyr Lys Leu Val Asp Val Pro Glu
                405                 410                 415

Leu Gly Tyr Arg Thr Thr Asp Lys Pro Tyr Pro Arg Gly Glu Leu Cys
            420                 425                 430

Ile Arg Ser Thr Ser Leu Ile Ser Gly Tyr Tyr Lys Arg Pro Glu Ile
            435                 440                 445

Thr Ala Glu Val Phe Asp Ala Gln Gly Tyr Tyr Lys Thr Gly Asp Val
            450                 455                 460

Met Ala Glu Ile Ala Pro Asp His Leu Val Tyr Val Asp Arg Ser Lys
465                 470                 475                 480

Asn Val Leu Lys Leu Ser Gln Gly Glu Phe Val Ala Val Ala Lys Leu
                485                 490                 495

Glu Ala Ala Tyr Gly Thr Ser Pro Tyr Val Lys Gln Ile Phe Val Tyr
            500                 505                 510

Gly Asn Ser Glu Arg Ser Phe Leu Leu Ala Val Val Val Pro Asn Ala
            515                 520                 525

Glu Val Leu Gly Ala Arg Asp Gln Glu Glu Ala Lys Pro Leu Ile Ala
            530                 535                 540

Ala Ser Leu Gln Lys Ile Ala Lys Glu Ala Gly Leu Gln Ser Tyr Glu
545                 550                 555                 560

Val Pro Arg Asp Phe Leu Ile Glu Thr Glu Pro Phe Thr Thr Gln Asn
                565                 570                 575

Gly Leu Leu Ser Glu Val Gly Lys Leu Leu Arg Pro Lys Leu Lys Ala
            580                 585                 590

Arg Tyr Gly Glu Ala Leu Glu Ala Arg Tyr Asp Glu Ile Ala His Gly
            595                 600                 605

Gln Ala Asp Glu Leu Arg Ala Leu Arg Asp Gly Ala Gly Gln Arg Pro
            610                 615                 620

Val Val Glu Thr Val Val Arg Ala Ala Val Ala Ile Ser Gly Ser Glu
625                 630                 635                 640
```

```
Gly Ala Glu Val Gly Pro Glu Ala Asn Phe Ala Asp Leu Gly Gly Asp
                645                 650                 655
Ser Leu Ser Ala Leu Ser Leu Ala Asn Leu Leu His Asp Val Phe Glu
            660                 665                 670
Val Glu Val Pro Val Arg Ile Ile Ile Gly Pro Thr Ala Ser Leu Ala
        675                 680                 685
Gly Ile Ala Lys His Ile Glu Ala Glu Arg Ala Gly Ala Ser Ala Pro
    690                 695                 700
Thr Ala Ala Ser Val His Gly Ala Gly Ala Thr Arg Ile Arg Ala Ser
705                 710                 715                 720
Glu Leu Thr Leu Glu Lys Phe Leu Pro Glu Asp Leu Ala Ala Ala
                725                 730                 735
Lys Gly Leu Pro Ala Ala Asp Gln Val Arg Thr Val Leu Leu Thr Gly
            740                 745                 750
Ala Asn Gly Trp Leu Gly Arg Phe Leu Ala Leu Glu Gln Leu Glu Arg
        755                 760                 765
Leu Ala Arg Ser Gly Gln Asp Gly Gly Lys Leu Ile Cys Leu Val Arg
    770                 775                 780
Gly Lys Asp Ala Ala Ala Arg Arg Ile Glu Glu Thr Leu Gly
785                 790                 795                 800
Thr Asp Pro Ala Leu Ala Arg Phe Ala Glu Leu Ala Glu Gly Arg
                805                 810                 815
Leu Glu Val Val Pro Gly Asp Val Gly Glu Pro Lys Phe Gly Leu Asp
            820                 825                 830
Asp Ala Ala Trp Asp Arg Leu Ala Glu Glu Val Asp Val Ile Val His
        835                 840                 845
Pro Ala Ala Leu Val Asn His Val Leu Pro Tyr His Gln Leu Phe Gly
    850                 855                 860
Pro Asn Val Val Gly Thr Ala Glu Ile Ile Arg Leu Ala Ile Thr Ala
865                 870                 875                 880
Lys Arg Lys Pro Val Thr Tyr Leu Ser Thr Val Ala Val Ala Ala Gly
                885                 890                 895
Val Glu Pro Ser Ser Phe Glu Glu Asp Gly Asp Ile Arg Ala Val Val
            900                 905                 910
Pro Glu Arg Pro Leu Gly Asp Gly Tyr Ala Asn Gly Tyr Gly Asn Ser
        915                 920                 925
Lys Trp Ala Gly Glu Val Leu Leu Arg Glu Ala His Glu Leu Val Gly
    930                 935                 940
Leu Pro Val Ala Val Phe Arg Ser Asp Met Ile Leu Ala His Thr Arg
945                 950                 955                 960
Tyr Thr Gly Gln Leu Asn Val Pro Asp Gln Phe Thr Arg Leu Val Leu
                965                 970                 975
Ser Leu Leu Ala Thr Gly Ile Ala Pro Lys Ser Phe Tyr Gln Gln Gly
            980                 985                 990
Ala Ala Gly Glu Arg Gln Arg Ala His Tyr Asp Gly Ile Pro Val Asp
        995                 1000                1005
Phe Thr Ala Glu Ala Ile Thr Thr Leu Gly Ala Glu Pro Ser Trp Phe
    1010                1015                1020
Asp Gly Gly Ala Gly Phe Arg Ser Phe Asp Val Phe Asn Pro His His
1025                1030                1035                1040
Asp Gly Val Gly Leu Asp Glu Phe Val Asp Trp Leu Ile Glu Ala Gly
                1045                1050                1055
```

His Pro Ile Ser Arg Ile Asp Asp His Lys Glu Trp Phe Ala Arg Phe
                1060                1065                1070

Glu Thr Ala Val Arg Gly Leu Pro Glu Ala Gln Arg Gln His Ser Leu
            1075                1080                1085

Leu Pro Leu Leu Arg Ala Tyr Ser Phe Pro His Pro Val Asp Gly
        1090                1095                1100

Ser Val Tyr Pro Thr Gly Lys Phe Gln Gly Ala Val Lys Ala Gln
1105                1110                1115                1120

Val Gly Ser Asp His Asp Val Pro His Leu Gly Lys Ala Leu Ile Val
                1125                1130                1135

Lys Tyr Ala Asp Asp Leu Lys Ala Leu Gly Leu Leu
            1140                1145

<210> SEQ ID NO 5
<211> LENGTH: 1185
<212> TYPE: PRT
<213> ORGANISM: Mycobacterium massiliense

<400> SEQUENCE: 5

Met Thr Asn Glu Thr Asn Pro Gln Gln Glu Gln Leu Ser Arg Arg Ile
1               5                   10                  15

Glu Ser Leu Arg Glu Ser Asp Pro Gln Phe Arg Ala Ala Gln Pro Asp
            20                  25                  30

Pro Ala Val Ala Glu Gln Val Leu Arg Pro Gly Leu His Leu Ser Glu
        35                  40                  45

Ala Ile Ala Ala Leu Met Thr Gly Tyr Ala Glu Arg Pro Ala Leu Gly
    50                  55                  60

Glu Arg Ala Arg Glu Leu Val Ile Asp Gln Asp Gly Arg Thr Thr Leu
65                  70                  75                  80

Arg Leu Leu Pro Arg Phe Asp Thr Thr Thr Tyr Gly Glu Leu Trp Ser
                85                  90                  95

Arg Thr Thr Ser Val Ala Ala Ala Trp His His Asp Ala Thr His Pro
            100                 105                 110

Val Lys Ala Gly Asp Leu Val Ala Thr Leu Gly Phe Thr Ser Ile Asp
        115                 120                 125

Tyr Thr Val Leu Asp Leu Ala Ile Met Ile Leu Gly Gly Val Ala Val
    130                 135                 140

Pro Leu Gln Thr Ser Ala Pro Ala Ser Gln Trp Thr Thr Ile Leu Ala
145                 150                 155                 160

Glu Ala Glu Pro Asn Thr Leu Ala Val Ser Ile Glu Leu Ile Gly Ala
                165                 170                 175

Ala Met Glu Ser Val Arg Ala Thr Pro Ser Ile Lys Gln Val Val Val
            180                 185                 190

Phe Asp Tyr Thr Pro Glu Val Asp Asp Gln Arg Glu Ala Phe Glu Ala
        195                 200                 205

Ala Ser Thr Gln Leu Ala Gly Thr Gly Ile Ala Leu Glu Thr Leu Asp
    210                 215                 220

Ala Val Ile Ala Arg Gly Ala Ala Leu Pro Ala Ala Pro Leu Tyr Ala
225                 230                 235                 240

Pro Ser Ala Gly Asp Asp Pro Leu Ala Leu Leu Ile Tyr Thr Ser Gly
                245                 250                 255

Ser Thr Gly Ala Pro Lys Gly Ala Met Tyr Ser Glu Asn Ile Val Arg
            260                 265                 270

Arg Trp Trp Ile Arg Glu Asp Val Met Ala Gly Thr Glu Asn Leu Pro
        275                 280                 285

```
Met Ile Gly Leu Asn Phe Met Pro Met Ser His Ile Met Gly Arg Gly
    290                 295                 300
Thr Leu Thr Ser Thr Leu Ser Thr Gly Gly Thr Gly Tyr Phe Ala Ala
305                 310                 315                 320
Ser Ser Asp Met Ser Thr Leu Phe Glu Asp Met Glu Leu Ile Arg Pro
                325                 330                 335
Thr Ala Leu Ala Leu Val Pro Arg Val Cys Asp Met Val Phe Gln Arg
                340                 345                 350
Phe Gln Thr Glu Val Asp Arg Arg Leu Ala Ser Gly Asp Thr Ala Ser
            355                 360                 365
Ala Glu Ala Val Ala Ala Glu Val Lys Ala Asp Ile Arg Asp Asn Leu
        370                 375                 380
Phe Gly Gly Arg Val Ser Ala Val Met Val Gly Ser Ala Pro Leu Ser
385                 390                 395                 400
Glu Glu Leu Gly Glu Phe Ile Glu Ser Cys Phe Glu Leu Asn Leu Thr
                405                 410                 415
Asp Gly Tyr Gly Ser Thr Glu Ala Gly Met Val Phe Arg Asp Gly Ile
                420                 425                 430
Val Gln Arg Pro Pro Val Ile Asp Tyr Lys Leu Val Asp Val Pro Glu
        435                 440                 445
Leu Gly Tyr Phe Ser Thr Asp Lys Pro His Pro Arg Gly Glu Leu Leu
    450                 455                 460
Leu Lys Thr Asp Gly Met Phe Leu Gly Tyr Tyr Lys Arg Pro Glu Val
465                 470                 475                 480
Thr Ala Ser Val Phe Asp Ala Asp Gly Phe Tyr Met Thr Gly Asp Ile
                485                 490                 495
Val Ala Glu Leu Ala His Asp Asn Ile Glu Ile Ile Asp Arg Arg Asn
                500                 505                 510
Asn Val Leu Lys Leu Ser Gln Gly Glu Phe Val Ala Val Ala Thr Leu
        515                 520                 525
Glu Ala Glu Tyr Ala Asn Ser Pro Val Val His Gln Ile Tyr Val Tyr
    530                 535                 540
Gly Ser Ser Glu Arg Ser Tyr Leu Leu Ala Val Val Pro Thr Pro
545                 550                 555                 560
Glu Ala Val Ala Ala Lys Gly Asp Ala Ala Ala Leu Lys Thr Thr
                565                 570                 575
Ile Ala Asp Ser Leu Gln Asp Ile Ala Lys Glu Ile Gln Leu Gln Ser
                580                 585                 590
Tyr Glu Val Pro Arg Asp Phe Ile Ile Glu Pro Gln Pro Phe Thr Gln
            595                 600                 605
Gly Asn Gly Leu Leu Thr Gly Ile Ala Lys Leu Ala Arg Pro Asn Leu
        610                 615                 620
Lys Ala His Tyr Gly Pro Arg Leu Glu Gln Met Tyr Ala Glu Ile Ala
625                 630                 635                 640
Glu Gln Gln Ala Ala Glu Leu Arg Ala Leu His Gly Val Asp Pro Asp
                645                 650                 655
Lys Pro Ala Leu Glu Thr Val Leu Lys Ala Ala Gln Ala Leu Leu Gly
                660                 665                 670
Val Ser Ser Ala Glu Leu Ala Ala Asp Ala His Phe Thr Asp Leu Gly
            675                 680                 685
Gly Asp Ser Leu Ser Ala Leu Ser Phe Ser Asp Leu Leu Arg Asp Ile
        690                 695                 700
```

```
Phe Ala Val Glu Val Pro Val Gly Val Ile Val Ser Ala Ala Asn Asp
705                 710                 715                 720

Leu Gly Gly Val Ala Lys Phe Val Asp Glu Gln Arg His Ser Gly Gly
            725                 730                 735

Thr Arg Pro Thr Ala Glu Thr Val His Gly Ala Gly His Thr Glu Ile
            740                 745                 750

Arg Ala Ala Asp Leu Thr Leu Asp Lys Phe Ile Asp Glu Ala Thr Leu
            755                 760                 765

His Ala Ala Pro Ser Leu Pro Lys Ala Ala Gly Ile Pro His Thr Val
            770                 775                 780

Leu Leu Thr Gly Ser Asn Gly Tyr Leu Gly His Tyr Leu Ala Leu Glu
785                 790                 795                 800

Trp Leu Glu Arg Leu Asp Lys Thr Asp Gly Lys Leu Ile Val Ile Val
                805                 810                 815

Arg Gly Lys Asn Ala Glu Ala Ala Tyr Gly Arg Leu Glu Glu Ala Phe
            820                 825                 830

Asp Thr Gly Asp Thr Glu Leu Leu Ala His Phe Arg Ser Leu Ala Asp
            835                 840                 845

Lys His Leu Glu Val Leu Ala Gly Asp Ile Gly Asp Pro Asn Leu Gly
            850                 855                 860

Leu Asp Ala Asp Thr Trp Gln Arg Leu Ala Asp Thr Val Asp Val Ile
865                 870                 875                 880

Val His Pro Ala Ala Leu Val Asn His Val Leu Pro Tyr Asn Gln Leu
                885                 890                 895

Phe Gly Pro Asn Val Val Gly Thr Ala Glu Ile Ile Lys Leu Ala Ile
            900                 905                 910

Thr Thr Lys Ile Lys Pro Val Thr Tyr Leu Ser Thr Val Ala Val Ala
            915                 920                 925

Ala Tyr Val Asp Pro Thr Thr Phe Asp Glu Glu Ser Asp Ile Arg Leu
            930                 935                 940

Ile Ser Ala Val Arg Pro Ile Asp Asp Gly Tyr Ala Asn Gly Tyr Gly
945                 950                 955                 960

Asn Ala Lys Trp Ala Gly Glu Val Leu Leu Arg Glu Ala His Asp Leu
                965                 970                 975

Cys Gly Leu Pro Val Ala Val Phe Arg Ser Asp Met Ile Leu Ala His
            980                 985                 990

Ser Arg Tyr Thr Gly Gln Leu Asn Val Pro Asp Gln Phe Thr Arg Leu
            995                 1000                1005

Ile Leu Ser Leu Ile Ala Thr Gly Ile Ala Pro Gly Ser Phe Tyr Gln
    1010                1015                1020

Ala Gln Thr Thr Gly Glu Arg Pro Leu Ala His Tyr Asp Gly Leu Pro
1025                1030                1035                1040

Gly Asp Phe Thr Ala Glu Ala Ile Thr Thr Leu Gly Thr Gln Val Pro
                1045                1050                1055

Glu Gly Ser Glu Gly Phe Val Tyr Asp Cys Val Asn Pro His Ala
            1060                1065                1070

Asp Gly Ile Ser Leu Asp Asn Phe Val Asp Trp Leu Ile Glu Ala Gly
            1075                1080                1085

Tyr Pro Ile Ala Arg Ile Asp Asn Tyr Thr Glu Trp Phe Thr Arg Phe
            1090                1095                1100

Asp Thr Ala Ile Arg Gly Leu Ser Glu Lys Gln Lys Gln His Ser Leu
1105                1110                1115                1120

Leu Pro Leu Leu His Ala Phe Glu Gln Pro Ser Ala Ala Glu Asn His
```

-continued

```
                           1125                1130                1135
        Gly Val Val Pro Ala Lys Arg Phe Gln His Ala Val Gln Ala Ala Gly
                       1140                1145                1150

Ile Gly Pro Val Gly Gln Asp Gly Thr Thr Asp Ile Pro His Leu Ser
                       1155                1160                1165

Arg Arg Leu Ile Val Lys Tyr Ala Lys Asp Leu Glu Gln Leu Gly Leu
                       1170                1175                1180

Leu
        1185

<210> SEQ ID NO 6
<211> LENGTH: 1186
<212> TYPE: PRT
<213> ORGANISM: Segniliparus rotundus

<400> SEQUENCE: 6

Met Thr Gln Ser His Thr Gln Gly Pro Gln Ala Ser Ala Ala His Ser
  1               5                  10                  15

Arg Leu Ala Arg Arg Ala Ala Glu Leu Leu Ala Thr Asp Pro Gln Ala
                 20                  25                  30

Ala Ala Thr Leu Pro Asp Pro Glu Val Val Arg Gln Ala Thr Arg Pro
             35                  40                  45

Gly Leu Arg Leu Ala Glu Arg Val Asp Ala Ile Leu Ser Gly Tyr Ala
         50                  55                  60

Asp Arg Pro Ala Leu Gly Gln Arg Ser Phe Gln Thr Val Lys Asp Pro
 65                  70                  75                  80

Ile Thr Gly Arg Ser Ser Val Glu Leu Leu Pro Thr Phe Asp Thr Ile
                 85                  90                  95

Thr Tyr Arg Glu Leu Arg Glu Arg Ala Thr Ala Ile Ala Ser Asp Leu
            100                 105                 110

Ala His His Pro Gln Ala Pro Ala Lys Pro Gly Asp Phe Leu Ala Ser
        115                 120                 125

Ile Gly Phe Ile Ser Val Asp Tyr Val Ala Ile Asp Ile Ala Gly Val
    130                 135                 140

Phe Ala Gly Leu Thr Ala Val Pro Leu Gln Thr Gly Ala Thr Leu Ala
145                 150                 155                 160

Thr Leu Thr Ala Ile Thr Ala Glu Thr Ala Pro Thr Leu Phe Ala Ala
                165                 170                 175

Ser Ile Glu His Leu Pro Thr Ala Val Asp Ala Val Leu Ala Thr Pro
            180                 185                 190

Ser Val Arg Arg Leu Leu Val Phe Asp Tyr Arg Ala Gly Ser Asp Glu
        195                 200                 205

Asp Arg Glu Ala Val Glu Ala Ala Lys Arg Lys Ile Ala Asp Ala Gly
    210                 215                 220

Ser Ser Val Leu Val Asp Val Leu Asp Glu Val Ile Ala Arg Gly Lys
225                 230                 235                 240

Ser Ala Pro Lys Ala Pro Leu Pro Pro Ala Thr Asp Ala Gly Asp Asp
                245                 250                 255

Ser Leu Ser Leu Leu Ile Tyr Thr Ser Gly Ser Thr Gly Thr Pro Lys
            260                 265                 270

Gly Ala Met Tyr Pro Glu Arg Asn Val Ala His Phe Trp Gly Gly Val
        275                 280                 285

Trp Ala Ala Ala Phe Asp Glu Asp Ala Ala Pro Val Pro Ala Ile
    290                 295                 300
```

```
Asn Ile Thr Phe Leu Pro Leu Ser His Val Ala Ser Arg Leu Ser Leu
305                 310                 315                 320

Met Pro Thr Leu Ala Arg Gly Gly Leu Met His Phe Val Ala Lys Ser
            325                 330                 335

Asp Leu Ser Thr Leu Phe Glu Asp Leu Lys Leu Ala Arg Pro Thr Asn
            340                 345                 350

Leu Phe Leu Val Pro Arg Val Glu Met Leu Tyr Gln His Tyr Gln
        355                 360                 365

Ser Glu Leu Asp Arg Arg Gly Val Gln Asp Gly Thr Arg Glu Ala Glu
370                 375                 380

Ala Val Lys Asp Asp Leu Arg Thr Gly Leu Leu Gly Gly Arg Ile Leu
385                 390                 395                 400

Thr Ala Gly Phe Gly Ser Ala Pro Leu Ser Ala Glu Leu Ala Gly Phe
            405                 410                 415

Ile Glu Ser Leu Leu Gln Ile His Leu Val Asp Gly Tyr Gly Ser Thr
            420                 425                 430

Glu Ala Gly Pro Val Trp Arg Asp Gly Tyr Leu Val Lys Pro Pro Val
            435                 440                 445

Thr Asp Tyr Lys Leu Ile Asp Val Pro Glu Leu Gly Tyr Phe Ser Thr
450                 455                 460

Asp Ser Pro His Pro Arg Gly Glu Leu Ala Ile Lys Thr Gln Thr Ile
465                 470                 475                 480

Leu Pro Gly Tyr Tyr Lys Arg Pro Glu Thr Thr Ala Glu Val Phe Asp
            485                 490                 495

Glu Asp Gly Phe Tyr Leu Thr Gly Asp Val Val Ala Gln Ile Gly Pro
            500                 505                 510

Glu Gln Phe Ala Tyr Val Asp Arg Arg Lys Asn Val Leu Lys Leu Ser
            515                 520                 525

Gln Gly Glu Phe Val Thr Leu Ala Lys Leu Glu Ala Ala Tyr Ser Ser
        530                 535                 540

Ser Pro Leu Val Arg Gln Leu Phe Val Tyr Gly Ser Ser Glu Arg Ser
545                 550                 555                 560

Tyr Leu Leu Ala Val Ile Val Pro Thr Pro Asp Ala Leu Lys Lys Phe
            565                 570                 575

Gly Val Gly Glu Ala Lys Ala Ala Leu Gly Glu Ser Leu Gln Lys
            580                 585                 590

Ile Ala Arg Asp Glu Gly Leu Gln Ser Tyr Glu Val Pro Arg Asp Phe
        595                 600                 605

Ile Ile Glu Thr Asp Pro Phe Thr Val Glu Asn Gly Leu Leu Ser Asp
610                 615                 620

Ala Arg Lys Ser Leu Arg Pro Lys Leu Lys Glu His Tyr Gly Glu Arg
625                 630                 635                 640

Leu Glu Ala Met Tyr Lys Glu Leu Ala Asp Gly Gln Ala Asn Glu Leu
            645                 650                 655

Arg Asp Ile Arg Arg Gly Val Gln Gln Arg Pro Thr Leu Glu Thr Val
            660                 665                 670

Arg Arg Ala Ala Ala Ala Met Leu Gly Ala Ser Ala Ala Glu Ile Lys
            675                 680                 685

Pro Asp Ala His Phe Thr Asp Leu Gly Gly Asp Ser Leu Ser Ala Leu
            690                 695                 700

Thr Phe Ser Asn Phe Leu His Asp Leu Phe Glu Val Asp Val Pro Val
705                 710                 715                 720

Gly Val Ile Val Ser Ala Ala Asn Thr Leu Gly Ser Val Ala Glu His
```

```
                725                 730                 735
Ile Asp Ala Gln Leu Ala Gly Gly Arg Ala Arg Pro Thr Phe Ala Thr
            740                 745                 750
Val His Gly Lys Gly Ser Thr Thr Ile Lys Ala Ser Asp Leu Thr Leu
            755                 760                 765
Asp Lys Phe Ile Asp Glu Gln Thr Leu Glu Ala Ala Lys His Leu Pro
        770                 775                 780
Lys Pro Ala Asp Pro Pro Arg Thr Val Leu Leu Thr Gly Ala Asn Gly
785                 790                 795                 800
Trp Leu Gly Arg Phe Leu Ala Leu Glu Trp Leu Glu Arg Leu Ala Pro
                805                 810                 815
Ala Gly Gly Lys Leu Ile Thr Ile Val Arg Gly Lys Asp Ala Ala Gln
            820                 825                 830
Ala Lys Ala Arg Leu Asp Ala Ala Tyr Glu Ser Gly Asp Pro Lys Leu
            835                 840                 845
Ala Gly His Tyr Gln Asp Leu Ala Ala Thr Thr Leu Glu Val Leu Ala
        850                 855                 860
Gly Asp Phe Ser Glu Pro Arg Leu Gly Leu Asp Glu Ala Thr Trp Asn
865                 870                 875                 880
Arg Leu Ala Asp Glu Val Asp Phe Ile Ser His Pro Gly Ala Leu Val
                885                 890                 895
Asn His Val Leu Pro Tyr Asn Gln Leu Phe Gly Pro Asn Val Ala Gly
            900                 905                 910
Val Ala Glu Ile Ile Lys Leu Ala Ile Thr Thr Arg Ile Lys Pro Val
            915                 920                 925
Thr Tyr Leu Ser Thr Val Ala Val Ala Gly Val Glu Pro Ser Ala
        930                 935                 940
Leu Asp Glu Asp Gly Asp Ile Arg Thr Val Ser Ala Glu Arg Ser Val
945                 950                 955                 960
Asp Glu Gly Tyr Ala Asn Gly Tyr Gly Asn Ser Lys Trp Gly Gly Glu
                965                 970                 975
Val Leu Leu Arg Glu Ala His Asp Arg Thr Gly Leu Pro Val Arg Val
            980                 985                 990
Phe Arg Ser Asp Met Ile Leu Ala His Gln Lys Tyr Thr Gly Gln Val
        995                 1000                1005
Asn Ala Thr Asp Gln Phe Thr Arg Leu Val Gln Ser Leu Leu Ala Thr
        1010                1015                1020
Gly Leu Ala Pro Lys Ser Phe Tyr Glu Leu Asp Ala Gln Gly Asn Arg
1025                1030                1035                1040
Gln Arg Ala His Tyr Asp Gly Ile Pro Val Asp Phe Thr Ala Glu Ser
            1045                1050                1055
Ile Thr Thr Leu Gly Gly Asp Gly Leu Glu Gly Tyr Arg Ser Tyr Asn
        1060                1065                1070
Val Phe Asn Pro His Arg Asp Gly Val Gly Leu Asp Glu Phe Val Asp
        1075                1080                1085
Trp Leu Ile Glu Ala Gly His Pro Ile Thr Arg Ile Asp Asp Tyr Asp
    1090                1095                1100
Gln Trp Leu Ser Arg Phe Glu Thr Ser Leu Arg Gly Leu Pro Glu Ser
1105                1110                1115                1120
Lys Arg Gln Ala Ser Val Leu Pro Leu Leu His Ala Phe Ala Arg Pro
            1125                1130                1135
Gly Pro Ala Val Asp Gly Ser Pro Phe Arg Asn Thr Val Phe Arg Thr
        1140                1145                1150
```

Asp Val Gln Lys Ala Lys Ile Gly Ala Glu His Asp Ile Pro His Leu
         1155                1160                1165

Gly Lys Ala Leu Val Leu Lys Tyr Ala Asp Asp Ile Lys Gln Leu Gly
    1170                1175                1180

Leu Leu
1185

<210> SEQ ID NO 7
<211> LENGTH: 459
<212> TYPE: PRT
<213> ORGANISM: Chromobacterium violaceum

<400> SEQUENCE: 7

Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Ser Glu
        35                  40                  45

Gly Asn Lys Ile Ile Asp Gly Met Ala Gly Leu Trp Cys Val Asn Val
    50                  55                  60

Gly Tyr Gly Arg Lys Asp Phe Ala Glu Ala Ala Arg Arg Gln Met Glu
65              70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
    210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
    290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val

```
            325                 330                 335
Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
            355                 360                 365

His Val Asp Asp Val Arg Gly Val Gly Met Val Gln Ala Phe Thr Leu
            370                 375                 380

Val Lys Asn Lys Ala Lys Arg Glu Leu Phe Pro Asp Phe Gly Glu Ile
385                 390                 395                 400

Gly Thr Leu Cys Arg Asp Ile Phe Phe Arg Asn Asn Leu Ile Met Arg
            405                 410                 415

Ala Cys Gly Asp His Ile Val Ser Ala Pro Leu Val Met Thr Arg
            420                 425                 430

Ala Glu Val Asp Glu Met Leu Ala Val Ala Glu Arg Cys Leu Glu Glu
            435                 440                 445

Phe Glu Gln Thr Leu Lys Ala Arg Gly Leu Ala
            450                 455
```

<210> SEQ ID NO 8
<211> LENGTH: 468
<212> TYPE: PRT
<213> ORGANISM: Pseudomonas aeruginosa

<400> SEQUENCE: 8

```
Met Asn Ala Arg Leu His Ala Thr Ser Pro Leu Gly Asp Ala Asp Leu
1               5                   10                  15

Val Arg Ala Asp Gln Ala His Tyr Met His Gly Tyr His Val Phe Asp
            20                  25                  30

Asp His Arg Val Asn Gly Ser Leu Asn Ile Ala Ala Gly Asp Gly Ala
            35                  40                  45

Tyr Ile Tyr Asp Thr Ala Gly Asn Arg Tyr Leu Asp Ala Val Gly Gly
        50                  55                  60

Met Trp Cys Thr Asn Ile Gly Leu Gly Arg Glu Glu Met Ala Arg Thr
65              70                  75                  80

Val Ala Glu Gln Thr Arg Leu Leu Ala Tyr Ser Asn Pro Phe Cys Asp
            85                  90                  95

Met Ala Asn Pro Arg Ala Ile Glu Leu Cys Arg Lys Leu Ala Glu Leu
            100                 105                 110

Ala Pro Gly Asp Leu Asp His Val Phe Leu Thr Thr Gly Gly Ser Thr
            115                 120                 125

Ala Val Asp Thr Ala Ile Arg Leu Met His Tyr Tyr Gln Asn Cys Arg
        130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
            165                 170                 175

Pro Ala Glu Phe Asp Phe Leu Asp Glu Arg Ile His His Leu Ala Cys
            180                 185                 190

Pro Tyr Tyr Tyr Arg Ala Pro Glu Gly Leu Gly Glu Ala Glu Phe Leu
            195                 200                 205

Asp Gly Leu Val Asp Glu Phe Glu Arg Lys Ile Leu Glu Leu Gly Ala
        210                 215                 220

Asp Arg Val Gly Ala Phe Ile Ser Glu Pro Val Phe Gly Ser Gly Gly
225                 230                 235                 240
```

Val Ile Val Pro Pro Ala Gly Tyr His Arg Arg Met Trp Glu Leu Cys
              245                 250                 255

Gln Arg Tyr Asp Val Leu Tyr Ile Ser Asp Glu Val Val Thr Ser Phe
          260                 265                 270

Gly Arg Leu Gly His Phe Phe Ala Ser Gln Ala Val Phe Gly Val Gln
      275                 280                 285

Pro Asp Ile Ile Leu Thr Ala Lys Gly Leu Thr Ser Gly Tyr Gln Pro
  290                 295                 300

Leu Gly Ala Cys Ile Phe Ser Arg Arg Ile Trp Glu Val Ile Ala Glu
305                 310                 315                 320

Pro Asp Lys Gly Arg Cys Phe Ser His Gly Phe Thr Tyr Ser Gly His
              325                 330                 335

Pro Val Ala Cys Ala Ala Ala Leu Lys Asn Ile Glu Ile Ile Glu Arg
          340                 345                 350

Glu Gly Leu Leu Ala His Ala Asp Glu Val Gly Arg Tyr Phe Glu Glu
      355                 360                 365

Arg Leu Gln Ser Leu Arg Asp Leu Pro Ile Val Gly Asp Val Arg Gly
  370                 375                 380

Met Arg Phe Met Ala Cys Val Glu Phe Val Ala Asp Lys Ala Ser Lys
385                 390                 395                 400

Ala Leu Phe Pro Glu Ser Leu Asn Ile Gly Glu Trp Val His Leu Arg
              405                 410                 415

Ala Gln Lys Arg Gly Leu Leu Val Arg Pro Ile Val His Leu Asn Val
          420                 425                 430

Met Ser Pro Pro Leu Ile Leu Thr Arg Glu Gln Val Asp Thr Val Val
      435                 440                 445

Arg Val Leu Arg Glu Ser Ile Glu Glu Thr Val Glu Asp Leu Val Arg
  450                 455                 460

Ala Gly His Arg
465

<210> SEQ ID NO 9
<211> LENGTH: 454
<212> TYPE: PRT
<213> ORGANISM: Pseudomonas syringae

<400> SEQUENCE: 9

Met Ser Ala Asn Asn Pro Gln Thr Leu Glu Trp Gln Ala Leu Ser Ser
1               5                   10                  15

Glu His His Leu Ala Pro Phe Ser Asp Tyr Lys Gln Leu Lys Glu Lys
              20                  25                  30

Gly Pro Arg Ile Ile Thr Arg Ala Glu Gly Val Tyr Leu Trp Asp Ser
          35                  40                  45

Glu Gly Asn Lys Ile Leu Asp Gly Met Ser Gly Leu Trp Cys Val Ala
      50                  55                  60

Ile Gly Tyr Gly Arg Glu Glu Leu Ala Asp Ala Ala Ser Lys Gln Met
65                  70                  75                  80

Arg Glu Leu Pro Tyr Tyr Asn Leu Phe Phe Gln Thr Ala His Pro Pro
              85                  90                  95

Val Leu Glu Leu Ala Lys Ala Ile Ser Asp Ile Ala Pro Glu Gly Met
          100                 105                 110

Asn His Val Phe Phe Thr Gly Ser Gly Ser Glu Gly Asn Asp Thr Met
      115                 120                 125

Leu Arg Met Val Arg His Tyr Trp Ala Leu Lys Gly Gln Pro Asn Lys
  130                 135                 140

Lys Thr Ile Ile Ser Arg Val Asn Gly Tyr His Gly Ser Thr Val Ala
145                 150                 155                 160

Gly Ala Ser Leu Gly Gly Met Thr Tyr Met His Glu Gln Gly Asp Leu
            165                 170                 175

Pro Ile Pro Gly Val Val His Ile Pro Gln Pro Tyr Trp Phe Gly Glu
        180                 185                 190

Gly Gly Asp Met Thr Pro Asp Glu Phe Gly Ile Trp Ala Ala Glu Gln
    195                 200                 205

Leu Glu Lys Lys Ile Leu Glu Leu Gly Val Glu Asn Val Gly Ala Phe
210                 215                 220

Ile Ala Glu Pro Ile Gln Gly Ala Gly Gly Val Ile Val Pro Pro Asp
225                 230                 235                 240

Ser Tyr Trp Pro Lys Ile Lys Glu Ile Leu Ser Arg Tyr Asp Ile Leu
                245                 250                 255

Phe Ala Ala Asp Glu Val Ile Cys Gly Phe Gly Arg Thr Ser Glu Trp
            260                 265                 270

Phe Gly Ser Asp Phe Tyr Gly Leu Arg Pro Asp Met Met Thr Ile Ala
        275                 280                 285

Lys Gly Leu Thr Ser Gly Tyr Val Pro Met Gly Gly Leu Ile Val Arg
    290                 295                 300

Asp Glu Ile Val Ala Val Leu Asn Gly Gly Asp Phe Asn His Gly
305                 310                 315                 320

Phe Thr Tyr Ser Gly His Pro Val Ala Ala Val Ala Leu Glu Asn
                325                 330                 335

Ile Arg Ile Leu Arg Glu Glu Lys Ile Val Glu Arg Val Arg Ser Glu
            340                 345                 350

Thr Ala Pro Tyr Leu Gln Lys Arg Leu Arg Glu Leu Ser Asp His Pro
        355                 360                 365

Leu Val Gly Glu Val Arg Gly Val Gly Leu Leu Gly Ala Ile Glu Leu
    370                 375                 380

Val Lys Asp Lys Thr Thr Arg Glu Arg Tyr Thr Asp Lys Gly Ala Gly
385                 390                 395                 400

Met Ile Cys Arg Thr Phe Cys Phe Asp Asn Gly Leu Ile Met Arg Ala
                405                 410                 415

Val Gly Asp Thr Met Ile Ile Ala Pro Pro Leu Val Ile Ser Phe Ala
            420                 425                 430

Gln Ile Asp Glu Leu Val Glu Lys Ala Arg Thr Cys Leu Asp Leu Thr
        435                 440                 445

Leu Ala Val Leu Gln Gly
    450

<210> SEQ ID NO 10
<211> LENGTH: 467
<212> TYPE: PRT
<213> ORGANISM: Rhodobacter sphaeroides

<400> SEQUENCE: 10

Met Thr Arg Asn Asp Ala Thr Asn Ala Ala Gly Ala Val Gly Ala Ala
1               5                   10                  15

Met Arg Asp His Ile Leu Leu Pro Ala Gln Glu Met Ala Lys Leu Gly
            20                  25                  30

Lys Ser Ala Gln Pro Val Leu Thr His Ala Glu Gly Ile Tyr Val His
        35                  40                  45

Thr Glu Asp Gly Arg Arg Leu Ile Asp Gly Pro Ala Gly Met Trp Cys

-continued

```
                50                  55                  60
Ala Gln Val Gly Tyr Gly Arg Arg Glu Ile Val Asp Ala Met Ala His
 65                  70                  75                  80

Gln Ala Met Val Leu Pro Tyr Ala Ser Pro Trp Tyr Met Ala Thr Ser
                 85                  90                  95

Pro Ala Ala Arg Leu Ala Glu Lys Ile Ala Thr Leu Thr Pro Gly Asp
                100                 105                 110

Leu Asn Arg Ile Phe Phe Thr Thr Gly Gly Ser Thr Ala Val Asp Ser
                115                 120                 125

Ala Leu Arg Phe Ser Glu Phe Tyr Asn Asn Val Leu Gly Arg Pro Gln
                130                 135                 140

Lys Lys Arg Ile Ile Val Arg Tyr Asp Gly Tyr His Gly Ser Thr Ala
145                 150                 155                 160

Leu Thr Ala Ala Cys Thr Gly Arg Thr Gly Asn Trp Pro Asn Phe Asp
                165                 170                 175

Ile Ala Gln Asp Arg Ile Ser Phe Leu Ser Ser Pro Asn Pro Arg His
                180                 185                 190

Ala Gly Asn Arg Ser Gln Glu Ala Phe Leu Asp Asp Leu Val Gln Glu
                195                 200                 205

Phe Glu Asp Arg Ile Glu Ser Leu Gly Pro Asp Thr Ile Ala Ala Phe
                210                 215                 220

Leu Ala Glu Pro Ile Leu Ala Ser Gly Gly Val Ile Ile Pro Pro Ala
225                 230                 235                 240

Gly Tyr His Ala Arg Phe Lys Ala Ile Cys Glu Lys His Asp Ile Leu
                245                 250                 255

Tyr Ile Ser Asp Glu Val Val Thr Gly Phe Gly Arg Cys Gly Glu Trp
                260                 265                 270

Phe Ala Ser Glu Lys Val Phe Gly Val Val Pro Asp Ile Ile Thr Phe
                275                 280                 285

Ala Lys Gly Val Thr Ser Gly Tyr Val Pro Leu Gly Gly Leu Ala Ile
                290                 295                 300

Ser Glu Ala Val Leu Ala Arg Ile Ser Gly Glu Asn Ala Lys Gly Ser
305                 310                 315                 320

Trp Phe Thr Asn Gly Tyr Thr Tyr Ser Asn Gln Pro Val Ala Cys Ala
                325                 330                 335

Ala Ala Leu Ala Asn Ile Glu Leu Met Glu Arg Glu Gly Ile Val Asp
                340                 345                 350

Gln Ala Arg Glu Met Ala Asp Tyr Phe Ala Ala Leu Ala Ser Leu
                355                 360                 365

Arg Asp Leu Pro Gly Val Ala Glu Thr Arg Ser Val Gly Leu Val Gly
                370                 375                 380

Cys Val Gln Cys Leu Leu Asp Pro Thr Arg Ala Asp Gly Thr Ala Glu
385                 390                 395                 400

Asp Lys Ala Phe Thr Leu Lys Ile Asp Glu Arg Cys Phe Glu Leu Gly
                405                 410                 415

Leu Ile Val Arg Pro Leu Gly Asp Leu Cys Val Ile Ser Pro Pro Leu
                420                 425                 430

Ile Ile Ser Arg Ala Gln Ile Asp Glu Met Val Ala Ile Met Arg Gln
                435                 440                 445

Ala Ile Thr Glu Val Ser Ala Ala His Gly Leu Thr Ala Lys Glu Pro
                450                 455                 460

Ala Ala Val
465
```

<210> SEQ ID NO 11
<211> LENGTH: 459
<212> TYPE: PRT
<213> ORGANISM: Escherichia coli

<400> SEQUENCE: 11

Met Asn Arg Leu Pro Ser Ser Ala Ser Ala Leu Ala Cys Ser Ala His
1               5                   10                  15

Ala Leu Asn Leu Ile Glu Lys Arg Thr Leu Asp His Glu Glu Met Lys
            20                  25                  30

Ala Leu Asn Arg Glu Val Ile Glu Tyr Phe Lys Glu His Val Asn Pro
        35                  40                  45

Gly Phe Leu Glu Tyr Arg Lys Ser Val Thr Ala Gly Gly Asp Tyr Gly
    50                  55                  60

Ala Val Glu Trp Gln Ala Gly Ser Leu Asn Thr Leu Val Asp Thr Gln
65                  70                  75                  80

Gly Gln Glu Phe Ile Asp Cys Leu Gly Gly Phe Gly Ile Phe Asn Val
                85                  90                  95

Gly His Arg Asn Pro Val Val Ser Ala Val Gln Asn Gln Leu Ala
            100                 105                 110

Lys Gln Pro Leu His Ser Gln Glu Leu Leu Asp Pro Leu Arg Ala Met
        115                 120                 125

Leu Ala Lys Thr Leu Ala Ala Leu Thr Pro Gly Lys Leu Lys Tyr Ser
    130                 135                 140

Phe Phe Cys Asn Ser Gly Thr Glu Ser Val Glu Ala Ala Leu Lys Leu
145                 150                 155                 160

Ala Lys Ala Tyr Gln Ser Pro Arg Gly Lys Phe Thr Phe Ile Ala Thr
                165                 170                 175

Ser Gly Ala Phe His Gly Lys Ser Leu Gly Ala Leu Ser Ala Thr Ala
            180                 185                 190

Lys Ser Thr Phe Arg Lys Pro Phe Met Pro Leu Leu Pro Gly Phe Arg
        195                 200                 205

His Val Pro Phe Gly Asn Ile Glu Ala Met Arg Thr Ala Leu Asn Glu
    210                 215                 220

Cys Lys Lys Thr Gly Asp Asp Val Ala Ala Val Ile Leu Glu Pro Ile
225                 230                 235                 240

Gln Gly Glu Gly Gly Val Ile Leu Pro Pro Gly Tyr Leu Thr Ala
                245                 250                 255

Val Arg Lys Leu Cys Asp Glu Phe Gly Ala Leu Met Ile Leu Asp Glu
            260                 265                 270

Val Gln Thr Gly Met Gly Arg Thr Gly Lys Met Phe Ala Cys Glu His
        275                 280                 285

Glu Asn Val Gln Pro Asp Ile Leu Cys Leu Ala Lys Ala Leu Gly Gly
    290                 295                 300

Gly Val Met Pro Ile Gly Ala Thr Ile Ala Thr Glu Glu Val Phe Ser
305                 310                 315                 320

Val Leu Phe Asp Asn Pro Phe Leu His Thr Thr Thr Phe Gly Gly Asn
                325                 330                 335

Pro Leu Ala Cys Ala Ala Ala Leu Ala Thr Ile Asn Val Leu Leu Glu
            340                 345                 350

Gln Asn Leu Pro Ala Gln Ala Glu Gln Lys Gly Asp Met Leu Leu Asp
        355                 360                 365

Gly Phe Arg Gln Leu Ala Arg Glu Tyr Pro Asp Leu Val Gln Glu Ala

```
                    370                 375                 380
Arg Gly Lys Gly Met Leu Met Ala Ile Glu Phe Val Asp Asn Glu Ile
385                 390                 395                 400

Gly Tyr Asn Phe Ala Ser Glu Met Phe Arg Gln Arg Val Leu Val Ala
                405                 410                 415

Gly Thr Leu Asn Asn Ala Lys Thr Ile Arg Ile Glu Pro Pro Leu Thr
                420                 425                 430

Leu Thr Ile Glu Gln Cys Glu Leu Val Ile Lys Ala Ala Arg Lys Ala
                435                 440                 445

Leu Ala Ala Met Arg Val Ser Val Glu Glu Ala
                450                 455

<210> SEQ ID NO 12
<211> LENGTH: 453
<212> TYPE: PRT
<213> ORGANISM: Vibrio fluvialis

<400> SEQUENCE: 12

Met Asn Lys Pro Gln Ser Trp Glu Ala Arg Ala Glu Thr Tyr Ser Leu
  1               5                  10                  15

Tyr Gly Phe Thr Asp Met Pro Ser Leu His Gln Arg Gly Thr Val Val
                 20                  25                  30

Val Thr His Gly Glu Gly Pro Tyr Ile Val Asp Val Asn Gly Arg Arg
             35                  40                  45

Tyr Leu Asp Ala Asn Ser Gly Leu Trp Asn Met Val Ala Gly Phe Asp
 50                  55                  60

His Lys Gly Leu Ile Asp Ala Ala Lys Ala Gln Tyr Glu Arg Phe Pro
 65                  70                  75                  80

Gly Tyr His Ala Phe Phe Gly Arg Met Ser Asp Gln Thr Val Met Leu
                 85                  90                  95

Ser Glu Lys Leu Val Glu Val Ser Pro Phe Asp Ser Gly Arg Val Phe
                100                 105                 110

Tyr Thr Asn Ser Gly Ser Glu Ala Asn Asp Thr Met Val Lys Met Leu
            115                 120                 125

Trp Phe Leu His Ala Ala Glu Gly Lys Pro Gln Lys Arg Lys Ile Leu
130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285
```

```
Ala Gly Phe Phe Pro Met Gly Ala Val Ile Leu Gly Pro Glu Leu Ser
    290                 295                 300
Lys Arg Leu Glu Thr Ala Ile Glu Ala Ile Glu Glu Phe Pro His Gly
305                 310                 315                 320
Phe Thr Ala Ser Gly His Pro Val Gly Cys Ala Ile Ala Leu Lys Ala
                325                 330                 335
Ile Asp Val Val Met Asn Glu Gly Leu Ala Glu Asn Val Arg Arg Leu
            340                 345                 350
Ala Pro Arg Phe Glu Arg Leu Lys His Ile Ala Glu Arg Pro Asn
        355                 360                 365
Ile Gly Glu Tyr Arg Gly Ile Gly Phe Met Trp Ala Leu Glu Ala Val
    370                 375                 380
Lys Asp Lys Ala Ser Lys Thr Pro Phe Asp Gly Asn Leu Ser Val Ser
385                 390                 395                 400
Glu Arg Ile Ala Asn Thr Cys Thr Asp Leu Gly Leu Ile Cys Arg Pro
                405                 410                 415
Leu Gly Gln Ser Val Val Leu Cys Pro Pro Phe Ile Leu Thr Glu Ala
            420                 425                 430
Gln Met Asp Glu Met Phe Asp Lys Leu Glu Lys Ala Leu Asp Lys Val
        435                 440                 445
Phe Ala Glu Val Ala
    450

<210> SEQ ID NO 13
<211> LENGTH: 418
<212> TYPE: PRT
<213> ORGANISM: Polaromonas sp.

<400> SEQUENCE: 13

Met Ser Glu Ala Ile Val Val Asn Asn Gln Asn Asp Gln Ser Arg Ala
  1               5                  10                  15
Tyr Ala Ile Pro Leu Glu Asp Ile Asp Val Ser Asn Pro Glu Leu Phe
            20                  25                  30
Arg Asp Asn Thr Met Trp Gly Tyr Phe Glu Arg Leu Arg Arg Glu Asp
        35                  40                  45
Pro Val His Tyr Cys Lys Asp Ser Leu Phe Gly Pro Tyr Trp Ser Val
    50                  55                  60
Thr Lys Phe Lys Asp Ile Met Gln Val Glu Thr His Pro Glu Ile Phe
65                  70                  75                  80
Ser Ser Glu Gly Asn Ile Thr Ile Met Glu Ser Asn Ala Ala Val Thr
                85                  90                  95
Leu Pro Met Phe Ile Ala Met Asp Pro Pro Lys His Asp Val Gln Arg
            100                 105                 110
Met Ala Val Ser Pro Ile Val Ala Pro Glu Asn Leu Ala Lys Leu Glu
        115                 120                 125
Gly Leu Ile Arg Glu Arg Thr Gly Arg Ala Leu Asp Gly Leu Pro Ile
    130                 135                 140
Asn Glu Thr Phe Asp Trp Val Lys Leu Val Ser Ile Asn Leu Thr Thr
145                 150                 155                 160
Gln Met Leu Ala Thr Leu Phe Asp Phe Pro Trp Glu Ser Arg Ala Lys
                165                 170                 175
Leu Thr Arg Trp Ser Asp Val Ala Thr Ala Leu Val Gly Thr Gly Ile
            180                 185                 190
Ile Asp Ser Glu Glu Gln Arg Met Glu Glu Leu Lys Gly Cys Val Gln
        195                 200                 205
```

```
Tyr Met Thr Arg Leu Trp Asn Glu Arg Val Asn Val Pro Gly Asn
            210                 215                 220

Asp Leu Ile Ser Met Met Ala His Thr Glu Ser Met Arg Asn Met Thr
225                 230                 235                 240

Pro Glu Glu Phe Leu Gly Asn Leu Ile Leu Leu Ile Val Gly Gly Asn
                245                 250                 255

Asp Thr Thr Arg Asn Ser Met Thr Gly Gly Val Leu Ala Leu Asn Glu
            260                 265                 270

Asn Pro Asp Glu Tyr Arg Lys Leu Cys Ala Asn Pro Ala Leu Ile Ala
        275                 280                 285

Ser Met Val Pro Glu Ile Val Arg Trp Gln Thr Pro Leu Ala His Met
290                 295                 300

Arg Arg Thr Ala Leu Gln Asp Thr Glu Leu Gly Gly Lys Ser Ile Arg
305                 310                 315                 320

Lys Gly Asp Lys Val Ile Met Trp Tyr Val Ser Gly Asn Arg Asp Pro
                325                 330                 335

Glu Ala Ile Glu Asn Pro Asp Ala Phe Ile Ile Asp Arg Ala Lys Pro
            340                 345                 350

Arg His His Leu Ser Phe Gly Phe Gly Ile His Arg Cys Val Gly Asn
            355                 360                 365

Arg Leu Ala Glu Leu Gln Leu Arg Ile Val Trp Glu Glu Leu Leu Lys
370                 375                 380

Arg Trp Pro Asn Pro Gly Gln Ile Glu Val Val Gly Ala Pro Glu Arg
385                 390                 395                 400

Val Leu Ser Pro Phe Val Lys Gly Tyr Glu Ser Leu Pro Val Arg Ile
                405                 410                 415

Asn Ala

<210> SEQ ID NO 14
<211> LENGTH: 420
<212> TYPE: PRT
<213> ORGANISM: Mycobacterium sp. HXN-1500

<400> SEQUENCE: 14

Met Thr Glu Met Thr Val Ala Ala Ser Asp Ala Thr Asn Ala Ala Tyr
1               5                   10                  15

Gly Met Ala Leu Glu Asp Ile Asp Val Ser Asn Pro Leu Phe Arg
            20                  25                  30

Asp Asn Thr Trp His Pro Tyr Phe Lys Arg Leu Arg Glu Glu Asp Pro
        35                  40                  45

Val His Tyr Cys Lys Ser Ser Met Phe Gly Pro Tyr Trp Ser Val Thr
50                  55                  60

Lys Tyr Arg Asp Ile Met Ala Val Glu Thr Asn Pro Lys Val Phe Ser
65                  70                  75                  80

Ser Glu Ala Lys Ser Gly Gly Ile Thr Ile Met Asp Asp Asn Ala Ala
                85                  90                  95

Ala Ser Leu Pro Met Phe Ile Ala Met Asp Pro Pro Lys His Asp Val
            100                 105                 110

Gln Arg Lys Thr Val Ser Pro Ile Val Ala Pro Glu Asn Leu Ala Thr
        115                 120                 125

Met Glu Ser Val Ile Arg Gln Arg Thr Ala Asp Leu Leu Asp Gly Leu
130                 135                 140

Pro Ile Asn Glu Glu Phe Asp Trp Val His Arg Val Ser Ile Glu Leu
145                 150                 155                 160
```

```
Thr Thr Lys Met Leu Ala Thr Leu Phe Asp Phe Pro Trp Asp Asp Arg
            165                 170                 175

Ala Lys Leu Thr Arg Trp Ser Asp Val Thr Thr Ala Leu Pro Gly Gly
        180                 185                 190

Gly Ile Ile Asp Ser Glu Glu Gln Arg Met Ala Glu Leu Met Glu Cys
            195                 200                 205

Ala Thr Tyr Phe Thr Glu Leu Trp Asn Gln Arg Val Asn Ala Glu Pro
        210                 215                 220

Lys Asn Asp Leu Ile Ser Met Met Ala His Ser Glu Ser Thr Arg His
225                 230                 235                 240

Met Ala Pro Glu Glu Tyr Leu Gly Asn Ile Val Leu Leu Ile Val Gly
            245                 250                 255

Gly Asn Asp Thr Thr Arg Asn Ser Met Thr Gly Gly Val Leu Ala Leu
        260                 265                 270

Asn Glu Phe Pro Asp Glu Tyr Arg Lys Leu Ser Ala Asn Pro Ala Leu
    275                 280                 285

Ile Ser Ser Met Val Ser Glu Ile Ile Arg Trp Gln Thr Pro Leu Ser
    290                 295                 300

His Met Arg Arg Thr Ala Leu Glu Asp Ile Glu Phe Gly Gly Lys His
305                 310                 315                 320

Ile Arg Gln Gly Asp Lys Val Val Met Trp Tyr Val Ser Gly Asn Arg
            325                 330                 335

Asp Pro Glu Ala Ile Asp Asn Pro Asp Thr Phe Ile Ile Asp Arg Ala
        340                 345                 350

Lys Pro Arg Gln His Leu Ser Phe Gly Phe Gly Ile His Arg Cys Val
        355                 360                 365

Gly Asn Arg Leu Ala Glu Leu Gln Leu Asn Ile Leu Trp Glu Glu Ile
    370                 375                 380

Leu Lys Arg Trp Pro Asp Pro Leu Gln Ile Gln Val Leu Gln Glu Pro
385                 390                 395                 400

Thr Arg Val Leu Ser Pro Phe Val Lys Gly Tyr Glu Ser Leu Pro Val
                405                 410                 415

Arg Ile Asn Ala
            420

<210> SEQ ID NO 15
<211> LENGTH: 420
<212> TYPE: PRT
<213> ORGANISM: Mycobacterium austroafricanum

<400> SEQUENCE: 15

Met Thr Glu Met Thr Val Ala Ala Asn Asp Ala Thr Asn Ala Ala Tyr
1               5                   10                  15

Gly Met Ala Leu Glu Asp Ile Asp Val Ser Asn Pro Val Leu Phe Arg
            20                  25                  30

Asp Asn Thr Trp His Pro Tyr Phe Lys Arg Leu Arg Glu Glu Asp Pro
        35                  40                  45

Val His Tyr Cys Lys Ser Ser Met Phe Gly Pro Tyr Trp Ser Val Thr
    50                  55                  60

Lys Tyr Arg Asp Ile Met Ala Val Glu Thr Asn Pro Lys Val Phe Ser
65                  70                  75                  80

Ser Glu Ala Lys Ser Gly Gly Ile Thr Ile Met Asp Asp Asn Ala Ala
            85                  90                  95

Ala Ser Leu Pro Met Phe Ile Ala Met Asp Pro Pro Lys His Asp Val
```

```
            100                 105                 110
Gln Arg Lys Thr Val Ser Pro Ile Val Ala Pro Glu Asn Leu Ala Thr
        115                 120                 125
Met Glu Ser Val Ile Arg Gln Arg Thr Ala Asp Leu Leu Asp Gly Leu
    130                 135                 140
Pro Ile Asn Glu Glu Phe Asp Trp Val His Arg Val Ser Ile Asp Leu
145                 150                 155                 160
Thr Thr Lys Met Leu Ala Thr Leu Phe Asp Phe Pro Trp Asp Asp Arg
                165                 170                 175
Ala Lys Leu Thr Arg Trp Ser Asp Val Thr Thr Ala Leu Pro Gly Gly
            180                 185                 190
Gly Ile Ile Asp Ser Glu Glu Gln Arg Met Ala Glu Leu Met Glu Cys
        195                 200                 205
Ala Thr Tyr Phe Thr Glu Leu Trp Asn Gln Arg Val Asn Ala Glu Pro
    210                 215                 220
Lys Asn Asp Leu Ile Ser Met Met Ala His Ser Glu Ser Thr Arg His
225                 230                 235                 240
Met Ala Pro Glu Glu Tyr Leu Gly Asn Ile Val Leu Leu Ile Val Gly
                245                 250                 255
Gly Asn Asp Thr Thr Arg Asn Ser Met Thr Gly Gly Val Leu Ala Leu
            260                 265                 270
Asn Glu Phe Pro Asp Glu Tyr Arg Lys Leu Ser Ala Asn Pro Ala Leu
        275                 280                 285
Ile Ser Ser Met Val Ser Glu Ile Ile Arg Trp Gln Thr Pro Leu Ser
    290                 295                 300
His Met Arg Arg Thr Ala Leu Glu Asp Ile Glu Phe Gly Gly Lys His
305                 310                 315                 320
Ile Arg Gln Gly Asp Lys Val Val Met Trp Tyr Val Ser Gly Asn Arg
                325                 330                 335
Asp Pro Glu Ala Ile Asp Asn Pro Asp Thr Phe Ile Ile Asp Arg Ala
            340                 345                 350
Lys Pro Arg Gln His Leu Ser Phe Gly Phe Gly Ile His Arg Cys Val
        355                 360                 365
Gly Asn Arg Leu Ala Glu Leu Gln Leu Asn Ile Leu Trp Glu Glu Ile
    370                 375                 380
Leu Lys Arg Trp Pro Asp Pro Leu Gln Ile Gln Val Leu Gln Glu Pro
385                 390                 395                 400
Thr Arg Val Leu Ser Pro Phe Val Lys Gly Tyr Glu Ser Leu Pro Val
                405                 410                 415
Arg Ile Asn Ala
            420

<210> SEQ ID NO 16
<211> LENGTH: 405
<212> TYPE: PRT
<213> ORGANISM: Polaromonas sp. JS666

<400> SEQUENCE: 16

Met Ser Glu Thr Val Ile Ile Ala Gly Ala Gly Gln Ala Ala Gly Gln
1               5                   10                  15
Ala Val Ala Ser Leu Arg Gln Glu Gly Phe Asp Gly Arg Ile Val Leu
            20                  25                  30
Val Gly Ala Glu Pro Val Leu Pro Tyr Gln Arg Pro Pro Leu Ser Lys
        35                  40                  45
```

```
Ala Phe Leu Ala Gly Thr Leu Pro Leu Glu Arg Leu Phe Leu Lys Pro
 50                  55                  60

Pro Ala Phe Tyr Glu Gln Ala Arg Val Asp Thr Leu Leu Gly Val Ala
 65                  70                  75                  80

Val Thr Glu Leu Asp Ala Ala Arg Arg Gln Val Arg Leu Asp Asp Gly
                 85                  90                  95

Arg Glu Leu Ala Phe Asp His Leu Leu Leu Ala Thr Gly Gly Arg Ala
                100                 105                 110

Arg Arg Leu Asp Cys Pro Gly Ala Asp His Pro Arg Leu His Tyr Leu
            115                 120                 125

Arg Thr Val Ala Asp Val Asp Gly Ile Arg Ala Ala Leu Arg Pro Gly
130                 135                 140

Ala Arg Leu Val Leu Ile Gly Gly Gly Tyr Val Gly Leu Glu Ile Ala
145                 150                 155                 160

Ala Val Ala Ala Lys Leu Gly Leu Ala Val Thr Val Leu Glu Ala Ala
                165                 170                 175

Pro Thr Val Leu Ala Arg Val Thr Cys Pro Ala Val Ala Arg Phe Phe
                180                 185                 190

Glu Ser Val His Arg Gln Ala Gly Val Thr Ile Arg Cys Ala Thr Thr
            195                 200                 205

Val Ser Gly Ile Glu Gly Asp Ala Ser Leu Ala Arg Val Val Thr Gly
210                 215                 220

Asp Gly Glu Arg Ile Asp Ala Asp Leu Val Ile Ala Gly Ile Gly Leu
225                 230                 235                 240

Leu Pro Asn Val Glu Leu Ala Gln Ala Ala Gly Leu Val Cys Asp Asn
                245                 250                 255

Gly Ile Val Val Asp Glu Glu Cys Arg Thr Ser Val Pro Gly Ile Phe
                260                 265                 270

Ala Ala Gly Asp Cys Thr Gln His Pro Asn Ala Ile Tyr Asp Ser Arg
            275                 280                 285

Leu Arg Leu Glu Ser Val His Asn Ala Ile Glu Gln Gly Lys Thr Ala
            290                 295                 300

Ala Ala Ala Met Cys Gly Lys Ala Arg Pro Tyr Arg Gln Val Pro Trp
305                 310                 315                 320

Phe Trp Ser Asp Gln Tyr Asp Leu Lys Leu Gln Thr Ala Gly Leu Asn
                325                 330                 335

Arg Gly Tyr Asp Gln Val Val Met Arg Gly Ser Thr Asp Asn Arg Ser
                340                 345                 350

Phe Ala Ala Phe Tyr Leu Arg Asp Gly Arg Leu Leu Ala Val Asp Ala
            355                 360                 365

Val Asn Arg Pro Val Glu Phe Met Val Ala Lys Ala Leu Ile Ala Asn
370                 375                 380

Arg Thr Val Ile Ala Pro Glu Arg Leu Ala Asp Glu Arg Ile Ala Ala
385                 390                 395                 400

Lys Asp Leu Ala Gly
                405

<210> SEQ ID NO 17
<211> LENGTH: 424
<212> TYPE: PRT
<213> ORGANISM: Mycobacterium sp. HXN-1500

<400> SEQUENCE: 17

Met Ile His Thr Gly Val Thr Glu Ala Val Val Val Val Gly Ala Gly
 1               5                  10                  15
```

Gln Ala Gly Ala Gln Thr Val Thr Ser Leu Arg Gln Arg Gly Phe Glu
                20                  25                  30

Gly Gln Ile Thr Leu Leu Gly Asp Glu Pro Ala Leu Pro Tyr Gln Arg
            35                  40                  45

Pro Pro Leu Ser Lys Ala Phe Leu Ala Gly Thr Leu Pro Leu Asp Arg
50                  55                  60

Leu Tyr Leu Arg Pro Ala Ala Phe Tyr Gln Gln Ala His Val Asp Val
65                  70                  75                  80

Met Val Asp Thr Gly Val Ser Glu Leu Asp Thr Glu Asn Arg Arg Ile
                85                  90                  95

Arg Leu Thr Asp Gly Arg Ala Ile Ser Phe Asp His Leu Val Leu Ala
            100                 105                 110

Thr Gly Gly Arg Pro Arg Pro Leu Ala Cys Pro Gly Ala Asp His Pro
        115                 120                 125

Arg Val His Tyr Leu Arg Thr Val Thr Asp Val Asp Arg Ile Arg Ser
    130                 135                 140

Gln Phe His Pro Gly Thr Arg Leu Val Leu Val Gly Gly Gly Tyr Ile
145                 150                 155                 160

Gly Leu Glu Ile Ala Ala Val Ala Ala Glu Leu Gly Leu Thr Val Thr
                165                 170                 175

Val Leu Glu Ala Gln Thr Thr Val Leu Ala Arg Val Thr Cys Pro Thr
            180                 185                 190

Val Ala Arg Phe Phe Glu His Thr His Arg Arg Ala Gly Val Thr Ile
        195                 200                 205

Arg Cys Ala Thr Thr Val Thr Arg Ile His Asp Ser Ser Ser Thr Ala
    210                 215                 220

Arg Ile Glu Leu Asp Ser Gly Glu Tyr Ile Asp Ala Asp Leu Val Ile
225                 230                 235                 240

Val Gly Ile Gly Leu Leu Pro Asn Val Asp Leu Ala Ser Ala Ala Gly
                245                 250                 255

Leu Thr Cys Glu Ser Gly Ile Val Val Asp Ser Arg Cys Gln Thr Ser
            260                 265                 270

Ala Pro Gly Ile Tyr Ala Ala Gly Asp Cys Thr Gln Tyr Pro Ser Pro
        275                 280                 285

Ile Tyr Gly Arg Pro Leu His Leu Glu Ser Val His Asn Ala Ile Glu
    290                 295                 300

Gln Ala Lys Thr Ala Ala Ala Ile Leu Gly Arg Asp Glu Pro Phe
305                 310                 315                 320

Arg Gln Val Pro Trp Phe Trp Ser Asp Gln Tyr Asn Ile Lys Leu Gln
            325                 330                 335

Thr Ala Gly Val Asn Glu Gly Tyr Asp Asp Val Ile Ile Arg Gly Asp
        340                 345                 350

Pro Ala Ser Ala Ser Phe Ala Ala Phe Tyr Leu Arg Ala Gly Lys Leu
    355                 360                 365

Leu Ala Val Asp Ala Ile Asn Arg Pro Arg Glu Phe Met Ala Ser Lys
370                 375                 380

Thr Leu Ile Ala Glu Arg Ala Glu Val Asp Pro Thr Gln Leu Ala Asp
385                 390                 395                 400

Glu Ser Leu Pro Pro Thr Ala Leu Ala Ala Val Asn Gly Pro Thr
            405                 410                 415

Arg Ala Thr Ser Pro Thr Ser Leu
            420

-continued

<210> SEQ ID NO 18
<211> LENGTH: 106
<212> TYPE: PRT
<213> ORGANISM: Polaromonas sp. JS666

<400> SEQUENCE: 18

Met Thr Lys Val Thr Phe Ile Glu His Asn Gly Thr Val Arg Asn Val
1               5                   10                  15

Asp Val Asp Asp Gly Leu Ser Val Met Glu Ala Ala Val Asn Asn Leu
            20                  25                  30

Val Pro Gly Ile Asp Gly Asp Cys Gly Gly Ala Cys Ala Cys Ala Thr
        35                  40                  45

Cys His Val His Ile Asp Ala Ala Trp Leu Asp Lys Leu Pro Pro Met
50                  55                  60

Glu Ala Met Glu Lys Ser Met Leu Glu Phe Ala Glu Gly Arg Asn Glu
65                  70                  75                  80

Ser Ser Arg Leu Gly Cys Gln Ile Lys Leu Ser Pro Ala Leu Asp Gly
                85                  90                  95

Ile Val Val Arg Thr Pro Leu Gly Gln His
            100                 105

<210> SEQ ID NO 19
<211> LENGTH: 106
<212> TYPE: PRT
<213> ORGANISM: Mycobacterium sp. HXN-1500

<400> SEQUENCE: 19

Met Pro Lys Ile Thr Tyr Ile Asp Tyr Thr Gly Thr Ser Arg Cys Val
1               5                   10                  15

Asp Ala Glu Asn Gly Met Ser Leu Met Glu Ile Ala Ile Asn Asn Asn
            20                  25                  30

Val Pro Gly Ile Asp Gly Asp Cys Gly Gly Glu Cys Ala Cys Ala Thr
        35                  40                  45

Cys His Val His Val Asp Ala Asp Trp Leu Asp Lys Leu Pro Pro Ser
50                  55                  60

Ser Asp Gln Glu Val Ser Met Leu Glu Phe Cys Asp Gly Val Asp His
65                  70                  75                  80

Thr Ser Arg Leu Gly Cys Gln Ile Lys Ile Cys Pro Thr Leu Asp Gly
                85                  90                  95

Ile Val Val Arg Thr Pro Ala Ala Gln His
            100                 105

<210> SEQ ID NO 20
<211> LENGTH: 224
<212> TYPE: PRT
<213> ORGANISM: Bacillus subtilis

<400> SEQUENCE: 20

Met Lys Ile Tyr Gly Ile Tyr Met Asp Arg Pro Leu Ser Gln Glu Glu
1               5                   10                  15

Asn Glu Arg Phe Met Ser Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
50                  55                  60

Asp Ile Arg Phe Ser Thr Gln Glu Tyr Gly Lys Pro Cys Ile Pro Asp
65                  70                  75                  80

```
Leu Pro Asp Ala His Phe Asn Ile Ser His Ser Gly Arg Trp Val Ile
                 85                  90                  95

Cys Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
            115                 120                 125

Ser Asp Leu Leu Ala Lys Asp Lys Asp Glu Gln Thr Asp Tyr Phe Tyr
            130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
            195                 200                 205

Pro Asp Phe Pro Glu Asp Ile Thr Met Val Ser Tyr Glu Glu Leu Leu
210                 215                 220

<210> SEQ ID NO 21
<211> LENGTH: 222
<212> TYPE: PRT
<213> ORGANISM: Nocardia sp. NRRL 5646

<400> SEQUENCE: 21

Met Ile Glu Thr Ile Leu Pro Ala Gly Val Glu Ser Ala Glu Leu Leu
1               5                   10                  15

Glu Tyr Pro Glu Asp Leu Lys Ala His Pro Ala Glu His Leu Ile
                20                  25                  30

Ala Lys Ser Val Glu Lys Arg Arg Arg Asp Phe Ile Gly Ala Arg His
            35                  40                  45

Cys Ala Arg Leu Ala Leu Ala Glu Leu Gly Glu Pro Pro Val Ala Ile
50                  55                  60

Gly Lys Gly Glu Arg Gly Ala Pro Ile Trp Pro Arg Gly Val Val Gly
65                  70                  75                  80

Ser Leu Thr His Cys Asp Gly Tyr Arg Ala Ala Val Ala His Lys
                85                  90                  95

Met Arg Phe Arg Ser Ile Gly Ile Asp Ala Glu Pro His Ala Thr Leu
            100                 105                 110

Pro Glu Gly Val Leu Asp Ser Val Ser Leu Pro Pro Gly Arg Glu Trp
            115                 120                 125

Leu Lys Thr Thr Asp Ser Ala Leu His Leu Asp Arg Leu Leu Phe Cys
            130                 135                 140

Ala Lys Glu Ala Thr Tyr Lys Ala Trp Trp Pro Leu Thr Ala Arg Trp
145                 150                 155                 160

Leu Gly Phe Glu Glu Ala His Ile Thr Phe Glu Ile Glu Asp Gly Ser
                165                 170                 175

Ala Asp Ser Gly Asn Gly Thr Phe His Ser Glu Leu Leu Val Pro Gly
            180                 185                 190

Gln Thr Asn Asp Gly Gly Thr Pro Leu Leu Ser Phe Asp Gly Arg Trp
            195                 200                 205

Leu Ile Ala Asp Gly Phe Ile Leu Thr Ala Ile Ala Tyr Ala
210                 215                 220
```

METHODS OF PRODUCING 6-CARBON CHEMICALS VIA COA-DEPENDENT CARBON CHAIN ELONGATION ASSOCIATED WITH CARBON STORAGE

CROSS-REFERENCE TO RELATED APPLICATIONS

This application is a continuation-in-part of U.S. application Ser. No. 13/715,981, filed Dec. 14, 2012, which claims priority to U.S. Application Ser. No. 61/576,401, filed Dec. 16, 2011. The disclosures of the applications are incorporated by reference in their entirety.

TECHNICAL FIELD

This invention relates to methods for biosynthesizing one or more of adipic acid, 6-aminohexanoic acid, 6-hydroxyhexanoic acid, hexamethylenediamine, caprolactam, and 1,6-hexanediol using one or more isolated enzymes such as β-ketothiolases, dehydrogenases, reductases, hydratases, thioesterases, monooxygenases, and transaminases or using recombinant host cells expressing one or more such enzymes.

BACKGROUND

Nylons are polyamides that are generally synthesized by the condensation polymerisation of a diamine with a dicarboxylic acid. Similarly, Nylons may be produced by the condensation polymerization of lactams. A ubiquitous nylon is Nylon 6,6, which is produced by reaction of hexamethylenediamine (HMD) and adipic acid. Nylon 6 can be produced by a ring opening polymerization of caprolactam. Therefore, adipic acid, hexamethylenediamine and caprolactam are important intermediates in the production of Nylons (Anton & Baird, Polyamides Fibers, Encyclopedia of Polymer Science and Technology, 2001).

Industrially, adipic acid and caprolactam are produced via air oxidation of cyclohexane. The air oxidation of cyclohexane produces, in a series of steps, a mixture of cyclohexanone (K) and cyclohexanol (A), designated as KA oil. Nitric acid oxidation of KA oil produces adipic acid (Musser, Adipic acid, Ullmann's Encyclopedia of Industrial Chemistry, 2000). Caprolactam is produced from cyclohexanone via its oxime and subsequent acid rearrangement (Fuchs, Kieczka and Moran, Caprolactam, Ullmann's Encyclopedia of Industrial Chemistry, 2000)

Industrially, hexamethylenediamine (HMD) is produced by hydrocyanation of C6 building block to adiponitrile, followed by hydrogenation to HMD (Herzog and Smiley, Hexamethylenediamine, Ullmann's Encyclopedia of Industrial Chemistry, 2012).

Given a reliance on petrochemical feedstocks; biotechnology offers an alternative approach via biocatalysis. Biocatalysis is the use of biological catalysts, such as enzymes, to perform biochemical transformations of organic compounds.

Both bioderived feedstocks and petrochemical feedstocks are viable starting materials for the biocatalysis processes.

Accordingly, against this background, it is clear that there is a need for sustainable methods for producing one or more of adipic acid, caprolactam, 6-aminohexanoic acid, 6-hydroxyhexanoic acid, hexamethylenediamine, and 1,6-hexanediol (hereafter "C6 building blocks") wherein the methods are biocatalyst based (Jang et al., Biotechnology & Bioengineering, 2012, 109(10), 2437-2459).

However, no wild-type prokaryote or eukaryote naturally overproduces or excretes C6 building blocks to the extracellular environment. Nevertheless, the metabolism of adipic acid and caprolactam has been reported (Ramsay et al., Appl. Environ. Microbiol., 1986, 52(1), 152-156; and Kulkarni and Kanekar, Current Microbiology, 1998, 37, 191-194).

The dicarboxylic acid, adipic acid, is converted efficiently as a carbon source by a number of bacteria and yeasts via β-oxidation into central metabolites. β-oxidation of Coenzyme A (CoA) activated adipate to CoA activated 3-oxoadipate facilitates further catabolism via, for example, pathways associated with aromatic substrate degradation. The catabolism of 3-oxoadipyl-CoA to acetyl-CoA and succinyl-CoA by several bacteria and fungi has been characterized comprehensively (Harwood and Parales, Annual Review of Microbiology, 1996, 50, 553-590). Both adipate and 6-aminohexanoate are intermediates in the catabolism of caprolactam, finally degraded via 3-oxoadipyl-CoA to central metabolites.

Potential metabolic pathways have been suggested for producing adipic acid from biomass-sugar: (1) biochemically from glucose to cis,cis muconic acid via the ortho-cleavage aromatic degradation pathway, followed by chemical catalysis to adipic acid; (2) a reversible adipic acid degradation pathway via the condensation of succinyl-CoA and acetyl-CoA and (3) combining β-oxidation, a fatty acid synthase and ω-oxidation. However, no information using these strategies has been reported (Jang et al., Biotechnology & Bioengineering, 2012, 109(10), 2437-2459).

The optimality principle states that microorganisms regulate their biochemical networks to support maximum biomass growth. Beyond the need for expressing heterologous pathways in a host organism, directing carbon flux towards C6 building blocks that serve as carbon sources rather than as biomass growth constituents, contradicts the optimality principle. For example, transferring the 1-butanol pathway from Clostridium species into other production strains has often fallen short by an order of magnitude compared to the production performance of native producers (Shen et al., Appl. Environ. Microbiol., 2011, 77(9), 2905-2915).

The efficient synthesis of the six carbon aliphatic backbone precursor is a key consideration in synthesizing C6 building blocks prior to forming terminal functional groups, such as carboxyl, amine or hydroxyl groups, on the C6 aliphatic backbone.

SUMMARY

This document is based at least in part on the discovery that it is possible to construct biochemical pathways for producing a six carbon chain aliphatic backbone precursor, in which two functional groups, e.g., carboxyl, amine or hydroxyl, can be formed, leading to the synthesis of one or more of adipic acid, 6-aminohexanoic acid, 6-hydroxyhexanoic acid, hexamethylenediamine, caprolactam, and 1,6-hexanediol (hereafter "C6 building blocks"). Adipic acid and adipate, 6-hydroxyhexanoic acid and 6-hydroxyhexanoate, and 6-aminohexanoic and 6-aminohexanoate are used interchangeably herein to refer to the compound in any of its neutral or ionized forms, including any salt forms thereof. It is understood by those skilled in the art that the specific form will depend on pH. These pathways, metabolic engineering, and cultivation strategies described herein rely on CoA-dependent elongation enzymes or homologs thereof associated with the carbon storage pathways from polyhydroxyalkanoate accumulating bacteria.

In the face of the optimality principle, it surprisingly has been discovered that appropriate non-natural pathways, feedstocks, host microorganisms, attenuation strategies to the host's biochemical network, and cultivation strategies may be combined to efficiently produce C6 building blocks.

In some embodiments, the C6 aliphatic backbone for conversion to a C6 building block can be formed from acetyl-CoA via two cycles of CoA-dependent carbon chain elongation using either NADH or NADPH dependent enzymes. See FIG. 1 and FIG. 2.

In some embodiments, the enzyme in the CoA-dependent carbon chain elongation pathway generating the C6 aliphatic backbone catalyzes irreversible enzymatic steps.

In some embodiments, the terminal carboxyl groups can be enzymatically formed using a thioesterase, an aldehyde dehydrogenase, a 6-oxohexanoate dehydrogenase, a 7-oxoheptanoate dehydrogenase, or a monooxygenase (e.g., in combination with an oxidoreductase and ferredoxin). See FIG. 3 and FIG. 4. The thioesterase can have at least 70% sequence identity to the amino acid sequence set forth in SEQ ID NO: 1.

In some embodiments, the terminal amine groups can be enzymatically formed using a ω-transaminase or a deacetylase. See FIG. 5 and FIG. 6. The ω-transaminase can have at least 70% sequence identity to any one of the amino acid sequences set forth in SEQ ID NOs. 7-12.

In some embodiments, the terminal hydroxyl group can be enzymatically formed using a monooxygenase (e.g., in combination with an oxidoreductase and ferredoxin), or an alcohol dehydrogenase. See FIG. 7 and FIG. 8. The monooxygenase can have at least 70% sequence identity to any one of the amino acid sequences set forth in SEQ ID NO. 13-15.

In one aspect, this document features a method for biosynthesizing one or more products selected from the group consisting of adipic acid, 6-hydroxyhexanoic acid, 6-aminohexanoic acid, hexamethylenediamine, caprolactam, and 1,6-hexanediol. The method includes enzymatically synthesizing a six carbon chain aliphatic backbone (e.g., hexanoyl-CoA) and enzymatically forming, in one or more steps, two terminal functional groups selected from the group consisting of carboxyl, amine, and hydroxyl groups in the backbone to directly produce the product or producing the product in a subsequent step. The two terminal functional groups can be the same (e.g., hydroxyl or amine) or can be different (e.g., a terminal hydroxyl group and a terminal carboxyl group; or a terminal amine and a terminal carboxyl group).

Hexanoyl-CoA can be enzymatically synthesized from acetyl-CoA via two cycles of CoA-dependent carbon chain elongation using either NADH or NADPH dependent enzymes. Hexanoyl-CoA can be formed by conversion of hex-2-enoyl-CoA by an enoyl-CoA reductase classified under EC 1.3.1.44, EC 1.3.1.38, or EC 1.3.1.8 such as the gene product of ter or tdter. Hex-2-enoyl-CoA can be formed by conversion of (S) 3-hydroxyhexanoyl-CoA by a trans-2-enoyl-CoA hydratase classified under EC 4.2.1.17 or by conversion of (R) 3-hydroxyhexanoyl-CoA by a trans-2-enoyl-CoA hydratase classified under EC 4.2.1.119. The trans-2-enoyl-CoA hydratase can be the gene product of crt. (S) 3-hydroxyhexanoyl-CoA can be formed by conversion of 3-oxohexanoyl-CoA by a 3-hydroxyacyl-CoA dehydrogenase classified under EC 1.1.1.35 such as the 3-hydroxyacyl-CoA dehydrogenase encoded by fadB. The 3-oxohexanoyl-CoA can be formed by conversion of butanoyl-CoA by a β-ketothiolase classified under EC 2.3.1.16 such as that encoded by bktB. Butanoyl-CoA can be formed by conversion of crotonyl-CoA by an enoyl-CoA reductase classified under EC 1.3.1.44, EC 1.3.1.38, or EC 1.3.1.8. Crotonyl-CoA can be formed by conversion of (S) 3-hydroxybutanoyl-CoA by a trans-2-enoyl-CoA hydratase classified under EC 4.2.1.17. The (S) 3-hydroxybutanoyl-CoA can be formed by conversion of acetoacetyl-CoA by a 3-hydroxybutyryl-CoA dehydrogenase classified under EC 1.1.1.157 such as a 3-hydroxybutyryl-CoA dehydrogenase encoded by hbd. The acetoacetyl-CoA can be formed by conversion of acetyl-CoA by a β-ketothiolase classified under EC 2.3.1.9 such as that encoded by atoB or phaA. The acetoacetyl-CoA can be formed by conversion of malonyl-CoA by an acetoacetyl-CoA synthase classified under EC 2.3.1.194. The malonyl-CoA can be formed by conversion of acetyl-CoA by an acetyl-CoA carboxylase classified under EC 6.4.1.2.

The (R) 3-hydroxyhexanoyl-CoA can be formed by conversion of 3-oxohexanoyl-CoA by a 3-oxoacyl-CoA reductase classified under EC 1.1.1.100 such as that encoded by fabG. The crotonyl-CoA can be formed by conversion of (R) 3-hydroxybutanoyl-CoA by a trans-2-enoyl-CoA hydratase classified under EC 4.2.1.119. The trans-2-s enoyl-CoA hydratase can be the gene product of phaJ. (R) 3-hydroxybutanoyl-CoA can be formed by conversion of acetoacetyl-CoA by an acetoacyl-CoA reductase classified under EC 1.1.1.36 such as that encoded by phaB.

In any of the methods described herein, the method can include producing hexanoate by forming a first terminal carboxyl group in hexanoyl CoA using a thioesterase and an aldehyde dehydrogenase, or a thioesterase. The thioesterase can be encoded by YciA, tesB or Acot13. The thioesterase can have at least 70% sequence identity to the amino acid sequence set forth in SEQ ID NO: 1.

Hexanoate can be produced by forming a first terminal carboxyl group in hexanal by an aldehyde dehydrogenase classified under EC 1.2.1.4. Hexanal can be formed by conversion of hexanoyl-CoA by a butanal dehydrogenase classified under EC 1.2.1.57.

A carboxylate reductase (e.g., in combination with a phosphopantetheinyl transferase) can form a terminal aldehyde group as an intermediate in forming the product. The carboxylate reductase can have at least 70% sequence identity to any one of the amino acid sequences set forth in SEQ ID NO. 2-6.

In any of the methods described herein, the methods can include converting hexanoate to adipic acid, 6-aminohexanoic acid, hexamethylenediamine, 6-hydroxyhexanoic acid, ε caprolactam or 1,6 hexanediol with one or more enzymatic conversions, wherein one of the enzymatic conversions introduces the second terminal functional group. The method can include converting hexanoate to 6-hydroxyhexanoate using a monooxygenase such as from the family CYP153 such as CYP153A. 6-hydroxyhexanoate can be converted to adipate semialdehyde using (i) an alcohol dehydrogenase such as encoded by YMR318C, a 5-hydroxypentanoate dehydrogenase such as encoded by cpnD or a 4-hydroxybutyrate dehydrogenase such as encoded by gabD (ii) a 6-hydroxyhexanoate dehydrogenase such as that encoded by ChnD, or (iii) a monooxygenase in the cytochrome P450 family.

In any of the methods described herein, adipic acid can be produced by forming the second terminal functional group in adipate semialdehyde using (i) an aldehyde dehydrogenase classified under EC 1.2.1.3, (ii) a 6-oxohexanoate dehydrogenase classified under EC 1.2.1.63 such as that encoded by ChnE or a 7-oxoheptanoate dehydrogenase classified under EC 1.2.1.- (e.g., the gene product of ThnG) or iii) a monooxygenase in the cytochrome P450 family.

In any of the methods described herein, 6-aminohexanoic acid can be produced by forming the second terminal functional group in adipate semialdehyde using a ω-transaminase classified under EC 2.61.18, EC 2.6.1.19, EC 2.6.1.29, EC 2.6.1.48, or EC 2.6.1.82.

In any of the methods described herein, caprolactam can be produced from 6-aminohexanoic acid using a lactamase classified under EC 3.5.2.-. The amide bond associated with caprolactam is produced from a terminal carboxyl group and terminal amine group of 6-aminohexanoate.

In any of the methods described herein, hexamethylenediamine can be produced by forming a second terminal functional group in (i) 6-aminohexanal using a ω-transaminase classified under EC 2.61.18, EC 2.6.1.19, EC 2.6.1.29, EC 2.6.1.48 or EC 2.6.1.82 or in (ii) N6-acetyl-1,6-diaminohexane using a deacetylase classified, for example, under EC 3.5.1.17.

In any of the methods described herein, 1,6 hexanediol can be produced by forming the second terminal functional group in 6-hydroxyhexanal using an alcohol dehydrogenase classified under EC 1.1.1.- (e.g., 1, 2, 21, or 184) such as that encoded by YMR318C, YqhD or CAA81612.1.

In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

In some embodiments, the non-biological feedstock can be or can derive from natural gas, syngas, $CO_2/H_2$, methanol, ethanol, benzoate, non-volatile residue (NVR) or a caustic wash waste stream from cyclohexane oxidation processes, or terephthalic acid/isophthalic acid mixture waste streams.

In some embodiments, the host microorganism is a prokaryote. For example, the prokaryote can be from the bacterial genus *Escherichia* such as *Escherichia coli*; from the bacterial genus *Clostridia* such as *Clostridium ljungdahlii*, *Clostridium autoethanogenum* or *Clostridium kluyveri*; from the bacterial genus *Corynebacteria* such as *Corynebacterium glutamicum*; from the bacterial genus *Cupriavidus* such as *Cupriavidus necator* or *Cupriavidus metallidurans*; from the bacterial genus *Pseudomonas* such as *Pseudomonas fluorescens*, *Pseudomonas putida* or *Pseudomonas oleavorans*; from the bacterial genus *Delftia* such as *Delftia acidovorans*; from the bacterial genus *Bacillus* such as *Bacillus subtillis*; from the bacterial genus *Lactobacillus* such as *Lactobacillus delbrueckii*; or from the bacterial genus *Lactococcus* such as *Lactococcus lactis*. Such prokaryotes also can be sources of genes for constructing recombinant host cells described herein that are capable of producing C6 building blocks.

In some embodiments, the host microorganism is a eukaryote (e.g., a fungus such as a yeast). For example, the eukaryote can be from the fungal genus *Aspergillus* such as *Aspergillus niger*; from the yeast genus *Saccharomyces* such as *Saccharomyces cerevisiae*; from the yeast genus *Pichia* such as *Pichia pastoris*; from the yeast genus *Yarrowia* such as *Yarrowia lipolytica*; from the yeast genus *Issatchenkia* such as *Issathenkia orientalis*; from the yeast genus *Debaryomyces* such as *Debaryomyces hansenii*; from the yeast genus *Arxula* such as *Arxula adenoinivorans*; or from the yeast genus *Kluyveromyces* such as *Kluyveromyces lactis*. Such eukaryotes also can be sources of genes for constructing recombinant host cells described herein that are capable of producing C6 building blocks.

In some embodiments, the host microorganism's tolerance to high concentrations of one or more C6 building blocks is improved through continuous cultivation in a selective environment.

In some embodiments, the host microorganism's biochemical network is attenuated or augmented to (1) ensure the intracellular availability of acetyl-CoA, (2) create an NADH or NADPH imbalance that may only be balanced via the formation of one or more C6 building blocks, (3) prevent degradation of central metabolites, central precursors leading to and including C6 building blocks and (4) ensure efficient efflux from the cell.

In some embodiments, a non-cyclical cultivation strategy is used to achieve anaerobic, micro-aerobic, or aerobic cultivation conditions.

In some embodiments, a cyclical cultivation strategy is used to alternate between anaerobic and aerobic cultivation conditions.

In some embodiments, the cultivation strategy includes limiting nutrients, such as limiting nitrogen, phosphate or oxygen.

In some embodiments, one or more C6 building blocks are produced by a single type of microorganism, e.g., a recombinant host containing one or more exogenous nucleic acids, using a non-cyclical or cyclical fermentation strategy.

In some embodiments, one or more C6 building blocks are produced by co-culturing more than one type of microorganism, e.g., two or more different recombinant hosts, with each host containing a particular set of exogenous nucleic acids.

In some embodiments, one or more C6 building blocks can be produced by successive fermentations, where the broth or centrate from the preceding fermentation can be fed to a succession of fermentations as a source of feedstock, central metabolite or central precursor; finally producing the C6 building block.

This document also features a recombinant host comprising at least one exogenous nucleic acid encoding, for example, one or more of a formate dehydrogenase, enoyl-CoA reductase, trans-2-enoyl-CoA hydratase, 3-hydroxybutyryl-CoA dehydrogenase, β-ketothiolase, acetoacyl-CoA reductase, acetyl-CoA synthetase, acetyl-CoA carboxylase, a malic enzyme, puridine nucleotide transhydrogenase, glyceraldehyde-3P-dehydrogenase, thioesterase, aldehyde dehydrogenase, monooxygenase, alcohol dehydrogenase, 6-hydroxyhexanoate dehydrogenase, 5-hydroxypentanoate dehydrogenase, 4-hydroxybutyrate dehydrogenase, 6-oxohexanoate dehydrogenase, 7-oxoheptanoate dehydrogenase, ω-transaminase, propionyl-CoA synthetase, and a carboxylate reductase, wherein said host comprises one or more deficiencies, for example, in glucose-6-phosphate isomerase, acetate kinase, an enzyme degrading pyruvate to lactate such as lactate dehydrogenase, enzymes mediating the degradation of phophoenolpyruvate to succinate such as menaquinol-fumarate oxidoreductase, alcohol dehydrogenase, pyruvate decarboxylase, 2-oxoacid decarboxylase, triose phosphate isomerase, or a NADH-specific glutamate dehydrogenase.

In one aspect, this document features a recombinant host that includes at least one exogenous nucleic acid encoding (i) a β-ketothiolase or an acetyl-CoA carboxylase and an acetoacetyl-CoA synthase, (ii) a 3-hydroxyacyl-CoA dehydrogenase or a 3-oxoacyl-CoA reductase, (iii) an enoyl-CoA hydratase, and (iv) a trans-2-enoyl-CoA reductase, where the host produces hexanoyl-CoA. The host further can include one or more of a thioesterase, an aldehyde dehydrogenase, or a butanal dehydrogenase, wherein the host produces hexanal or hexanoate.

A recombinant producing hexanal or hexanoate further can include one or more of a monooxygenase, an alcohol dehydrogenase, an aldehyde dehydrogenase, a 6-hydroxyhexanoate dehydrogenase, a 5-hydroxypentanoate dehydrogenase, a 4-hydroxybutyrate dehydrogenase, a 6-oxohexanoate dehydrogenase, or a 7-oxoheptanoate dehydrogenase, wherein the host produces adipic acid or adipate semialdehyde.

A recombinant producing hexanal or hexanoate further can include one or more of monooxygenase, a transaminase, a 6-hydroxyhexanoate dehydrogenase, a 5-hydroxypentanoate dehydrogenase, a 4-hydroxybutyrate dehydrogenase, and an alcohol dehydrogenase, wherein the host produces 6-aminohexanoate. The host further can include a lactamase and produce caprolactam.

A recombinant producing hexanal or hexanoate further can include a monooxygenase, the host producing 6-hydroxyhexanoic acid.

A recombinant host producing hexanal, hexanoate, 6-hydroxyhexanoate, or 6-aminohexanoate further can include one or more of a carboxylate reductase, a ω-transaminase, a deacetylase, a N-acetyl transferase, or an alcohol dehydrogenase, and produce hexamethylenediamine.

A recombinant host producing 6-hydroxyhexanoate further can include a carboxylate reductase or an alcohol dehydrogenase, the host producing 1,6-hexanediol.

Any of the recombinant hosts described herein further can include one or more of the following attenuated enzymes: a polyhydroxyalkanoate synthase, an acetyl-CoA thioesterase, a phosphotransacetylase forming acetate, an acetate kinase, a lactate dehydrogenase, a menaquinol-fumarate oxidoreductase, a 2-oxoacid decarboxylase producing isobutanol, an alcohol dehydrogenase forming ethanol, a triose phosphate isomerase, a pyruvate decarboxylase, a glucose-6-phosphate isomerase, NADH-consuming transhydrogenase, an NADH-specific glutamate dehydrogenase, a NADH/NADPH-utilizing glutamate dehydrogenase, a pimeloyl-CoA dehydrogenase; an acyl-CoA dehydrogenase accepting C6 building blocks and central precursors as substrates; a butaryl-CoA dehydrogenase; or an adipyl-CoA synthetase.

Any of the recombinant hosts described herein further can overexpress one or more genes encoding: an acetyl-CoA synthetase, a 6-phosphogluconate dehydrogenase; a transketolase; a puridine nucleotide transhydrogenase; a glyceraldehyde-3P-dehydrogenase; a malic enzyme; a glucose-6-phosphate dehydrogenase; a glucose dehydrogenase; a fructose 1,6 diphosphatase; a L-alanine dehydrogenase; a L-glutamate dehydrogenase; a formate dehydrogenase; a L-glutamine synthetase; a diamine transporter; a dicarboxylate transporter; and/or a multidrug transporter.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF DRAWINGS

FIG. 9 contains the amino acid sequences of an *Escherichia coli* thioesterase encoded by tesB (see GenBank Accession No. AAA24665.1, SEQ ID NO: 1), a *Mycobacterium marinum* carboxylate reductase (see Genbank Accession No. ACC40567.1, SEQ ID NO: 2), a *Mycobacterium smegmatis* carboxylate reductase (see Genbank Accession No. ABK71854.1, SEQ ID NO: 3), a *Segniliparus rugosus* carboxylate reductase (see Genbank Accession No. EFV11917.1, SEQ ID NO: 4), a *Mycobacterium massiliense* carboxylate reductase (see Genbank Accession No. EIV11143.1, SEQ ID NO: 5), a *Segniliparus rotundus* carboxylate reductase (see Genbank Accession No. ADG98140.1, SEQ ID NO: 6), a *Chromobacterium violaceum* ω-transaminase (see Genbank Accession No. AAQ59697.1, SEQ ID NO: 7), a *Pseudomonas aeruginosa* ω-transaminase (see Genbank Accession No. AAG08191.1, SEQ ID NO: 8), a *Pseudomonas syringae* ω-transaminase (see Genbank Accession No. AAY39893.1, SEQ ID NO: 9), a *Rhodobacter sphaeroides* ω-transaminase (see Genbank Accession No. ABA81135.1, SEQ ID NO: 10), an *Escherichia coli* ω-transaminase (see Genbank Accession No. AAA57874.1, SEQ ID NO: 11), a *Vibrio Fluvialis* ω-transaminase (See Genbank Accession No. AEA39183.1, SEQ ID NO: 12); a *Polaromonas* sp. JS666 monooxygenase (see Genbank Accession No. ABE47160.1, SEQ ID NO:13), a *Mycobacterium* sp. HXN-1500 monooxygenase (see Genbank Accession No. CAH04396.1, SEQ ID NO:14), a *Mycobacterium austroafricanum* monooxygenase (see Genbank Accession No. ACJ06772.1, SEQ ID NO:15), a *Polaromonas* sp. JS666 oxidoreductase (see Genbank Accession No. ABE47159.1, SEQ ID NO:16), a *Mycobacterium* sp. HXN-1500 oxidoreductase (see Genbank Accession No. CAH04397.1, SEQ ID NO:17), a *Polaromonas* sp. JS666 ferredoxin (see Genbank Accession No. ABE47158.1, SEQ ID NO:18), a *Mycobacterium* sp. HXN-1500 ferredoxin (see Genbank Accession No. CAH04398.1, SEQ ID NO:19), a *Bacillus subtilis* phosphopantetheinyl transferase (see Genbank Accession No. CAA44858.1, SEQ ID NO:20), and a *Nocardia* sp. NRRL 5646 phosphopantetheinyl transferase (see Genbank Accession No. ABI83656.1, SEQ ID NO:21).

DETAILED DESCRIPTION

Figure 1:
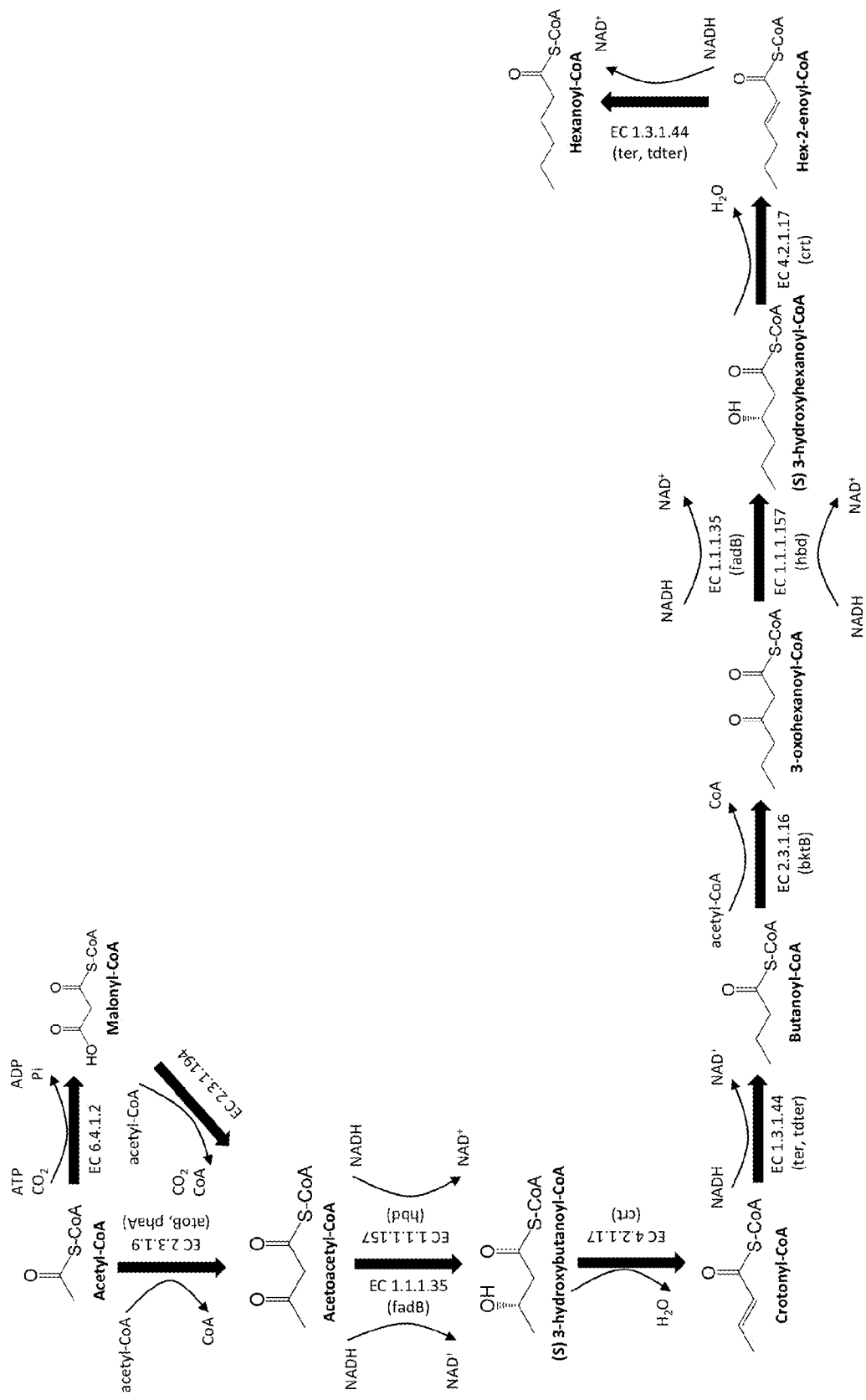
FIG. 1 is a schematic of an exemplary biochemical pathway leading to hexanoyl-CoA using NADH-dependent enzymes and with acetyl-CoA as a central metabolite.

In general, this document provides enzymes, non-natural pathways, cultivation strategies, feedstocks, host microorganisms and attenuations to the host's biochemical network, which generates a six carbon chain aliphatic backbone from central metabolites into which two terminal functional groups may be formed leading to the synthesis of one or more of adipic acid, caprolactam, 6-aminohexanoic acid, 6-hydroxyhexanoic acid, hexamethylenediamine or 1,6-hexanediol (referred to as "C6 building blocks" herein). As used herein, the term "central precursor" is used to denote any metabolite in any metabolic pathway shown herein leading to the synthesis of a C6 building block. The term "central metabolite" is used herein to denote a metabolite that is produced in all microorganisms to support growth.

Host microorganisms described herein can include endogenous pathways that can be manipulated such that one or more C6 building blocks can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

For example, depending on the host and the compounds produced by the host, one or more of the following enzymes may be expressed in the host in addition to (i) a β-ketothioase or an acetyl-CoA carboxylase and acetoacetyl-CoA synthase, (ii) a 3-hydroxyacyl-CoA dehydrogenase or a 3-oxoacyl-CoA reductase, (iii) an enoyl-CoA hydratase, and (iv) a trans-2-enoyl-CoA reductase: a thioesterase, an aldehyde dehydrogenase, a butanal dehydrogenase, a monooxygenase, an alcohol dehydrogenase, a 6-oxohexanoate dehydrogenase, a 7-oxoheptanoate dehydrogenase, a ω transaminase, a 6-hydroxyhexanoate dehydrogenase, a 5-hydroxypentanoate dehydrogenase, a 4-hydroxybutyrate dehydrogenase, a carboxylate reductase, a deacetylase, or an N-acetyl transferase.

In recombinant hosts expressing a carboxylate reductase, a phosphopantetheinyl transferase also can be expressed as it enhances activity of the carboxylate reductase. In recombinant hosts expressing a monooxygenase, an electron transfer chain protein such as an oxidoreductase or ferredoxin polypeptide also can be expressed.

In some embodiments, a recombinant host can include at least one exogenous nucleic acid encoding a β-ketothioase or an acetyl-CoA carboxylase and acetoacetyl-CoA synthase, a 3-hydroxyacyl-CoA dehydrogenase or a 3-oxoacyl-CoA reductase, an enoyl-CoA hydratase, and a trans-2-enoyl-CoA reductase, and produce hexanoyl-CoA. Such a host further can include one or more of (e.g., two or three of) a thioesterase, an aldehyde dehydrogenase, or a butanal dehydrogenase, and produce hexanal or hexanoate.

A recombinant host producing hexanal or hexanoate further can include one or more of a monooxygenase, an alcohol dehydrogenase, an aldehyde dehydrogenase, a 6-hydroxyhexanoate dehydrogenase, a 5-hydroxypentanoate dehydrogenase, a 4-hydroxybutyrate dehydrogenase, a 6-oxohexanoate dehydrogenase, or a 7-oxoheptanoate dehydrogenase, and produce adipic acid or adipate semialdehyde. For example, a recombinant host further can include a monooxygenase and produce adipic acid or adipate semialdehyde. As another example, a recombinant host further can include (i) a monooxygenase, (ii) an alcohol dehydrogenase, a 6-hydroxyhexanoate dehydrogenase, a 5-hydroxypentanoate dehydrogenase or a 4-hydroxybutyrate dehydrogenase and (iii) an aldehyde dehydrogenase, a 6-oxohexanoate dehydrogenase, or a 7-oxoheptanoate dehydrogenase, and produce adipic acid.

A recombinant host producing hexanal or hexanoate further can include one or more of a monooxygenase, a transaminase, a 6-hydroxyhexanoate dehydrogenase, a 5-hydroxypentanoate dehydrogenase, a 4-hydroxybutyrate dehydrogenase, and an alcohol dehydrogenase, and produce 6-aminohexanoate. For example, a recombinant host further can include each of a monooxygenase, a transaminase, and a 6-hydroxyhexanoate dehydrogenase.

A recombinant host producing hexanal or hexanoate further can include a monooxygenase, and produce 6-hydroxyheptanoic acid.

A recombinant host producing 6-aminohexanoate, 6-hydroxyhexanoate, or adipate semialdehyde further can include one or more of a carboxylate reductase, a ω-transaminase, a deacetylase, a N-acetyl transferase, or an alcohol dehydrogenase, and produce hexamethylenediamine. In some embodiments, a recombinant host further can include each of a carboxylate reductase, a ω-transaminase, a deacetylase, and an N-acetyl transferase. In some embodiments, a recombinant host further can include a carboxylate reductase and a ω-transaminase. In some embodiments, a recombinant host further can include a carboxylate reductase, a ω-transaminase, and an alcohol dehydrogenase.

A recombinant host producing 6-hydroxyhexanoic acid further can include one or more of a carboxylate reductase and an alcohol dehydrogenase, and produce 1,6-hexanediol.

Within an engineered pathway, the enzymes can be from a single source, i.e., from one species or genera, or can be from multiple sources, i.e., different species or genera. Nucleic acids encoding the enzymes described herein have been identified from various organisms and are readily available in publicly available databases such as GenBank or EMBL.

Any of the enzymes described herein that can be used for production of one or more C6 building blocks can have at least 70% sequence identity (homology) (e.g., at least 75%, 80%, 85%, 90%, 95%, 97%, 98%, 99%, or 100%) to the amino acid sequence of the corresponding wild-type enzyme. For example, a thioesterase described herein can have at least 70% sequence identity (homology) (e.g., at least 75%, 80%, 85%, 90%, 95%, 97%, 98%, 99%, or 100%) to the amino acid sequence of an *Escherichia coli* thioesterase encoded by tesB (see GenBank Accession No. AAA24665.1, SEQ ID NO: 1). See FIG. 9.

For example, a carboxylate reductase described herein can have at least 70% sequence identity (homology) (e.g., at least 75%, 80%, 85%, 90%, 95%, 97%, 98%, 99%, or 100%) to the amino acid sequence of a *Mycobacterium marinum* (see Genbank Accession No. ACC40567.1, SEQ ID NO: 2), a *Mycobacterium smegmatis* (see Genbank Accession No. ABK71854.1, SEQ ID NO: 3), a *Segniliparus rugosus* (see Genbank Accession No. EFV11917.1, SEQ ID NO: 4), a *Mycobacterium massiliense* (see Genbank Accession No. EIV 11143.1, SEQ ID NO: 5), or a *Segniliparus rotundus* (see Genbank Accession No. ADG98140.1, SEQ ID NO: 6) carboxylate reductase. See, FIG. 9.

For example, a ω-transaminase described herein can have at least 70% sequence identity (homology) (e.g., at least 75%, 80%, 85%, 90%, 95%, 97%, 98%, 99%, or 100%) to the amino acid sequence of a *Chromobacterium violaceum* (see Genbank Accession No. AAQ59697.1, SEQ ID NO: 7), a *Pseudomonas aeruginosa* (see Genbank Accession No. AAG08191.1, SEQ ID NO: 8), a *Pseudomonas syringae* (see Genbank Accession No. AAY39893.1, SEQ ID NO: 9), a *Rhodobacter sphaeroides* (see Genbank Accession No. ABA81135.1, SEQ ID NO: 10), an *Escherichia coli* (see Genbank Accession No. AAA57874.1, SEQ ID NO: 11), or a *Vibrio fluvialis* (see Genbank Accession No. AEA39183.1, SEQ ID NO: 12) ω-transaminase. Some of these w-transaminases are diamine ω-transaminases. See, FIG. 9.

For example, a monooxygenase described herein can have at least 70% sequence identity (homology) (e.g., at least 75%, 80%, 85%, 90%, 95%, 97%, 98%, 99%, or 100%) to the amino acid sequence of a *Polaromonas* sp. JS666 monooxygenase (see Genbank Accession No. ABE47160.1, SEQ ID NO:13), a *Mycobacterium* sp. HXN-1500 monooxygenase (see Genbank Accession No. CAH04396.1, SEQ ID NO:14), or a *Mycobacterium austroafricanum* monooxygenase (see Genbank Accession No. ACJ06772.1, SEQ ID NO:15). See, FIG. 9.

For example, an oxidoreductase described herein can have at least 70% sequence identity (homology) (e.g., at least 75%, 80%, 85%, 90%, 95%, 97%, 98%, 99%, or 100%) to the amino acid sequence of a *Polaromonas* sp. JS666 oxidoreductase (see Genbank Accession No. ABE47159.1, SEQ ID NO:16) or a *Mycobacterium* sp. HXN-1500 oxidoreductase (see Genbank Accession No. CAH04397.1, SEQ ID NO:17). See, FIG. 9.

For example, a ferredoxin polypeptide described herein can have at least 70% sequence identity (homology) (e.g., at least 75%, 80%, 85%, 90%, 95%, 97%, 98%, 99%, or 100%) to the amino acid sequence of a *Polaromonas* sp. JS666 ferredoxin (see Genbank Accession No. ABE47158.1, SEQ ID NO:18) or a *Mycobacterium* sp. HXN-1500 ferredoxin (see Genbank Accession No. CAH04398.1, SEQ ID NO:19). See, FIG. 9.

For example, a phosphopantetheinyl transferase described herein can have at least 70% sequence identity (homology) (e.g., at least 75%, 80%, 85%, 90%, 95%, 97%, 98%, 99%, or 100%) to the amino acid sequence of a *Bacillus subtilis* phosphopantetheinyl transferase (see Genbank Accession No. CAA44858.1, SEQ ID NO: 20) or a *Nocardia* sp. NRRL 5646 phosphopantetheinyl transferase (see Genbank Accession No. ABI83656.1, SEQ ID NO:21). See, FIG. 9.

The percent identity (homology) between two amino acid sequences can be determined as follows. First, the amino acid sequences are aligned using the BLAST 2 Sequences (Bl2seq) program from the stand-alone version of BLASTZ containing BLASTP version 2.0.14. This stand-alone version of BLASTZ can be obtained from Fish & Richardson's web site (e.g., www.fr.com/blast/) or the U.S. government's National Center for Biotechnology Information web site (www.ncbi.nlm.nih.gov). Instructions explaining how to use the Bl2seq program can be found in the readme file accompanying BLASTZ. Bl2seq performs a comparison between two amino acid sequences using the BLASTP algorithm. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 78.11, 78.12, 78.13, and 78.14 is rounded down to 78.1, while 78.15, 78.16, 78.17, 78.18, and 78.19 is rounded up to 78.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the enzymes described herein can also be used in the methods of the document. The term "functional fragment" as used herein refers to a peptide fragment of a protein that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, wild-type protein. The functional fragment can generally, but not always, be comprised of a continuous region of the protein, wherein the region has functional activity.

This document also provides (i) functional variants of the enzymes used in the methods of the document and (ii) functional variants of the functional fragments described above. Functional variants of the enzymes and functional fragments can contain additions, deletions, or substitutions relative to the corresponding wild-type sequences. Enzymes with substitutions will generally have not more than 50 (e.g., not more than one, two, three, four, five, six, seven, eight, nine, ten, 12, 15, 20, 25, 30, 35, 40, or 50) amino acid substitutions (e.g., conservative substitutions). This applies to any of the enzymes described herein and functional fragments. A conservative substitution is a substitution of one amino acid for another with similar characteristics. Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The nonpolar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution. By contrast, a nonconservative substitution is a substitution of one amino acid for another with dissimilar characteristics.

Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Additions (addition variants) include fusion proteins containing: (a) any of the enzymes described herein or a fragment thereof; and (b) internal or terminal (C or N) irrelevant or heterologous amino acid sequences. In the context of such fusion proteins, the term "heterologous amino acid sequences" refers to an amino acid sequence other than (a). A heterologous sequence can be, for example a sequence used for purification of the recombinant protein (e.g., FLAG, polyhistidine (e.g., hexahistidine), hemagglutinin (HA), glutathione-S-transferase (GST), or maltosebinding protein (MBP)). Heterologous sequences also can be proteins useful as detectable markers, for example, luciferase, green fluorescent protein (GFP), or chloramphenicol acetyl transferase (CAT). In some embodiments, the fusion protein contains a signal sequence from another protein. In certain host cells (e.g., yeast host cells), expression and/or secretion of the target protein can be increased through use of a heterologous signal sequence. In some embodiments, the fusion protein can contain a carrier (e.g., KLH) useful, e.g., in eliciting an immune response for antibody generation) or ER or Golgi apparatus retention signals. Heterologous sequences can be of varying length and in some cases can be a longer sequences than the full-length target proteins to which the heterologous sequences are attached.

Engineered hosts can naturally express none or some (e.g., one or more, two or more, three or more, four or more, five or more, or six or more) of the enzymes of the pathways described herein. Thus, a pathway within an engineered host can include all exogenous enzymes, or can include both endogenous and exogenous enzymes. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. As described herein recombinant hosts can include nucleic acids encoding one or more of a dehydrogenase, a β-ketothiolase, a acetoacetyl-CoA synthase, a carboxylase, a reductase, a hydratase, a thioesterase, a monooxygenase, a thioesterase, or transaminase as described herein.

In addition, the production of C6 building blocks can be performed in vitro using the isolated enzymes described herein, using a lysate (e.g., a cell lysate) from a host microorganism as a source of the enzymes, or using a plurality of lysates from different host microorganisms as the source of the enzymes.

The reactions of the pathways described herein can be performed in one or more host strains (a) naturally expressing one or more relevant enzymes, (b) genetically engineered to express one or more relevant enzymes, or (c) naturally expressing one or more relevant enzymes and genetically engineered to express one or more relevant enzymes. Alternatively, relevant enzymes can be extracted from of the above types of host cells and used in a purified or semi-purified form. Moreover, such extracts include lysates (e.g. cell lysates) that can be used as sources of relevant enzymes. In the methods provided by the document, all the steps can be performed in host cells, all the steps can be performed using extracted enzymes, or some of the steps can be performed in cells and others can be performed using extracted enzymes.

Figure 2:
FIG. 2 is a schematic of an exemplary biochemical pathway leading to hexanoyl-CoA using NADPH-dependent enzymes and with acetyl-CoA as a central metabolite.

Enzymes Generating the C6 Aliphatic Backbone for Conversion to C6 Building Blocks As depicted in FIG. 1 and FIG. 2, the C6 aliphatic backbone for conversion to C6 building blocks can be formed from acetyl-CoA via two cycles of CoA-dependent carbon chain elongation using either NADH or NADPH dependent enzymes.

In some embodiments, a CoA-dependent carbon chain elongation cycle comprises a β-ketothiolase or an acetyl-CoA carboxylase and an acetoacetyl-CoA synthase, a 3-hydroxyacyl-CoA dehydrogenase or 3-oxoacyl-CoA reductase, an enoyl-CoA hydratase and a trans-2-enoyl-CoA reductase. A β-ketothiolase can convert acetyl-CoA to acetoacetyl-CoA and can convert butanoyl-CoA to 3-oxohexanoyl-CoA. Acetyl-CoA carboxylase can convert acetyl-CoA to malonyl-CoA. An acetoacetyl-CoA synthase can convert malonyl-CoA to acetoacetyl-CoA. A 3-hydroxybutyryl-CoA dehydrogenase can convert acetoacetyl-CoA to 3-hydroxybutanoyl CoA. A 3-oxoacyl-CoA reductase/3-hydroxyacyl-CoA dehydrogenase can convert 3-oxohexanoyl-CoA to 3-hydroxyhexanoyl-CoA. An enoyl-CoA hydratase can convert 3-hydroxybutanoyl-CoA to crotonyl-CoA and can convert 3-hydroxyhexanoyl-CoA to hex-2-enoyl-CoA. A trans-2-enoyl-CoA reductase can convert crotonyl-CoA to butanoyl-CoA and can convert hex-2-enoyl-CoA to hexanoyl-CoA.

In some embodiments, a β-ketothiolase may be classified under EC 2.3.1.9, such as the gene product of atoB or phaA, or classified under EC 2.3.1.16, such as the gene product of bktB. The β-ketothiolase encoded by bktB from *Cupriavidus necator* accepts acetyl-CoA and butanoyl-CoA as substrates, forming the CoA-activated C6 aliphatic backbone (see, e.g., Haywood et al., *FEMS Microbiology Letters*, 1988, 52:91-96; Slater et al., *J. Bacteriol.*, 1998, 180(8):1979-1987). The β-ketothiolase encoded by atoB or phaA accepts acetyl-CoA as substrates, forming butanoyl-CoA (see, Haywood et al., 1988, supra; Slater et al., 1998, supra).

In some embodiments, an acetyl-CoA carboxylase can be classified, for example, under EC 6.4.1.2. Conversion of acetyl-CoA to malonyl-CoA by an acetyl-CoA carboxylase has been shown to increase the rate of fatty acid synthesis (Davis et al., *J. Biol. Chem.*, 2000, 275(37), 28593-28598).

In some embodiments, an acetoacetyl-CoA synthase may be classified under EC 2.3.1.194. It has been demonstrated that acetoacetyl-CoA synthase may be used as an irreversible substitute for the gene product of phaA in the carbon chain elongation associated with polyhydroxybutyrate synthesis (Matsumoto et al., *Biosci. Biotechnol. Biochem.*, 2011, 75(2), 364-366).

In some embodiments, a 3-hydroxyacyl-CoA dehydrogenase or 3-oxoacyl-CoA dehydrogenase can be classified under EC 1.1.1.-. For example, the 3-hydroxyacyl-CoA dehydrogenase can be classified under EC 1.1.1.35, such as the gene product of fadB; classified under EC 1.1.1.157, such as the gene product of hbd (also can be referred to as a 3-hydroxybutyryl-CoA dehydrogenase); or classified under EC 1.1.1.36, such as the acetoacetyl-CoA reductase gene product of phaB (Liu & Chen, *Appl. Microbiol. Biotechnol.*, 2007, 76(5):1153-1159; Shen et al., *Appl. Environ. Microbiol.*, 2011, 77(9):2905-2915; Budde et al., *J. Bacteriol.*, 2010, 192(20):5319-5328).

In some embodiments, a 3-oxoacyl-CoA reductase can be classified under EC 1.1.1.100, such as the gene product of fabG (Budde et al., *J. Bacteriol.*, 2010, 192(20):5319-5328; Nomura et al., *Appl. Environ. Microbiol.*, 2005, 71(8):4297-4306).

In some embodiments, an enoyl-CoA hydratase can be classified under EC 4.2.1.17, such as the gene product of crt, or classified under EC 4.2.1.119, such as the gene product of phaJ (Shen et al., 2011, supra; Fukui et al., *J. Bacteriol.*, 1998, 180(3):667-673).

In some embodiments, a trans-2-enoyl-CoA reductase can be classified under EC 1.3.1.38, EC 1.3.1.8, or EC 1.3.1.44, such as the gene product of ter (Nishimaki et al., *J. Biochem.*, 1984, 95:1315-1321; Shen et al., 2011, supra) or tdter (Bond-Watts et al., *Biochemistry*, 2012, 51:6827-6837).

Figure 3:
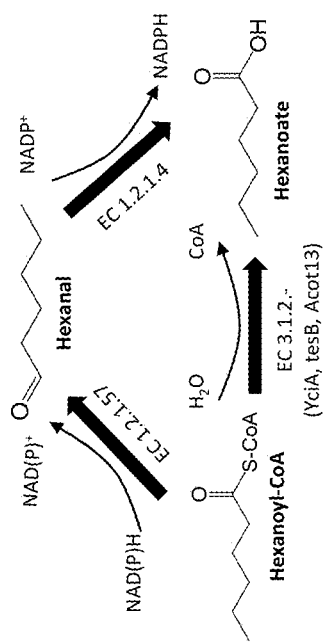
FIG. 3 is a schematic of exemplary biochemical pathways leading to hexanoate using hexanoyl-CoA as a central precursor.
Figure 4:
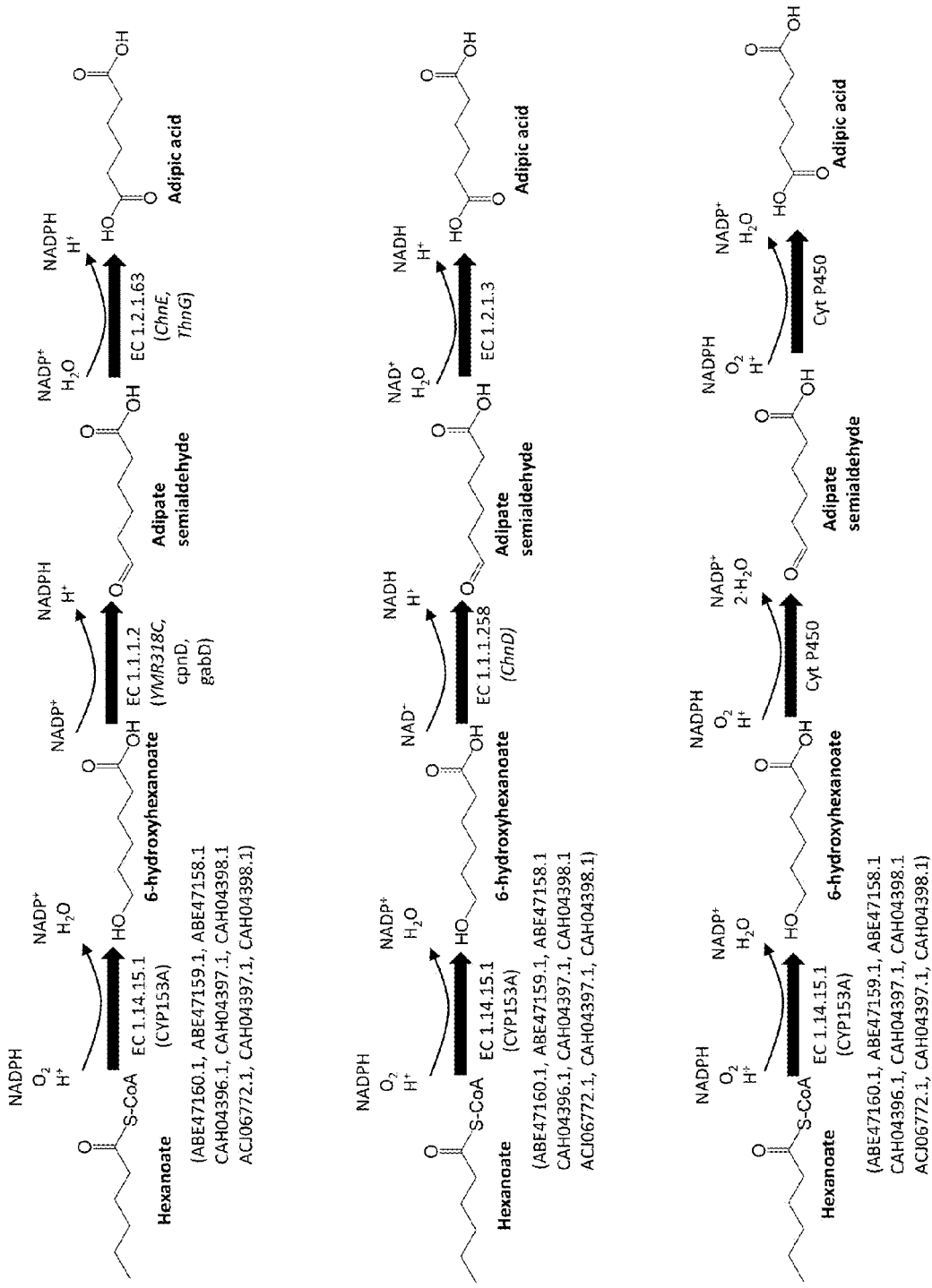
FIG. 4 is a schematic of exemplary biochemical pathways leading to adipic acid using hexanoate as a central precursor.

Enzymes Generating the Terminal Carboxyl Groups in the Biosynthesis of C6 Building Blocks As depicted in FIG. 3 and FIG. 4, the terminal carboxyl groups can be enzymatically formed using a thioesterase, an aldehyde dehydrogenase, a 6-oxohexanoate dehydrogenase, a 7-oxoheptanoate dehydrogenase, or a monooxygenase.

In some embodiments, the first terminal carboxyl group leading to the synthesis of a C6 building block is enzymatically formed in hexanoyl-CoA by a thioesterase classified under EC 3.1.2.-, resulting in the production of hexanoate. The thioesterase can be the gene product of YciA, tesB or Acot13 (Cantu et al., *Protein Science*, 2010, 19, 1281-1295; Zhuang et al., *Biochemistry*, 2008, 47(9):2789-2796; Naggert et al., *J. Biol. Chem.*, 1991, 266(17):11044-11050).

In some embodiments, the first terminal carboxyl group leading to the synthesis of a C6 building block can be enzymatically formed in hexanal by an aldehyde dehydrogenase classified under EC 1.2.1.4 (see, Ho & Weiner, *J. Bacteriol.*, 2005, 187(3):1067-1073), resulting in the production of hexanoate.

In some embodiments, the second terminal carboxyl group leading to the synthesis of adipic acid can be enzymatically formed in adipate semialdehyde by an aldehyde dehydrogenase classified under EC 1.2.1.3 (Guerrillot & Vandecasteele, *Eur. J. Biochem.*, 1977, 81, 185-192).

In some embodiments, the second terminal carboxyl group leading to the synthesis of adipic acid is enzymatically formed in adipate semialdehyde by a 6-oxohexanoate dehydrogenase such as the gene product of ChnE from *Acinetobacter* sp. or 7-oxoheptanoate dehydrogenase such as the gene product of ThnG from *Sphingomonas macrogolitabida* (Iwaki et al., *Appl. Environ. Microbiol.*, 1999, 65(11), 5158-5162; López-Sánchez et al., *Appl. Environ. Microbiol.*, 2010, 76(1), 110-118)). For example, a 6-oxohexanoate dehydrogenase can be classified under EC 1.2.1.63. For example, a 7-oxoheptanoate dehydrogenase can be classified under EC 1.2.1.-

In some embodiments, the second terminal carboxyl group leading to the synthesis of adipic acid is enzymatically formed in adipate semialdehyde by a monooxygenase in the cytochrome P450 family such as CYP4F3B (see, e.g., Sanders et al., *J. Lipid Research*, 2005, 46(5):1001-1008; Sanders et al., *The FASEB Journal*, 2008, 22(6):2064-2071).

The utility of ω-oxidation in introducing carboxyl groups into alkanes has been demonstrated in the yeast *Candida tropicalis*, leading to the synthesis of adipic acid (Okuhara et al., *Agr. Biol. Chem.*, 1971, 35(9), 1376-1380).

Figure 5:
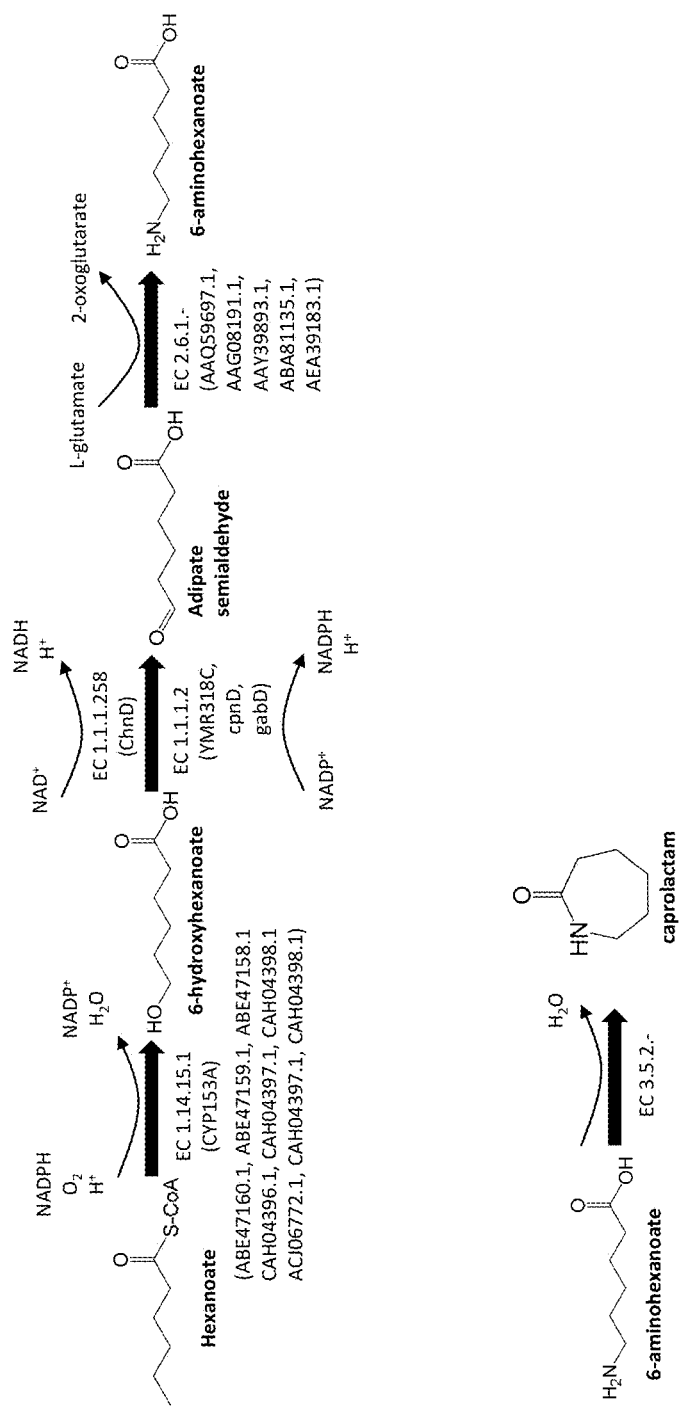
FIG. 5 is a schematic of an exemplary biochemical pathway leading to 6-aminhexanoate using hexanoate as a central precursor and a schematic of an exemplary biochemical pathway leading to caprolactam from 6-aminohexanoate.
Figure 6:
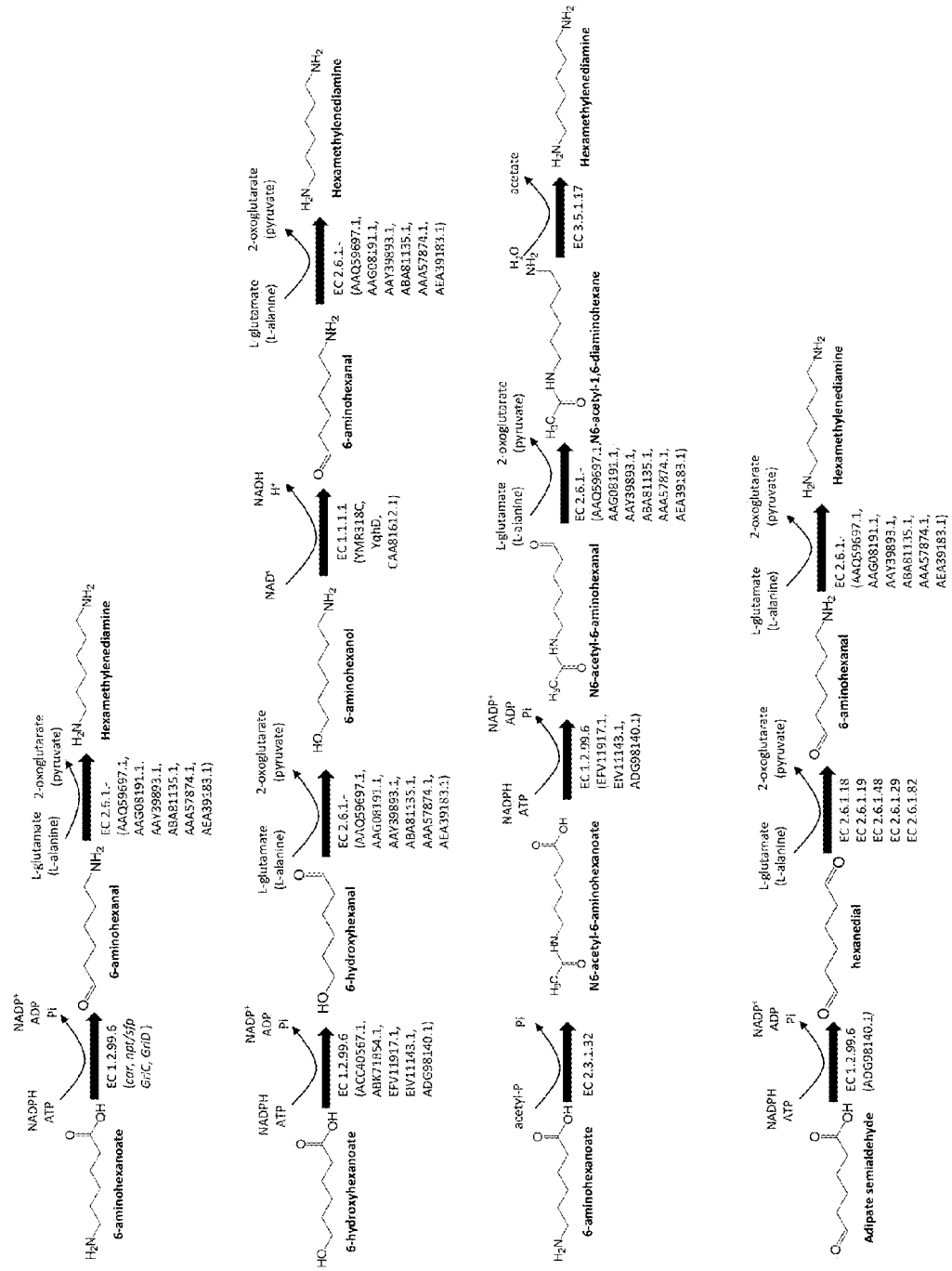
FIG. 6 is a schematic of exemplary biochemical pathways leading to hexamethylenediamine using 6-aminohexanoate, 6-hydroxyhexanoate, or adipate semialdehyde as a central precursor.

Enzymes Generating the Terminal Amine Groups in the Biosynthesis of C6 Building Blocks As depicted in FIG. 5 and FIG. 6, terminal amine groups can be enzymatically formed using a ω-transaminase or a deacetylase.

In some embodiments, the first terminal amine group leading to the synthesis of 6-aminohexanoic acid is enzymatically formed in adipate semialdehyde by a ω-transaminase classified, for example, under EC 2.6.1.18, EC 2.6.1.19, EC 2.6.1.29, EC 2.6.1.48, or EC 2.6.1.82 such as that obtained from *Chromobacterium violaceum* (Genbank Accession No. AAQ59697.1, SEQ ID NO: 7), *Pseudomonas aeruginosa* (Genbank Accession No. AAG08191.1, SEQ ID NO: 8), *Pseudomonas syringae* (Genbank Accession No. AAY39893.1, SEQ ID NO: 9), *Rhodobacter sphaeroides* (Genbank Accession No. ABA81135.1, SEQ ID NO: 10), *Vibrio Fluvialis* (Genbank Accession No. AAA57874.1, SEQ ID NO: 11), *Streptomyces griseus*, or *Clostridium viride*. An additional ω-transaminase that can be used in the methods and hosts described herein is from *Escherichia coli* (Genbank Accession No. AAA57874.1, SEQ ID NO: 11). Some of the ω-transaminases classified, for example, under EC 2.6.1.29 or EC 2.6.1.82 are diamine ω-transaminases (e.g., SEQ ID NO:11).

The reversible ω-transaminase from *Chromobacterium violaceum* (Genbank Accession No. AAQ59697.1, SEQ ID NO: 7) has demonstrated analogous activity accepting 6-aminohexanoic acid as amino donor, thus forming the first terminal amine group in adipate seminaldehyde (Kaulmann et al., *Enzyme and Microbial Technology*, 2007, 41, 628-637).

The reversible 4-aminobubyrate:2-oxoglutarate transaminase from *Streptomyces griseus* has demonstrated activity for the conversion of 6-aminohexanoate to adipate semialdehyde (Yonaha et al., *Eur. J. Biochem.*, 1985, 146, 101-106).

The reversible 5-aminovalerate transaminase from *Clostridium viride* has demonstrated activity for the conversion of 6-aminohexanoate to adipate semialdehyde (Barker et al., *J. Biol. Chem.*, 1987, 262(19), 8994-9003).

In some embodiments, the second terminal amine group leading to the synthesis of hexamethylenediamine is enzymatically formed in 6-aminohexanal by a diamine transaminase classified, for example, under EC 2.6.1.29 or classified, for example, under EC 2.6.1.82, such as the gene product of YgjG from *E. coli* (Genbank Accession No. AAA57874.1, SEQ ID NO: 12).

The gene product of ygjG accepts a broad range of diamine carbon chain length substrates, such as putrescine, cadaverine and spermidine (Samsonova et al., *BMC Microbiology*, 2003, 3:2).

The diamine transaminase from *E. coli* strain B has demonstrated activity for 1,7 diaminoheptane (Kim, *The Journal of Chemistry*, 1964, 239(3), 783-786).

In some embodiments, the second terminal amine group leading to the synthesis of heptamethylenediamine is enzymatically formed by a deacetylase classified, for example, under EC 3.5.1.62 such as an acetylputrescine deacetylase. The acetylputrescine deacetylase from *Micrococcus luteus* K-11 accepts a broad range of carbon chain length substrates, such as acetylputrescine, acetylcadaverine and $N^8$-acetyl-spermidine (see, for example, Suzuki et al., 1986, BBA—General Subjects, 882(1):140-142).

Figure 7:
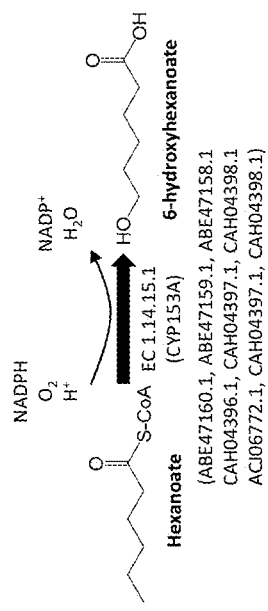
FIG. 7 is a schematic of an exemplary biochemical pathway leading to 6-hydroxyhexanoate using hexanoate as a central precursor.
Figure 8:
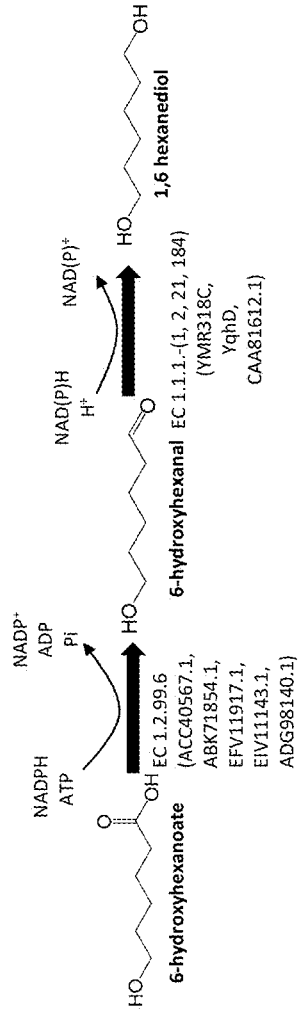
FIG. 8 is a schematic of an exemplary biochemical pathway leading to 1,6-hexanediol using 6-hydroxyhexanoate as a central precursor.

Enzymes Generating the Terminal Hydroxyl Groups in the Biosynthesis of C6 Building Blocks As depicted in FIG. 7 and FIG. 8, the terminal hydroxyl group can be enzymatically forming using a monooxygenase or an alcohol dehydrogenase.

In some embodiments, the first terminal hydroxyl group leading to the synthesis of C6 building blocks is enzymatically formed in hexanoate by a monooxygenase. For example, the monooxygenase CYP153A family classified, for example, under EC 1.14.15.1, is soluble and has regiospecificity for terminal hydroxylation, accepting medium chain length substrates (see, e.g., Koch et al., 2009, *Appl. Environ. Microbiol.*, 75(2): 337-344; Funhoff et al., 2006, *J. Bacteriol.*, 188(44): 5220-5227; Van Beilen & Funhoff, *Current Opinion in Biotechnology*, 2005, 16, 308-314; Nieder and Shapiro, *J. Bacteriol.*, 1975, 122(1), 93-98). Although non-terminal hydroxylation is observed in vitro for CYP153A, in vivo only 1-hydroxylation occurs (Funhoff et al., *J. Bacteriol.*, 2006, 188(14), 5220-5227).

The substrate specificity and activity of terminal monooxygenases has been broadened via successfully, reducing the chain length specificity of CYP153A6 to below C8 (Koch et al., 2009, supra).

In some embodiments, the second terminal hydroxyl group leading to the synthesis of 1,6 hexanediol is enzymatically formed in 6-hydroxyhexanal by an alcohol dehydrogenase classified under EC 1.1.1.- (e.g., EC 1.1.1.1, 1.1.1.2, 1.1.1.21, or 1.1.1.184).

Biochemical Pathways

Pathways to Hexanoyl-CoA as Precursor Leading to Central Precursors to C6 Building Blocks In some embodiments, hexanoyl-CoA is synthesized from the central metabolite, acetyl-CoA, by conversion of acetyl-CoA to acetoacetyl-CoA by an acetoacetyl-CoA thiolase classified, for example, under EC 2.3.1.9, such as the gene product of atoB or phaA, or by an acetyl-CoA carboxylase classified, for example, under EC 6.4.1.2 and an acetoacetyl-CoA synthase classified, for example, under EC 2.3.1.194 via malonyl-CoA; followed by conversion of acetoacetyl-CoA to (S) 3-hydroxybutanoyl-CoA by a 3-hydroxybutyryl-CoA dehydrogenase classified, for example, under EC 1.1.1.35, such as the gene product of fadB or classified, for example, under EC 1.1.1.157 such as the gene product of hbd; followed by conversion of (S) 3-hydroxybutanoyl-CoA to crotonyl-CoA by an enoyl-CoA hydratase classified, for example, under EC 4.2.1.17 such as the gene product of crt; followed by conversion of crotonyl-CoA to butanoyl-CoA by a trans-2-enoyl-CoA reductase classified, for example, under EC 1.3.1.44 such as the gene product of ter or tdter; followed by conversion of butanoyl-CoA to 3-oxo-hexanoyl-CoA by a β-ketothiolase classified, for example, under EC 2.3.1.16 such as the gene product of bktB; followed by conversion of 3-oxo-hexanoyl-CoA to (S) 3-hydroxyhexanoyl-CoA by a 3-hydroxyacyl-CoA dehydrogenase classified, for example, under EC 1.1.1.35 such as the gene product of fadB or classified, for example, under EC 1.1.1.157 such as the gene product of hbd; followed by conversion of (S) 3-hydroxyhexanoyl-CoA to hex-2-enoyl-CoA by an enoyl-CoA hydratase classified, for example, under EC 4.2.1.17 such as the gene product of crt; followed by conversion of hex-2-enoyl-CoA to hexanoyl-CoA by a trans-2-enoyl-CoA reductase classified, for example, under EC 1.3.1.44 such as the gene product of ter or tdter. See FIG. 1.

In some embodiments, hexanoyl-CoA is synthesized from the central metabolite, acetyl-CoA, by conversion of acetyl- CoA to acetoacetyl-CoA by an acetoacetyl-CoA thiolase classified, for example, under EC 2.3.1.9, such as the gene product of atoB or phaA, or by an acetyl-CoA carboxylase classified, for example, under EC 6.4.1.2 & an acetoacetyl-CoA synthase classified, for example, under EC 2.3.1.194 via malonyl-CoA; followed by conversion of acetoacetyl-CoA to (R) 3-hydroxybutanoyl-CoA by a 3-acetoacetyl-CoA reductase classified, for example, under EC 1.1.1.36 such as the gene product of phaB or classified, for example, under EC 1.1.1.100, such as the gene product of fabG; followed by conversion of (R) 3-hydroxybutanoyl-CoA to crotonyl-CoA by an enoyl-CoA hydratase classified, for example, under EC 4.2.1.119 such as the gene product of phaJ; followed by conversion of crotonyl-CoA to butanoyl-CoA by a trans-2-enoyl-CoA reductase classified, for example, under EC 1.3.1.38 or an acyl-dehydrogenase classified, for example, under EC 1.3.1.8; followed by conversion of butanoyl-CoA to 3-oxo-hexanoyl-CoA by a β-ketothiolase classified, for example, under EC 2.3.1.16 such as the gene product of bktB; followed by conversion of 3-oxo-hexanoyl-CoA to (R) 3-hydroxyhexanoyl-CoA by a 3-oxoacyl-CoA reductase classified, for example, under EC 1.1.1.36 such as the gene product of phaB or classified, for example, under EC 1.1.1.100 such as the gene product of fabG; followed by conversion of (R) 3-hydroxyhexanoyl-CoA to hex-2-enoyl-CoA by an enoyl-CoA hydratase classified, for example, under EC 4.2.1.119 such as the gene product of phaJ; followed by conversion of hex-2-enoyl-CoA to hexanoyl-CoA by a trans-2-enoyl-CoA reductase classified, for example, under EC 1.3.1.38 or an acyl-CoA dehydrogenase classified, for example, under EC 1.3.1.8. See FIG. 2.

Pathways Using Hexanoyl-CoA as Precursor Leading to the Central Precursor Hexanoate In some embodiments, hexanoate is synthesized from the central metabolite, hexanoyl-CoA, by conversion of hexanoyl-CoA to hexanoate by a thioesterase classified, for example, under EC 3.1.2.- such as the gene product of YciA, tesB or Acot13.

In some embodiments, hexanoate is synthesized from the central metabolite, hexanoyl-CoA, by conversion of hexanoyl-CoA to hexanal by a butanal dehydrogenase classified, for example, under EC 1.2.1.57; followed by conversion of hexanal to hexanoate by an aldehyde dehydrogenase classified, for example, under EC 1.2.1.4. See FIG. 3.

The conversion of hexanoyl-CoA to hexanal has been demonstrated for both NADH and NADPH as co-factors (Palosaari and Rogers, *J. Bacteriol.*, 1988, 170(7), 2971-2976).

Pathways Using Hexanoate as Central Precursor to Adipic Acid

In some embodiments, adipic acid is synthesized from the central precursor, hexanoate, by conversion of hexanoate to 6-hydroxyhexanoate by a monooxygenase (e.g., cytochrome P450 such as from the CYP153 family (e.g., CYP153A6); followed by conversion of 6-hydroxyhexanoate to adipate semialdehyde by an alcohol dehydrogenase classified under EC 1.1.1.- such as the gene product of YMR318C (classified, for example, under EC 1.1.1.2, see Genbank Accession No. CAA90836.1) (Larroy et al., 2002, *Biochem J.*, 361(Pt 1), 163-172), cpnD (Iwaki et al., 2002, *Appl. Environ. Microbiol.*, 68(11):5671-5684) or gabD (Lütke-Eversloh & Steinbüchel, 1999, *FEMS Microbiology Letters*, 181(1):63-71) or a 6-hydroxyhexanoate dehydrogenase classified, for example, under EC 1.1.1.258 such as the gene product of ChnD (Iwaki et al., *Appl. Environ. Microbiol.*, 1999, 65(11): 5158-5162); followed by conversion of adipate semialdehyde to adipic acid by a dehydrogenase classified, for example, under EC 1.2.1.- such as a 7-oxoheptanoate dehydrogenase (e.g., the gene product of ThnG), a 6-oxohexanoate dehydrogenase (e.g., the gene product of ChnE), or an aldehyde dehydrogenase classified under EC 1.2.1.3. See FIG. 4. The alcohol dehydrogenase encoded by YMR318C has broad substrate specificity, including the oxidation of C6 alcohols.

In some embodiments, adipic acid is synthesized from the central precursor, hexanoate, by conversion of hexanoate to 6-hydroxyhexanoate by a monooxygenase (e.g., cytochrome P450) such as from the CYP153 (e.g., CYP153A); followed by conversion of 6-hydroxyhexanoate to adipate semialdehyde by a cytochrome P450 (Sanders et al., *J. Lipid Research*, 2005, 46(5), 1001-1008; Sanders et al., *The FASEB Journal*, 2008, 22(6), 2064-2071); followed by conversion of adipate semialdehyde to adipic acid by a monooxygenase in the cytochrome P450 family such as CYP4F3B. See FIG. 4.

Pathway Using Hexanoate as Central Precursor to 6-Aminohexanoate and ε-Caprolactam In some embodiments, 6-aminohexanoate is synthesized from the central precursor, hexanoate, by conversion of hexanoate to 6-hydroxyhexanoate by a monooxygenase e.g., cytochrome P450 such as from the CYP153 family (e.g., CYP153A6); followed by conversion of 6-hydroxyhexanoate to adipate semialdehyde by an alcohol dehydrogenase classified, for example, under EC 1.1.1.2 such as the gene product of YMR318C, a 6-hydroxyhexanoate dehydrogenase classified, for example, under EC 1.1.1.258, a 5-hydroxypentanoate dehydrogenase classified, for example, under EC 1.1.1.- such as the gene product of cpnD, or a 4-hydroxybutyrate dehydrogenase classified, for example, under EC 1.1.1.- such as the gene product of gabD; followed by conversion of adipate semialdehyde to 6-aminohexanoate by a ω-transaminase (EC 2.6.1.18, EC 2.6.1.19, EC 2.6.1.29, EC 2.6.1.48, or EC 2.6.1.82 such as SEQ ID NOs:7-12, see above). See FIG. 5.

In some embodiments, ε-caprolactam is synthesized from the central precursor, hexanoate, by conversion of hexanoate to 6-hydroxyhexanoate by a monooxygenase such as from the CYP153 family (e.g., CYP153A); followed by conversion of 6-hydroxyhexanoate to adipate semialdehyde by an alcohol dehydrogenase classified, for example, under EC 1.1.1.2 such as the gene product of YMR318C, a 6-hydroxyhexanoate dehydrogenase classified, for example, under EC 1.1.1.258, a 5-hydroxypentanoate dehydrogenase classified, for example, under EC 1.1.1.- such as the gene product of cpnD, or a 4-hydroxybutyrate dehydrogenase classified, for example, under EC 1.1.1.- such as the gene product of gabD; followed by conversion of adipate semialdehyde to 6-aminohexanoate by a ω-transaminase (EC 2.6.1.18, EC 2.6.1.19, EC 2.6.1.29, EC 2.6.1.48, or EC 2.6.1.82); followed by conversion of 6-aminohexanoate to ε-caprolactam by a hydrolase (EC 3.5.2.-). See FIG. 5.

Pathway Using 6-Aminohexanoate, 6-Hydroxyhexanoate, or Adipate Semialdehyde as a Central Precursor to Hexamethylenediamine In some embodiments, hexamethylenediamine is synthesized from the central precursor, 6-aminohexanoate, by conversion of 6-aminohexanoate to 6-aminohexanal by a carboxylate reductase classified, for example, under EC 1.2.99.6 such as the gene product of car in combination with a phosphopantetheine transferase enhancer (e.g., encoded by a sfp gene from *Bacillus subtilis* or npt gene from *Nocardia*) or the gene products of GriC and GriD from *Streptomyces griseus* (Suzuki et al., *J. Antibiot.*, 2007, 60(6), 380-387); followed by conversion of 6-aminohexanal to hexamethylenediamine by a ω-transaminase (e.g., EC 2.6.1.18, EC 2.6.1.19, EC 2.6.1.48, EC 2.6.1.82 such as SEQ ID NOs:7-12). The carboxylate reductase can be obtained, for example, from *Mycobacterium* marinum (Genbank Accession No. ACC40567.1, SEQ ID NO: 2), Mycobacterium smegmatis (Genbank Accession No. ABK71854.1, SEQ ID NO: 3), Segniliparus rugosus (Genbank Accession No. EFV 11917.1, SEQ ID NO: 4), Mycobacterium massiliense (Genbank Accession No. EIV 11143.1, SEQ ID NO: 5), or Segniliparus rotundus (Genbank Accession No. ADG98140.1, SEQ ID NO: 6). See FIG. 6.

The carboxylate reductase encoded by the gene product of car and enhancer npt or sfp has broad substrate specificity, including terminal difunctional C4 and C5 carboxylic acids (Venkitasubramanian et al., Enzyme and Microbial Technology, 2008, 42, 130-137).

In some embodiments, hexamethylenediamine is synthesized from the central precursor, 6-hydroxyhexanoate (which can be produced as described in FIG. 7), by conversion of 6-hydroxyhexanoate to 6-hydroxyhexanal by a carboxylate reductase classified, for example, under EC 1.2.99.6 such as the gene product of car (see above) in combination with a phosphopantetheine transferase enhancer (e.g., encoded by a sfp gene from Bacillus subtilis or npt gene from Nocardia) or the gene product of GriC & GriD (Suzuki et al., 2007, supra); followed by conversion of 6-aminohexanal to 6-aminohexanol by a ω-transaminase classified, for example, under EC 2.6.1.18, EC 2.6.1.19, EC 2.6.1.29, EC 2.6.1.48, or EC 2.6.1.82 such as SEQ ID NOs:7-12, see above; followed by conversion to 7-aminoheptanal by an alcohol dehydrogenase classified, for example, under EC 1.1.1.- (e.g., EC 1.1.1.1, EC 1.1.1.2, EC 1.1.1.21, or EC 1.1.1.184) such as the gene product of YMR318C or YqhD (Liu et al., Microbiology, 2009, 155, 2078-2085; Larroy et al., 2002, Biochem J., 361(Pt 1), 163-172; Jarboe, 2011, Appl. Microbiol. Biotechnol., 89(2), 249-257) or the protein having GenBank Accession No. CAA81612.1; followed by conversion to heptamethylenediamine by a ω-transaminase classified, for example, under EC 2.6.1.18, EC 2.6.1.19, EC 2.6.1.29, EC 2.6.1.48, or EC 2.6.1.82 such as SEQ ID NOs:7-12, see above. See FIG. 6.

In some embodiments, hexamethylenediamine is synthesized from the central precursor, 6-aminohexanoate, by conversion of 6-aminohexanoate to N6-acetyl-6-aminohexanoate by an N-acetyltransferase such as a lysine N-acetyltransferase classified, for example, under EC 2.3.1.32; followed by conversion to N6-acetyl-6-aminohexanal by a carboxylate reductase classified, for example, under EC 1.2.99.6 such as the gene product of car (see above) in combination with a phosphopantetheine transferase enhancer (e.g., encoded by a sfp gene from Bacillus subtilis or npt gene from Nocardia) or the gene product of GriC & GriD; followed by conversion to N6-acetyl-1,6-diaminohexane by a ω-transaminase classified, for example, under EC 2.6.1.18, EC 2.6.1.19, EC 2.6.1.29, EC 2.6.1.48, or EC 2.6.1.82 such as SEQ ID NOs:7-12, see above; followed by conversion to heptamethylenediamine by an acetylputrescine deacylase classified, for example, under EC 3.5.1.62. See, FIG. 6.

In some embodiments, hexamethylenediamine is synthesized from the central precursor, adipate semialdehyde, by conversion of adipate semialdehyde to hexanedial by a carboxylate reductase classified, for example, under EC 1.2.99.6 such as the gene product of car (see above) in combination with a phosphopantetheine transferase enhancer (e.g., encoded by a sfp gene from Bacillus subtilis or npt gene from Nocardia) or the gene product of GriC & GriD; followed by conversion to 6-aminohexanal by a ω-transaminase classified, for example, under EC 2.6.1.18, EC 2.6.1.19, or EC 2.6.1.48; followed by conversion to hexamethylenediamine by a ω-transaminase classified, for example, under EC 2.6.1.18, EC 2.6.1.19, EC 2.6.1.29, EC 2.6.1.48, or EC 2.6.1.82 such as SEQ ID NOs:7-12. See FIG. 6.

Pathways Using Hexanoate as Central Precursor to 6-Hydroxyhexanoate or 1,6-Hexanediol In some embodiments, 6-hydroxyhexanoate is synthesized from the central precursor, hexanoate, by conversion of hexanoate to 6-hydroxyhexanoate by a monooxygenase such as from the CYP153 family (e.g., CYP153A). See FIG. 7.

In some embodiments, 1,6 hexanediol is synthesized from the central precursor, 6-hydroxyhexanoate, by conversion of 6-hydroxyhexanoate to 6-hydroxyhexanal by a carboxylate reductase classified, for example, under EC 1.2.99.6 such as the gene product of car (see above) in combination with a phosphopantetheine transferase enhancer (e.g., encoded by a sfp gene from Bacillus subtilis or npt gene from Nocardia) or the gene products of GriC and GriD from Streptomyces griseus (Suzuki et al., J. Antibiot., 2007, 60(6), 380-387); followed by conversion of 6-hydroxyhexanal to 1,6 hexanediol by an alcohol dehydrogenase (classified, for example, under EC 1.1.1.- such as EC 1.1.1.1, EC 1.1.1.2, EC 1.1.1.21, or EC 1.1.1.184) such as the gene product of YMR318C or YqhD (from E. coli, GenBank Accession No. AAA69178.1) (see, e.g., Liu et al., Microbiology, 2009, 155, 2078-2085; Larroy et al., 2002, Biochem J., 361(Pt 1), 163-172; or Jarboe, 2011, Appl. Microbiol. Biotechnol., 89(2), 249-257) or the protein having GenBank Accession No. CAA81612.1 (from Geobacillus stearothermophilus). See, FIG. 8.

Cultivation Strategy

In some embodiments, one or more C6 building blocks are biosynthesized in a recombinant host using anaerobic, aerobic or micro-aerobic cultivation conditions. A non-cyclical or a cyclical cultivation strategy can be used to achieve the desired cultivation conditions. For example, a non-cyclical strategy can be used to achieve anaerobic, aerobic or micro-aerobic cultivation conditions.

In some embodiments, a cyclical cultivation strategy can be used to alternate between anaerobic cultivation conditions and aerobic cultivation conditions.

In some embodiments, the cultivation strategy entails nutrient limitation such as nitrogen, phosphate or oxygen limitation.

In some embodiments, a cell retention strategy using, for example, ceramic hollow fiber membranes can be employed to achieve and maintain a high cell density during either fed-batch or continuous fermentation.

In some embodiments, the principal carbon source fed to the fermentation in the synthesis of one or more C6 building blocks can derive from biological or non-biological feedstocks.

In some embodiments, the biological feedstock can be or can derive from, monosaccharides, disaccharides, lignocellulose, hemicellulose, cellulose, lignin, levulinic acid and formic acid, triglycerides, glycerol, fatty acids, agricultural waste, condensed distillers' solubles, or municipal waste.

The efficient catabolism of crude glycerol stemming from the production of biodiesel has been demonstrated in several microorganisms such as Escherichia coli, Cupriavidus necator, Pseudomonas oleavorans, Pseudomonas putida and Yarrowia lipolytica (Lee et al., Appl. Biochem. Biotechnol., 2012, 166:1801-1813; Yang et al., Biotechnology for Biofuels, 2012, 5:13; Meijnen et al., Appl. Microbiol. Biotechnol., 2011, 90:885-893).

The efficient catabolism of lignocellulosic-derived levulinic acid has been demonstrated in several organisms such as Cupriavidus necator and Pseudomonas putida in the synthesis of 3-hydroxyvalerate via the precursor propanoyl-CoA (Jaremko and Yu, 2011, supra; Martin and Prather, J. Biotechnol., 2009, 139:61-67).

The efficient catabolism of lignin-derived aromatic compounds such as benzoate analogues has been demonstrated in several microorganisms such as *Pseudomonas putida*, *Cupriavidus necator* (Bugg et al., *Current Opinion in Biotechnology*, 2011, 22, 394-400; Pérez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7):2419-2428).

The efficient utilization of fermentable sugars such as monosaccharides and disaccharides derived from cellulosic, hemicellulosic, cane and beet molasses, cassava, corn and other agricultural sources has been demonstrated for several microorganism such as *Escherichia coli*, *Corynebacterium glutamicum* and *Lactobacillus delbrueckii* and *Lactococcus lactis* (see, e.g., Hermann et al, *J. Biotechnol.*, 2003, 104:155-172; Wee et al., *Food Technol. Biotechnol.*, 2006, 44(2):163-172; Ohashi et al., *J. Bioscience and Bioengineering*, 1999, 87(5):647-654).

The efficient utilization of furfural, derived from a variety of agricultural lignocellulosic sources, has been demonstrated for *Cupriavidus necator* (Li et al., *Biodegradation*, 2011, 22:1215-1225).

In some embodiments, the non-biological feedstock can be or can derive from natural gas, syngas, $CO_2/H_2$, methanol, ethanol, benzoate, non-volatile residue (NVR) or a caustic wash waste stream from cyclohexane oxidation processes, or terephthalic acid/isophthalic acid mixture waste streams.

The efficient catabolism of methanol has been demonstrated for the methylotrophic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium ljungdahlii* and *Clostridium autoethanogenum* (Kopke et al., *Applied and Environmental Microbiology*, 2011, 77(15): 5467-5475).

The efficient catabolism of the non-volatile residue waste stream from cyclohexane processes has been demonstrated for numerous microorganisms, such as *Delftia acidovorans* and *Cupriavidus necator* (Ramsay et al., *Applied and Environmental Microbiology*, 1986, 52(1):152-156).

In some embodiments, the host microorganism is a prokaryote. For example, the prokaryote can be a bacterium from the genus *Escherichia* such as *Escherichia coli*; from the genus *Clostridia* such as *Clostridium ljungdahlii*, *Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens*, *Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. Such prokaryotes also can be a source of genes to construct recombinant host cells described herein that are capable of producing one or more C7 building blocks.

In some embodiments, the host microorganism is a eukaryote. For example, the eukaryote can be a filamentous fungus, e.g., one from the genus *Aspergillus* such as *Aspergillus niger*. Alternatively, the eukaryote can be a yeast, e.g., one from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing one or more C6 building blocks.

Metabolic Engineering

The present document provides methods involving less than all the steps described for all the above pathways. Such methods can involve, for example, one, two, three, four, five, six, seven, eight, nine, ten, eleven, twelve or more of such steps. Where less than all the steps are included in such a method, the first, and in some embodiments the only, step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host. This document provides host cells of any of the genera and species listed and genetically engineered to express one or more (e.g., two, three, four, five, six, seven, eight, nine, 10, 11, 12 or more) recombinant forms of any of the enzymes recited in the document. Thus, for example, the host cells can contain exogenous nucleic acids encoding enzymes catalyzing one or more of the steps of any of the pathways described herein.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined herein are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined here can be gene dosed, i.e., overexpressed, into the resulting genetically modified organism via episomal or chromosomal integration approaches.

In some embodiments, genome-scale system biology techniques such as Flux Balance Analysis can be utilized to devise genome scale attenuation or knockout strategies for directing carbon flux to a C6 building block.

Attenuation strategies include, but are not limited to; the use of transposons, homologous recombination (double cross-over approach), mutagenesis, enzyme inhibitors and RNAi interference.

In some embodiments, fluxomic, metabolomic and transcriptomal data can be utilized to inform or support genome-scale system biology techniques, thereby devising genome scale attenuation or knockout strategies in directing carbon flux to a C6 building block.

In some embodiments, the host microorganism's tolerance to high concentrations of a C6 building block can be improved through continuous cultivation in a selective environment.

In some embodiments, the host microorganism's endogenous biochemical network can be attenuated or augmented to (1) ensure the intracellular availability of acetyl-CoA, (2) create an NADH or NADPH imbalance that may only be balanced via the formation of one or more C6 building blocks, (3) prevent degradation of central metabolites, central precursors leading to and including one or more C6 building blocks and/or (4) ensure efficient efflux from the cell.

In some embodiments requiring intracellular availability of acetyl-CoA for C6 building block synthesis, endogenous enzymes catalyzing the hydrolysis of acetyl-CoA such as short-chain length thioesterases can be attenuated in the host organism.

In some embodiments requiring the intracellular availability of acetyl-CoA for C6 building block synthesis, an endogenous phosphotransacetylase generating acetate such as pta can be attenuated (Shen et al., *Appl. Environ. Microbiol.*, 2011, 77(9):2905-2915).

In some embodiments requiring the intracellular availability of acetyl-CoA for C6 building block synthesis, an endogenous gene in an acetate synthesis pathway encoding an acetate kinase, such as ack, can be attenuated.

In some embodiments requiring the intracellular availability of acetyl-CoA and NADH for C6 building block synthesis, an endogenous gene encoding an enzyme that catalyzes the degradation of pyruvate to lactate such as lactate dehydrogenase encoded by ldhA can be attenuated (Shen et al., 2011, supra).

In some embodiments requiring the intracellular availability of acetyl-CoA and NADH for C6 building block synthesis, endogenous genes encoding enzymes, such as menaquinol-fumarate oxidoreductase, that catalyze the degradation of phophoenolpyruvate to succinate such as frdBC can be attenuated (see, e.g., Shen et al., 2011, supra).

In some embodiments requiring the intracellular availability of acetyl-CoA and NADH for C6 building block synthesis, an endogenous gene encoding an enzyme that catalyzes the degradation of acetyl-CoA to ethanol such as the alcohol dehydrogenase encoded by adhE can be attenuated (Shen et al., 2011, supra).

In some embodiments, where pathways require excess NADH co-factor for C6 building block synthesis, a recombinant formate dehydrogenase gene can be overexpressed in the host organism (Shen et al., 2011, supra).

In some embodiments, where pathways require excess NADH co-factor for C7 building block synthesis, a recombinant NADH-consuming transhydrogenase can be attenuated.

In some embodiments, an endogenous gene encoding an enzyme that catalyzes the degradation of pyruvate to ethanol such as pyruvate decarboxylase can be attenuated.

In some embodiments, an endogenous gene encoding an enzyme that catalyzes the generation of isobutanol such as a 2-oxoacid decarboxylase can be attenuated.

In some embodiments requiring the intracellular availability of acetyl-CoA for C6 building block synthesis, a recombinant acetyl-CoA synthetase such as the gene product of acs can be overexpressed in the microorganism (Satoh et al., *J. Bioscience and Bioengineering*, 2003, 95(4):335-341).

In some embodiments, carbon flux can be directed into the pentose phosphate cycle to increase the supply of NADPH by attenuating an endogenous glucose-6-phosphate isomerase (EC 5.3.1.9).

In some embodiments, carbon flux can be redirected into the pentose phosphate cycle to increase the supply of NADPH by overexpression a 6-phosphogluconate dehydrogenase and/or a transketolase (Lee et al., 2003, *Biotechnology Progress*, 19(5), 1444-1449).

In some embodiments, where pathways require excess NADPH co-factor in the synthesis of a C6 building block, a gene such as UdhA encoding a puridine nucleotide transhydrogenase can be overexpressed in the host organisms (Brigham et al., *Advanced Biofuels and Bioproducts*, 2012, Chapter 39, 1065-1090).

In some embodiments, where pathways require excess NADPH co-factor in the synthesis of a C6 Building Block, a recombinant glyceraldehyde-3-phosphate-dehydrogenase gene such as GapN can be overexpressed in the host organisms (Brigham et al., 2012, supra).

In some embodiments, where pathways require excess NADPH co-factor in the synthesis of a C6 building block, a recombinant malic enzyme gene such as macA or maeB can be overexpressed in the host organisms (Brigham et al., 2012, supra).

In some embodiments, where pathways require excess NADPH co-factor in the synthesis of a C6 building block, a recombinant glucose-6-phosphate dehydrogenase gene such as zwf can be overexpressed in the host organisms (Lim et al., *J. Bioscience and Bioengineering*, 2002, 93(6), 543-549).

In some embodiments, where pathways require excess NADPH co-factor in the synthesis of a C6 building block, a recombinant fructose 1,6 diphosphatase gene such as fbp can be overexpressed in the host organisms (Becker et al., *J. Biotechnol.*, 2007, 132:99-109).

In some embodiments, where pathways require excess NADPH co-factor in the synthesis of a C6 building block, endogenous triose phosphate isomerase (EC 5.3.1.1) can be attenuated.

In some embodiments, where pathways require excess NADPH co-factor in the synthesis of a C6 building block, a recombinant glucose dehydrogenase such as the gene product of gdh can be overexpressed in the host organism (Satoh et al., *J. Bioscience and Bioengineering*, 2003, 95(4):335-341).

In some embodiments, endogenous enzymes facilitating the conversion of NADPH to NADH can be attenuated, such as the NADH generation cycle that may be generated via inter-conversion of glutamate dehydrogenases classified under EC 1.4.1.2 (NADH-specific) and EC 1.4.1.4 (NADPH-specific).

In some embodiments, an endogenous glutamate dehydrogenase (EC 1.4.1.3) that utilizes both NADH and NADPH as co-factors can be attenuated.

In some embodiments, a membrane-bound cytochrome P450 such as CYP4F3B can be solubilized by only expressing the cytosolic domain and not the N-terminal region that anchors the P450 to the endoplasmic reticulum (Scheller et al., *J. Biol. Chem.*, 1994, 269(17):12779-12783).

In some embodiments, an enoyl-CoA reductase can be solubilized via expression as a fusion protein with a small soluble protein, for example, the maltose binding protein (Gloerich et al., *FEBS Letters*, 2006, 580, 2092-2096).

In some embodiments using hosts that naturally accumulate polyhydroxyalkanoates, the endogenous polymer synthase enzymes can be attenuated in the host strain.

In some embodiments, a L-alanine dehydrogenase can be overexpressed in the host to regenerate L-alanine from pyruvate as an amino donor for ω-transaminase reactions.

In some embodiments, a L-glutamate dehydrogenase, a L-glutamine synthetase, or a glutamate synthase can be overexpressed in the host to regenerate L-glutamate from 2-oxoglutarate as an amino donor for ω-transaminase reactions.

In some embodiments, enzymes such as a pimeloyl-CoA dehydrogenase classified under, EC 1.3.1.62; an acyl-CoA dehydrogenase classified, for example, under EC 1.3.8.7, EC 1.3.8.1, or EC 1.3.99.-; and/or a butyryl-CoA dehydrogenase classified, for example, under EC 1.3.8.6 that degrade central metabolites and central precursors leading to and including C6 building blocks can be attenuated.

In some embodiments, endogenous enzymes activating C6 building blocks via Coenzyme A esterification such as CoA-ligases (e.g., an adipyl-CoA synthetase) classified under, for example, EC 6.2.1.- can be attenuated.

In some embodiments, the efflux of a C6 building block across the cell membrane to the extracellular media can be enhanced or amplified by genetically engineering structural modifications to the cell membrane or increasing any associated transporter activity for a C6 building block.

The efflux of hexamethylenediamine can be enhanced or amplified by overexpressing broad substrate range multidrug transporters such as Blt from *Bacillus subtilis* (Woolridge et al., 1997, *J. Biol. Chem.*, 272(14):8864-8866); AcrB and AcrD from *Escherichia coli* (Elkins & Nikaido, 2002, *J. Bacteriol.*, 184(23), 6490-6499), NorA from *Staphylococcus aereus* (Ng et al., 1994, *Antimicrob Agents Chemother,* 38(6), 1345-1355), or Bmr from *Bacillus subtilis* (Neyfakh, 1992, *Antimicrob Agents Chemother,* 36(2), 484-485).

The efflux of 6-aminohexanoate and heptamethylenediamine can be enhanced or amplified by overexpressing the solute transporters such as the lysE transporter from *Corynebacterium glutamicum* (Bellmann et al., 2001, *Microbiology*, 147, 1765-1774).

The efflux of adipic acid can be enhanced or amplified by overexpressing a dicarboxylate transporter such as the SucE transporter from *Corynebacterium glutamicum* (Huhn et al., *Appl. Microbiol. & Biotech.*, 89(2), 327-335).

Producing C6 Building Blocks Using a Recombinant Host

Typically, one or more C6 building blocks can be produced by providing a host microorganism and culturing the provided microorganism with a culture medium containing a suitable carbon source as described above. In general, the culture media and/or culture conditions can be such that the microorganisms grow to an adequate density and produce a C6 building block efficiently. For large-scale production processes, any method can be used such as those described elsewhere (Manual of Industrial Microbiology and Biotechnology, 2$^{nd}$ Edition, Editors: A. L. Demain and J. E. Davies, ASM Press; and Principles of Fermentation Technology, P. F. Stanbury and A. Whitaker, Pergamon). Briefly, a large tank (e.g., a 100 gallon, 200 gallon, 500 gallon, or more tank) containing an appropriate culture medium is inoculated with a particular microorganism. After inoculation, the microorganism is incubated to allow biomass to be produced. Once a desired biomass is reached, the broth containing the microorganisms can be transferred to a second tank. This second tank can be any size. For example, the second tank can be larger, smaller, or the same size as the first tank. Typically, the second tank is larger than the first such that additional culture medium can be added to the broth from the first tank. In addition, the culture medium within this second tank can be the same as, or different from, that used in the first tank.

Once transferred, the microorganisms can be incubated to allow for the production of a C6 building block. Once produced, any method can be used to isolate C6 building blocks. For example, C6 building blocks can be recovered selectively from the fermentation broth via adsorption processes. In the case of adipic acid and 6-aminoheptanoic acid, the resulting eluate can be further concentrated via evaporation, crystallized via evaporative and/or cooling crystallization, and the crystals recovered via centrifugation. In the case of hexamethylenediamine and 1,6-heptanediol, distillation may be employed to achieve the desired product purity.

The invention will be further described in the following examples, which do not limit the scope of the invention described in the claims.

EXAMPLES

Example 1

Genome-Scale Attenuation Strategy for Cyclical Synthesis of Adipic Acid from Glucose in *Saccharomyces cerevisiae*

Genome-scale Flux Balance Analysis was undertaken using the genome-scale model for *Saccharomyces cerevisiae* designated iMM904 (Mo et al., *BMC Systems Biology,* 2009, 3(37), 1-17).

The IMM904 model was extended by including ω-oxidation pathways as outlined in published work for eukaryotic organisms (Sanders et al., Journal of Lipid Research, 2005, 46(5), 1001-1008). Furthermore, the β-oxidation reactions in the peroxisome of the iMM904 model were extended and relevant membrane transport reactions were included. The inactivation of a fumarate reductase was required during validation of the extended model to align model fluxes with experimental flux data.

The NADH-specific enzymatic reactions outlined in FIG. 1 were incorporated into the model.

Allowance was made for the membrane transport of hexanoic acid and adipic acid to and from the extracellular media.

The stoichiometric balance of NADH in the production of 1-butanol in *E. coli* is far more efficient when overexpressing formate dehydrogenase (Shen et al., *Appl. Environ. Microbiol.,* 2011, 77(9), 2905-2915). The iMM904 model includes formate dehydrogenase, but lacked pyruvate formate lyase activity, which was included into the *Saccharomyces cerevisiae* model.

The co-factor specificity of NAD(H) or NADP(H) dependent enzymes was assessed and where published literature was not unequivocal in terms of specificity, a promiscuous enzyme was assumed.

The metabolic engineering workbench, Optflux, was used to search the solution space associated with the biochemical network for attenuation strategies that (1) produce hexanoate anaerobically from glucose, followed by (2) production of adipate aerobically from the extracellular hexanoate, whilst co-feeding glucose as carbon and energy source.

The optimization trials found four beneficial attenuations; viz. (1) attenuating glucose-6-phosphate isomerase, directing flux into the pentose phosphate cycle; (2) attenuating pyruvate decarboxylase or alcohol dehydrogenase, preventing ethanol production; (3) attenuating 2-oxoacid decarboxylase, preventing isobutanol production and (4) inactivating β-oxidation, preventing central precursor, central metabolite and adipic acid degradation.

The attenuations in this *S. cerevisiae* mutant using glucose as carbon and energy source, favored the balancing of NADH via the production of hexanoic acid as a means of maximizing biomass growth.

Overexpression of formate dehydrogenase in the *S. cerevisiae* mutant eliminated the by-product formation of formate and pyruvate, producing hexanoate with a molar yield of 0.62 [(mol hexanoate)/(mol glucose)].

Cycling from anaerobic to aerobic cultivation, while maintaining a glucose feed rate to match the growth rate under anaerobic conditions, resulted in an overall molar yield of 0.38 [(mol adipate)/(mol total glucose)].

In-silico attenuation of the biochemical network using a validated model determined that a cultivation strategy, cycling between anaerobic and aerobic conditions, produces predominantly adipic acid from the fed glucose.

Example 2

Genome-Scale Attenuation Strategy for Micro-Aerobic Synthesis from Glucose Using NADH Imbalance to Direct Carbon Flux Towards Adipic Acid in *Saccharomyces cerevisiae*

The iMM904 model outlined in Example 1 was utilized to assess the non-cyclical production of adipic acid using glucose as carbon and energy source under micro-aerobic, substrate oxidation and growth limiting cultivation conditions.

Using the extended iMM904 model and the metabolic engineering workbench, Optflux; optimization trials found an optimal attenuation strategy including: (1) attenuating hexanoate transport to the extracellular media; (2) attenuating ethanol excretion to the extracellular media; (3) attenuating 2-hydroxybutyrate oxidoreductase, preventing 2-hydroxybutyrate production; (4) attenuating DL glycerol-3-phosphatase, preventing glycerol production and (5) attenuating malate dehydrogenase, preventing inter-conversion of NADH to NADPH.

The resulting *S. cerevisiae* mutant produces adipate as the most advantageous means of balancing NADH to maximize biomass growth, producing adipate with a molar yield of 0.71 [(mol adipate)/(mol glucose)].

In-silico attenuation of the biochemical network using a validated model determined that a non-cyclical cultivation strategy under micro-aerobic conditions produces predominantly adipic acid from the fed glucose.

Example 3

Genome-Scale Attenuation Strategy for Aerobic Synthesis from Glucose Using NADPH Imbalance to Direct Carbon Flux Towards Adipic Acid in *Saccharomyces cerevisiae*

The iMM904 model outlined in Example 1 was utilized to assess the non-cyclical production of adipic acid using glucose as carbon and energy source under aerobic cultivation and growth limiting conditions.

The NADH-specific enzymatic reactions outlined in FIG. 1 were replaced by the equivalent NADPH-specific enzymatic reactions outlined in FIG. 2.

Using the extended iMM904 model and the metabolic engineering workbench, Optflux; optimization trials found an optimal attenuation strategy including; (1) attenuating triose phosphate isomerase/phosphoglucose isomerase, redirecting flux into the pentose phosphate cycle; (2) preventing the inter-conversion of NADPH to NADH, by attenuating the NADH-dependent glutamate dehydrogenase and proline oxidase.

The resulting *S. cerevisiae* mutant produces adipate as the most advantageous means of balancing NADPH to maximize biomass growth, producing adipate with a molar yield of 0.4 [(mol adipate)/(mol glucose)].

In-silico attenuation of the biochemical network using a validated model determined that a non-cyclical cultivation strategy under aerobic conditions produces predominantly adipic acid from the fed glucose.

Example 4

Enzyme Activity of Thioesterases Using Hexanoyl-CoA as a Substrate and Forming Hexanoate A nucleotide sequence encoding a His tag was added to the tesB gene from *Escherichia coli* that encodes a thioesterase (SEQ ID NO 1, see FIG. 9), such that an N-terminal HIS tagged thioesterase could be produced. The modified tesB gene was cloned into a pET15b expression vector under control of the T7 promoter. The expression vector was transformed into a BL21[DE3] *E. coli* host. The resulting recombinant *E. coli* strain was cultivated at 37° C. in a 500 mL shake flask culture containing 50 mL Luria Broth (LB) media and antibiotic selection pressure, with shaking at 230 rpm. The culture was induced overnight at 17° C. using 0.5 mM IPTG.

The pellet from the induced shake flask culture was harvested via centrifugation. The pellet was resuspended and lysed in Y-per™ solution (ThermoScientific, Rockford, Ill.). The cell debris was separated from the supernatant via centrifugation. The thioesterase was purified from the supernatant using Ni-affinity chromatography and the eluate was buffer exchanged and concentrated via ultrafiltration.

Figure 10:
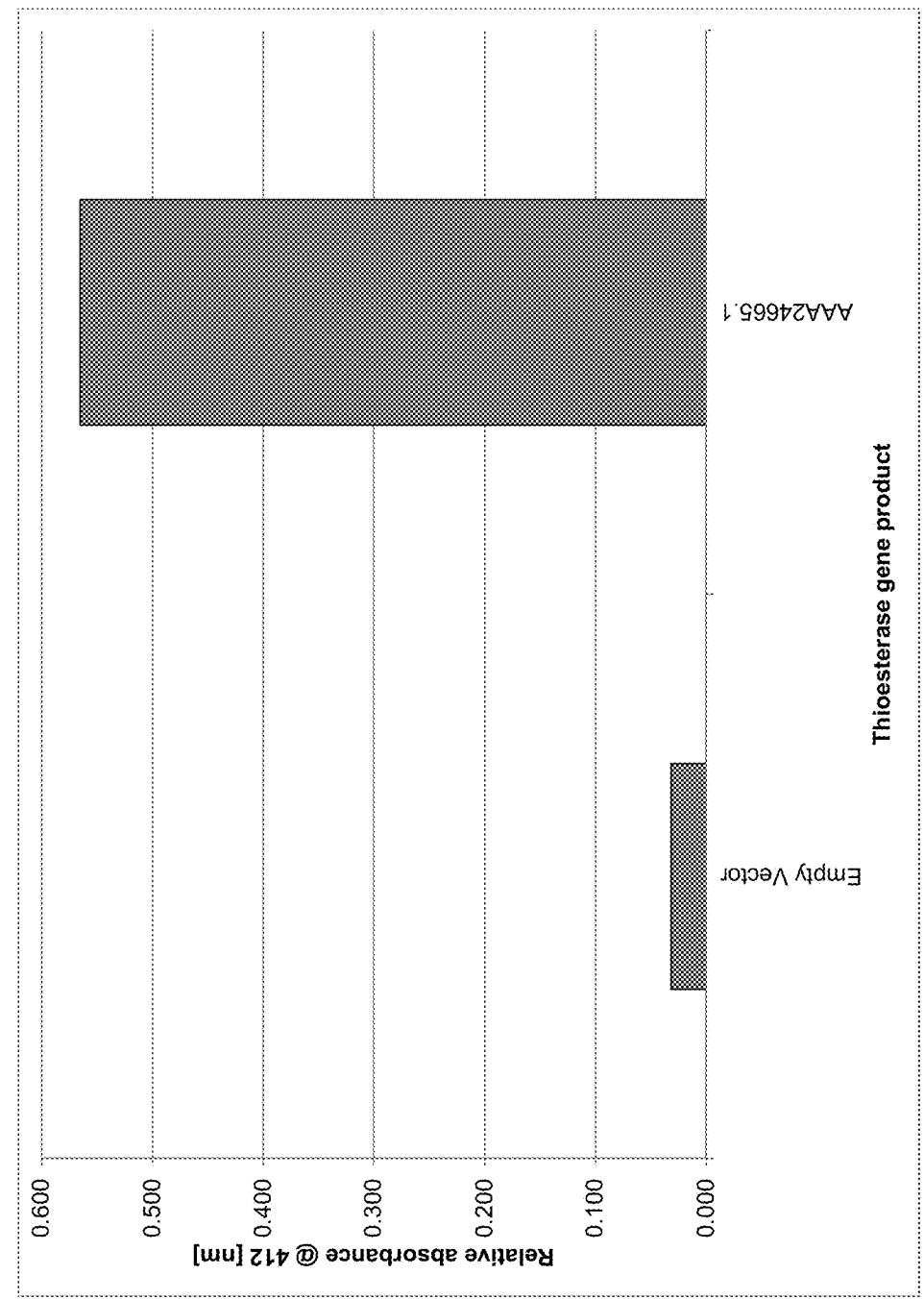
FIG. 10 is a bar graph of the relative absorbance at 412 nm of released CoA as a measure of the activity of a thioesterase for converting hexanoyl-CoA to hexanoate relative to the empty vector control.

The enzyme activity assay was performed in triplicate in a buffer composed of 50 mM phosphate buffer (pH=7.4), 0.1 mM Ellman's reagent, and 133 µM of hexanoyl-CoA (as substrate). The enzyme activity assay reaction was initiated by adding 0.8 µM of the tesB gene product to the assay buffer containing the hexanoyl-CoA and incubating at 37° C. for 20 min. The release of Coenzyme A was monitored by absorbance at 412 nm. The absorbance associated with the substrate only control, which contained boiled enzyme, was subtracted from the active enzyme assay absorbance and compared to the empty vector control. The gene product of tesB accepted hexanoyl-CoA as substrate as confirmed via relative spectrophotometry (see FIG. 10) and synthesized hexanoate as a reaction product.

Example 5

Enzyme Activity of ω-Transaminase Using Adipate Semialdehyde as Substrate and Forming 6-Aminohexanoate A nucleotide sequence encoding a His-tag was added to the genes from *Chromobacterium violaceum, Pseudomonas aeruginosa, Pseudomonas syringae, Rhodobacter sphaeroides*, and *Vibrio fluvialis* encoding the ω-transaminases of SEQ ID NOs: 7, 8, 9, 10 and 12, respectively (see FIG. 9) such that N-terminal HIS tagged CD-transaminases could be produced. Each of the resulting modified genes was cloned into a pET21a expression vector under control of the T7 promoter and each expression vector was transformed into a BL21 [DE3] *E. coli* host. The resulting recombinant *E. coli* strains were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 6-aminohexanoate to adipate semialdehyde) were performed in a buffer composed of a final concentration of 50 mM HEPES buffer (pH=7.5), 10 mM 6-aminohexanoate, 10 mM pyruvate and 100 μM pyridoxyl 5' phosphate. Each enzyme activity assay reaction was initiated by adding cell free extract of the ω-transaminase gene product or the empty vector control to the assay buffer containing the 6-aminohexanoate and incubated at 25° C. for 24 h, with shaking at 250 rpm. The formation of L-alanine from pyruvate was quantified via RP-HPLC.

Figure 16:
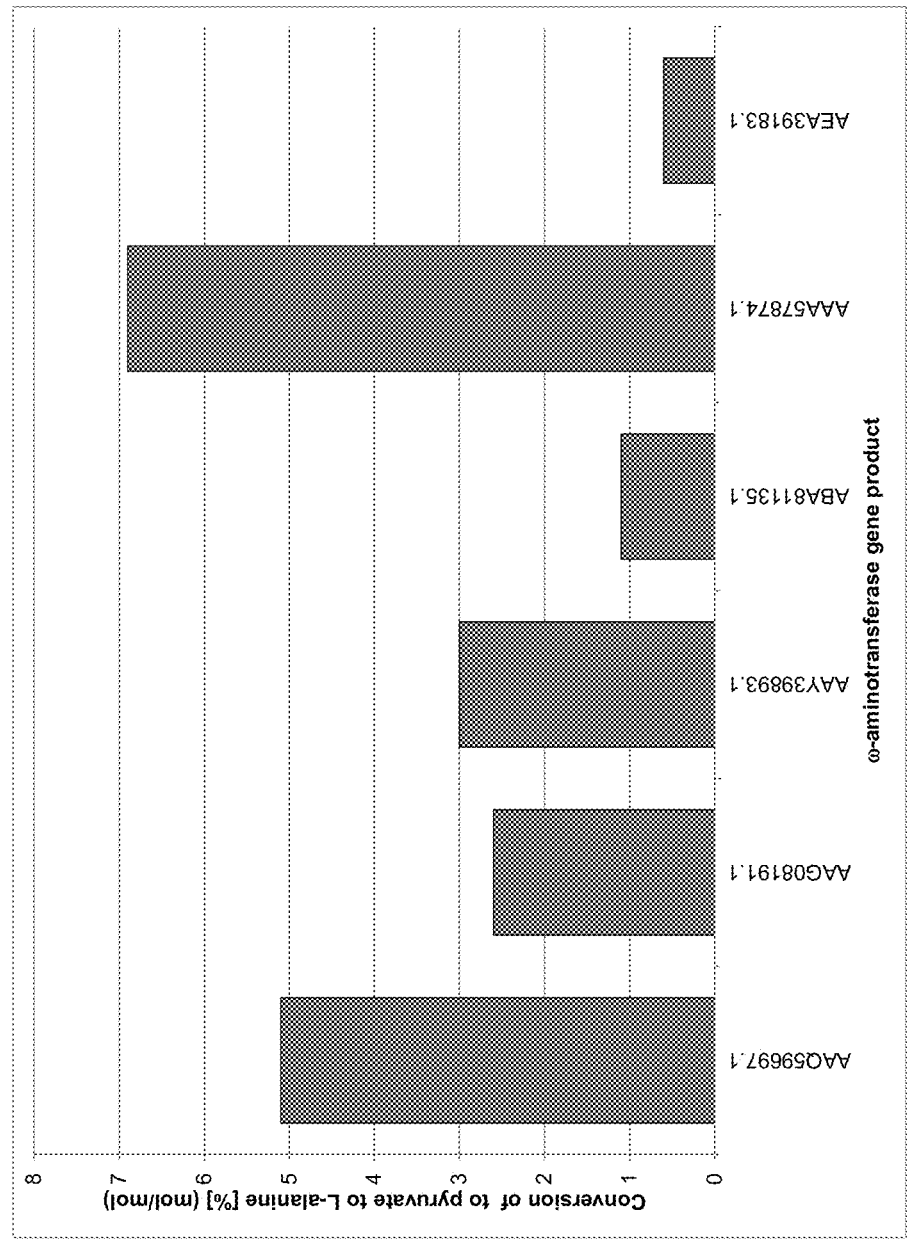
FIG. 16 is a bar graph summarizing the percent conversion after 4 hours of pyruvate to L-alanine (mol/mol) as a measure of the ω-transaminase activity of the enzyme only controls (no substrate).
Figure 17:
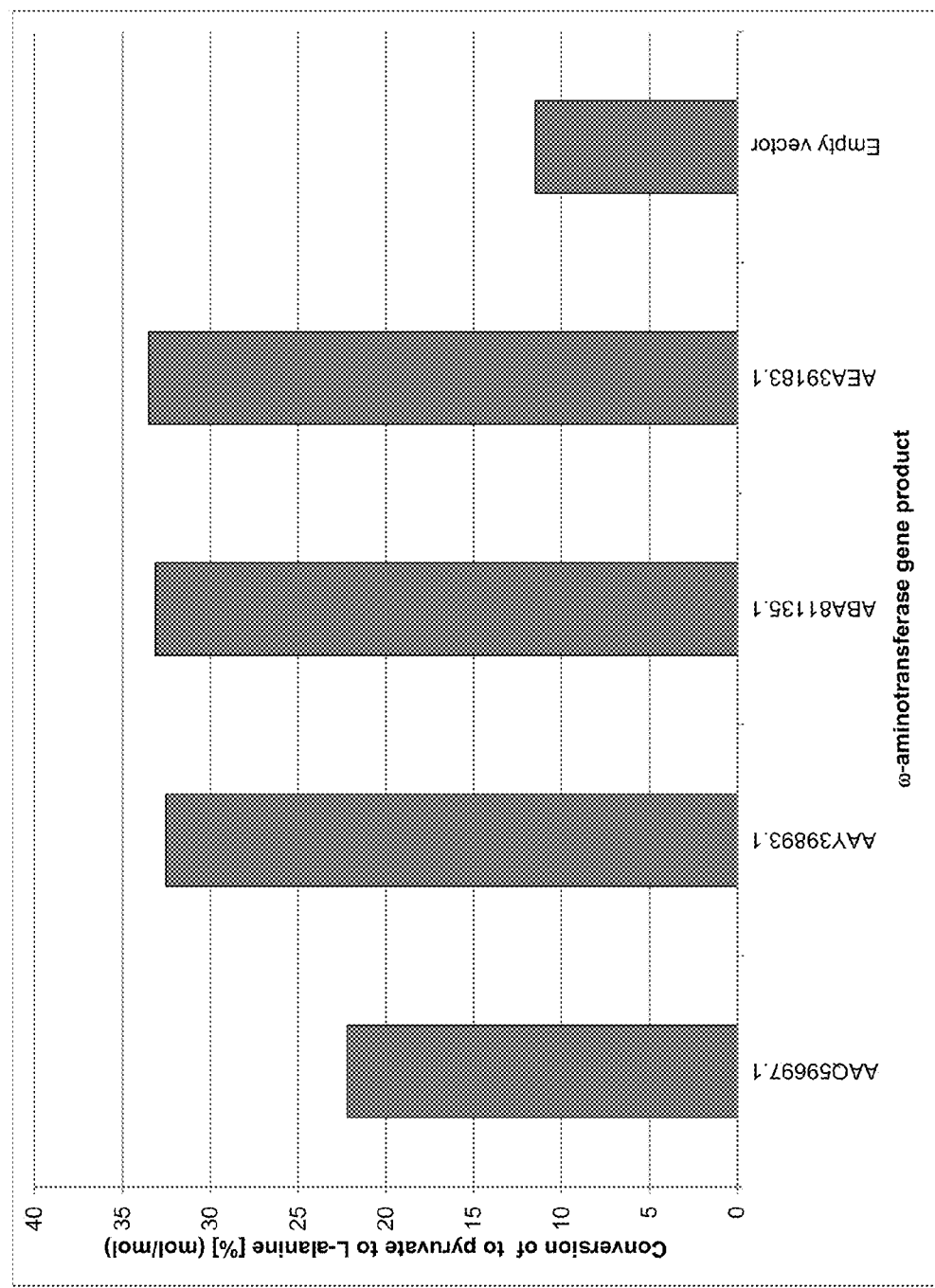
FIG. 17 is a bar graph of the percent conversion after 24 hours of pyruvate to L-alanine (mol/mol) as a measure of the ω-transaminase activity for converting 6-aminohexanoate to adipate semialdehyde relative to the empty vector control.

Each enzyme only control without 6-aminoheptanoate demonstrated low base line conversion of pyruvate to L-alanine See FIG. 16. The gene product of SEQ ID NO 7, SEQ ID NO 9, SEQ ID NO 10 and SEQ ID NO 12 accepted 6-aminohexanote as substrate as confirmed against the empty vector control. See FIG. 17.

Enzyme activity in the forward direction (i.e., adipate semialdehyde to 6-aminohexanoate) was confirmed for the transaminases of SEQ ID NO 7, SEQ ID NO 8, SEQ ID NO 9, SEQ ID NO 10 and SEQ ID NO 12. Enzyme activity assays were performed in a buffer composed of a final concentration of 50 mM HEPES buffer (pH=7.5), 10 mM adipate semialdehyde, 10 mM L-alanine and 100 μM pyridoxyl 5' phosphate. Each enzyme activity assay reaction was initiated by adding a cell free extract of the ω-transaminase gene product or the empty vector control to the assay buffer containing the adipate semialdehyde and incubated at 25° C. for 4 h, with shaking at 250 rpm. The formation of pyruvate was quantified via RP-HPLC.

Figure 18:
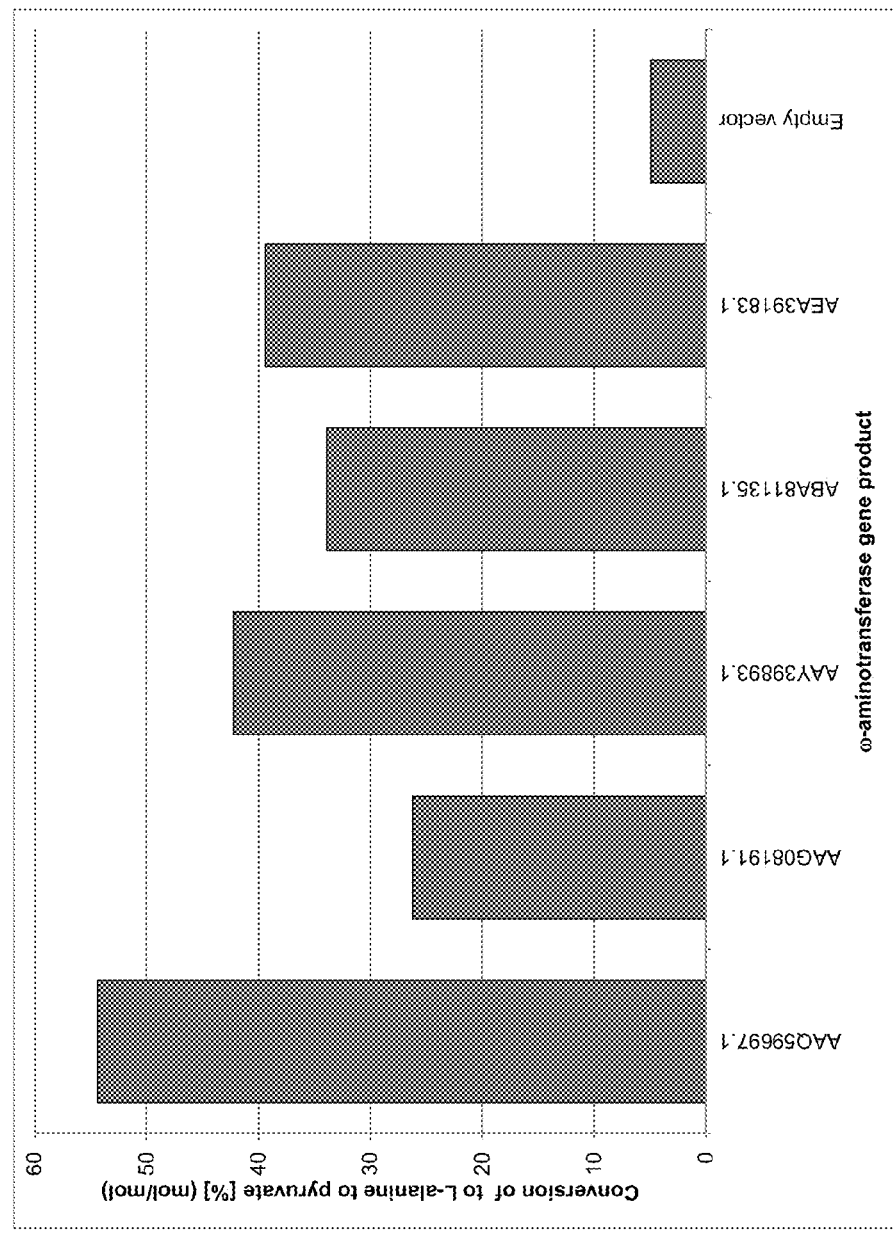
FIG. 18 is a bar graph of the percent conversion after 4 hours of L-alanine to pyruvate (mol/mol) as a measure of the ω-transaminase activity for converting adipate semialdehyde to 6-aminohexanoate relative to the empty vector control.

The gene product of SEQ ID NO 7, SEQ ID NO 8, SEQ ID NO 9, SEQ ID NO 10 and SEQ ID NO 12 accepted adipate semialdehyde as substrate as confirmed against the empty vector control. See FIG. 18. The reversibility of the ω-transaminase activity was confirmed, demonstrating that the ω-transaminases of SEQ ID NO 7, SEQ ID NO 8, SEQ ID NO 9, SEQ ID NO 10 and SEQ ID NO 12 accepted adipate semialdehyde as substrate and synthesized 6-aminohexanoate as a reaction product.

Example 6

Enzyme Activity of Carboxylate Reductase Using Adipate as Substrate and Forming Adipate Semialdehyde A nucleotide sequence encoding a HIS-tag was added to the genes from *Segniliparus rugosus* and *Segniliparus rotundus* that encode the carboxylate reductases of SEQ ID NOs: 4 and 6, respectively (see FIG. 9), such that N-terminal HIS tagged carboxylate reductases could be produced. Each of the modified genes was cloned into a pET Duet expression vector along with a sfp gene encoding a HIS-tagged phosphopantetheine transferase from *Bacillus subtilis*, both under the T7 promoter. Each expression vector was transformed into a BL21[DE3] *E. coli* host and the resulting recombinant *E. coli* strains were cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication, and the cell debris was separated from the supernatant via centrifugation. The carboxylate reductases and phosphopantetheine transferases were purified from the supernatant using Ni-affinity chromatography, diluted 10-fold into 50 mM HEPES buffer (pH=7.5), and concentrated via ultrafiltration.

Figure 11:
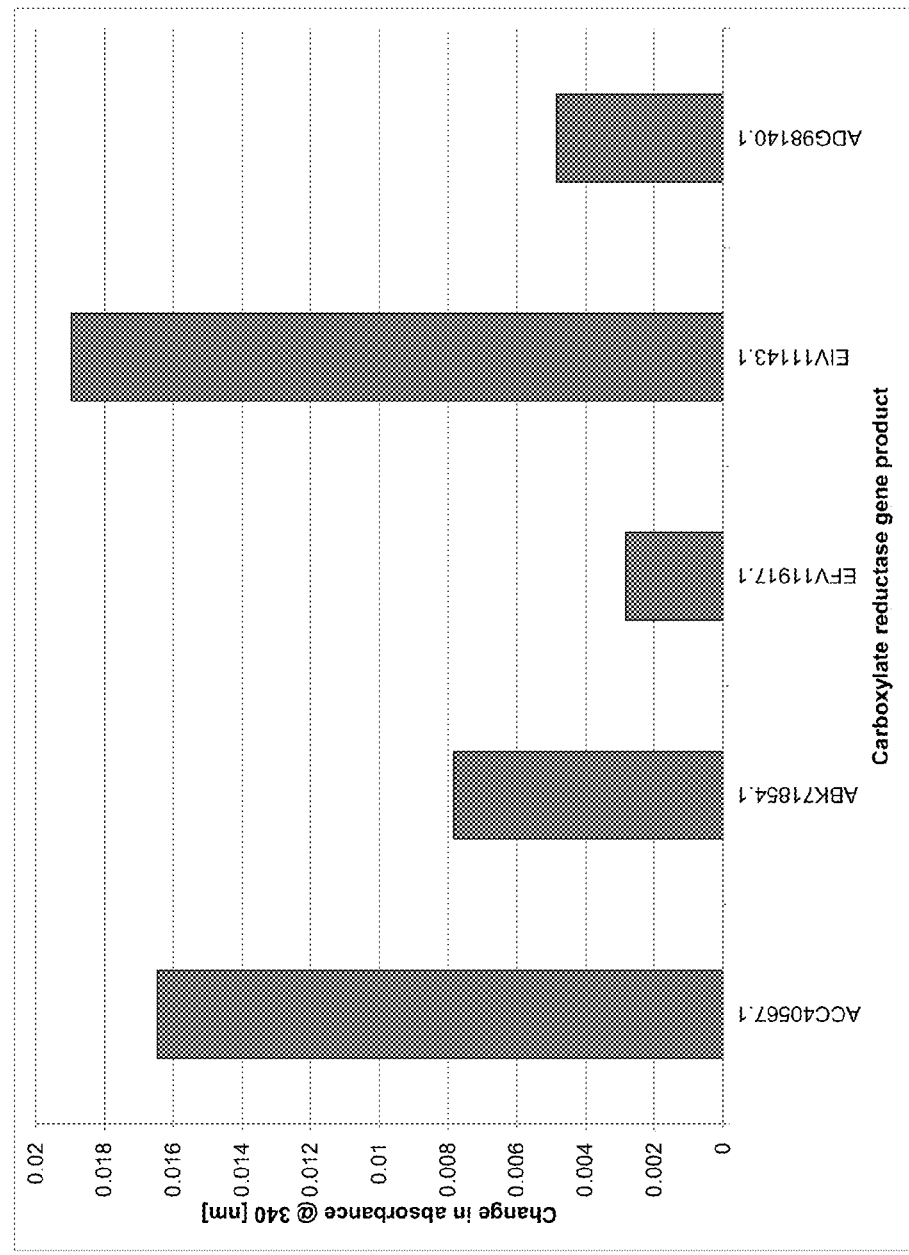
FIG. 11 is a bar graph summarizing the change in absorbance at 340 nm after 20 minutes, which is a measure of the consumption of NADPH and the activity of the carboxylate reductases of the enzyme only controls (no substrate).

Enzyme activity assays (i.e., from adipate to adipate semialdehyde) were performed in triplicate in a buffer composed of a final concentration of 50 mM HEPES buffer (pH=7.5), 2 mM adipate, 10 mM MgCl$_2$, 1 mM ATP and 1 mM NADPH. Each enzyme activity assay reaction was initiated by adding purified carboxylate reductase and phosphopantetheine transferase gene products or the empty vector control to the assay buffer containing the adipate and then incubated at room temperature for 20 min. The consumption of NADPH was monitored by absorbance at 340 nm. Each enzyme only control without adipate demonstrated low base line consumption of NADPH. See FIG. 11.

Figure 12:
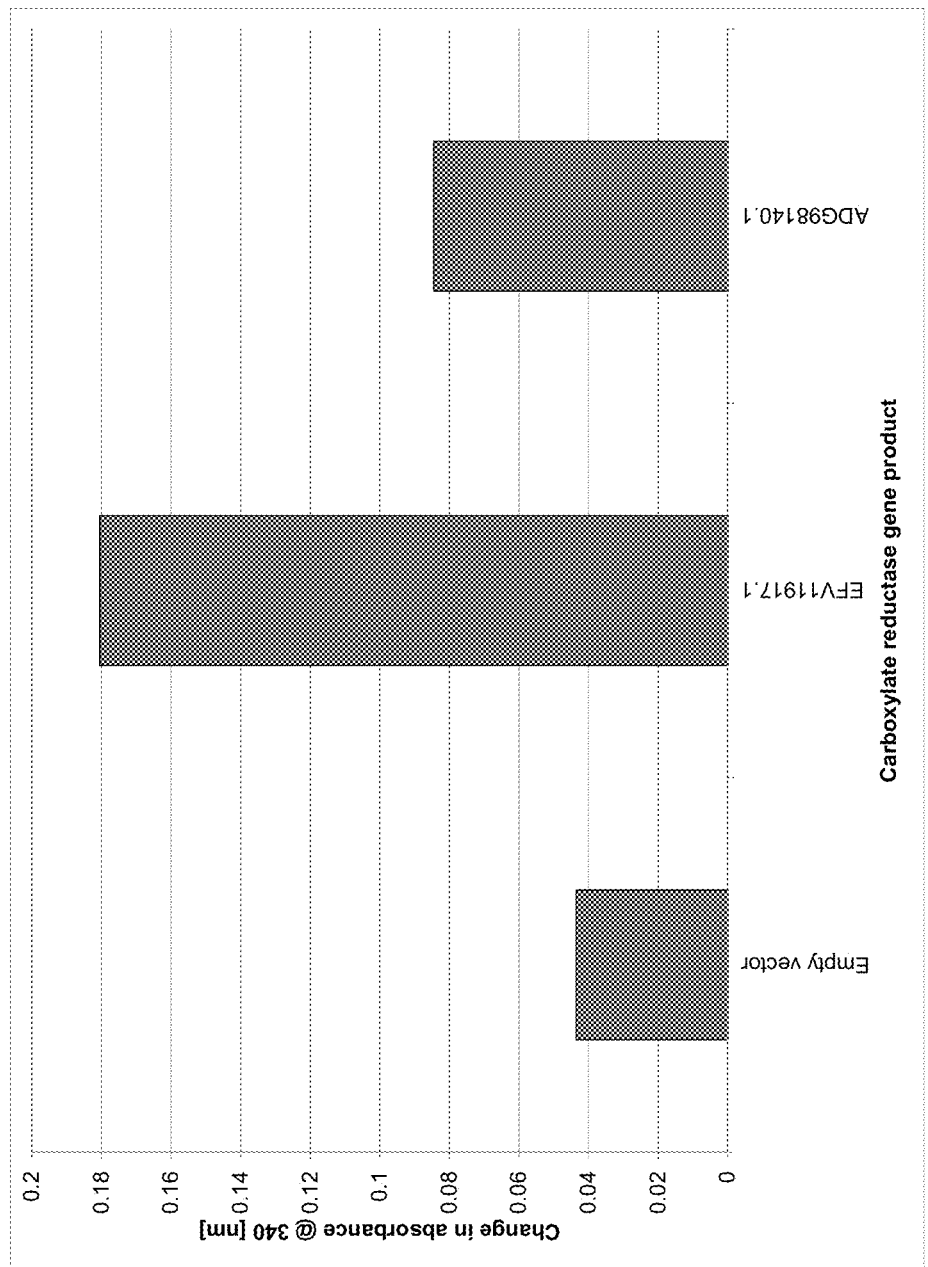
FIG. 12 is a bar graph of the change in absorbance at 340 nm after 20 minutes, which is a measure of the consumption of NADPH and the activity of carboxylate reductases for converting adipate to adipate semialdehyde relative to the empty vector control.

The gene products of SEQ ID NO 4 and SEQ ID NO 6, enhanced by the gene product of sfp, accepted adipate as substrate, as confirmed against the empty vector control (see FIG. 12), and synthesized adipate semialdehyde.

Example 7

Enzyme Activity of Carboxylate Reductase Using 6-Hydroxyhexanoate as Substrate and Forming 6-Hydroxyhexanal A nucleotide sequence encoding a His-tag was added to the genes from *Mycobacterium marinum*, *Mycobacterium smegmatis*, *Mycobacterium smegmatis*, *Segniliparus rugosus*, *Mycobacterium massiliense*, and *Segniliparus rotundus* that encode the carboxylate reductases of SEQ ID NOs: 2-6, respectively (see FIG. 9) such that N-terminal HIS tagged carboxylate reductases could be produced. Each of the modified genes was cloned into a pET Duet expression vector alongside a sfp gene encoding a His-tagged phosphopantetheine transferase from *Bacillus subtilis*, both under control of the T7 promoter. Each expression vector was transformed into a BL21[DE3] *E. coli* host along with the expression vectors from Example 3. Each resulting recombinant *E. coli* strain was cultivated at 37° C. in a 250 mL shake flask culture containing 50 mL LB media and antibiotic selection pressure, with shaking at 230 rpm. Each culture was induced overnight at 37° C. using an auto-induction media.

The pellet from each induced shake flask culture was harvested via centrifugation. Each pellet was resuspended and lysed via sonication. The cell debris was separated from the supernatant via centrifugation. The carboxylate reductases and phosphopantetheine transferase were purified from the supernatant using Ni-affinity chromatography, diluted 10-fold into 50 mM HEPES buffer (pH=7.5) and concentrated via ultrafiltration.

Enzyme activity (i.e., 6-hydroxyhexanoate to 6-hydroxyhexanal) assays were performed in triplicate in a buffer composed of a final concentration of 50 mM HEPES buffer (pH=7.5), 2 mM 6-hydroxyhexanal, 10 mM MgCl$_2$, 1 mM ATP, and 1 mM NADPH. Each enzyme activity assay reaction was initiated by adding purified carboxylate reductase and phosphopantetheine transferase or the empty vector control to the assay buffer containing the 6-hydroxyhexanoate and then incubated at room temperature for 20 min. The consumption of NADPH was monitored by absorbance at 340 nm. Each enzyme only control without 6-hydroxyhexanoate demonstrated low base line consumption of NADPH. See FIG. 11.

Figure 13:
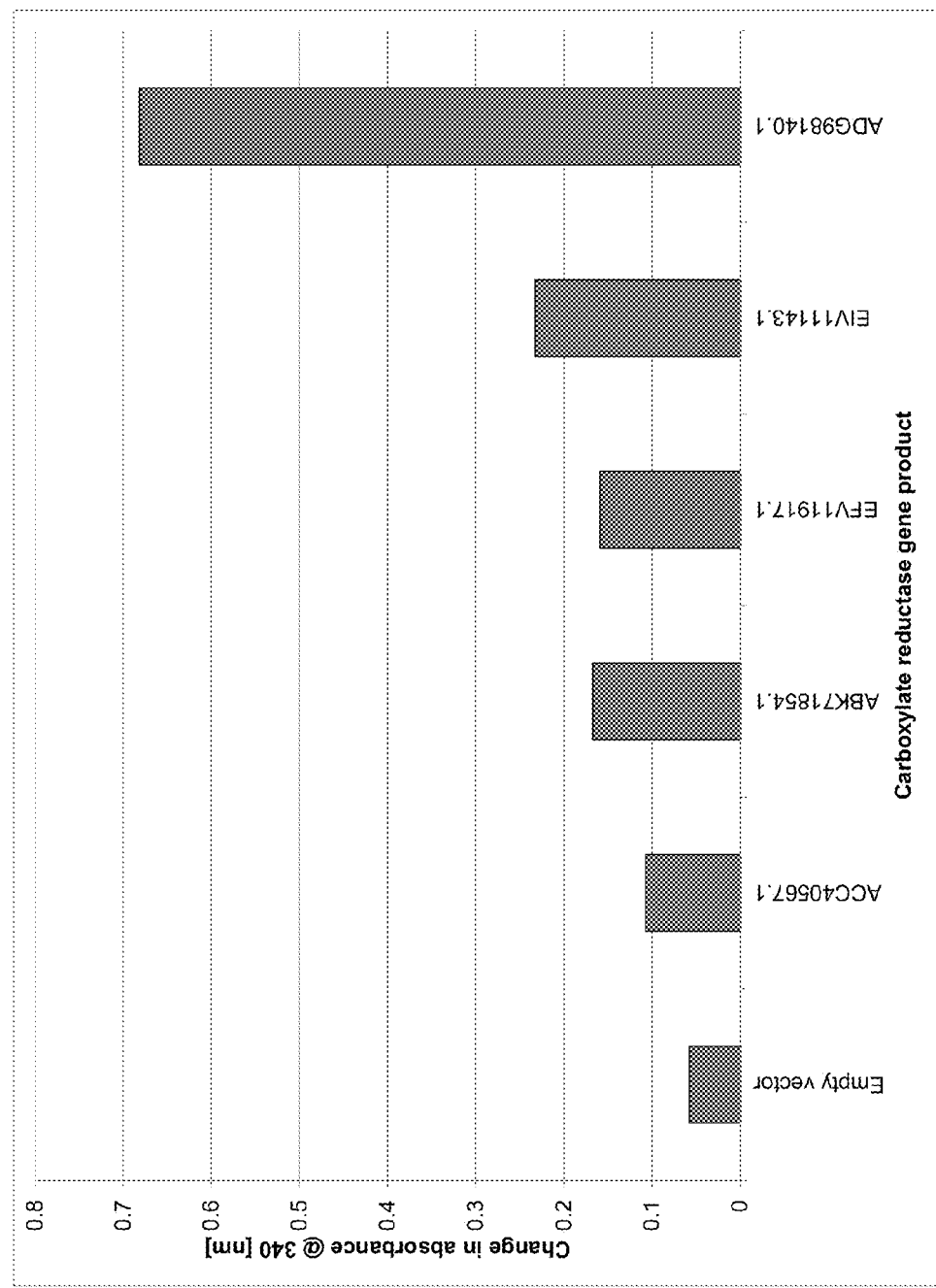
FIG. 13 is a bar graph of the change in absorbance at 340 nm after 20 minutes, which is a measure of the consumption of NADPH and the activity of carboxylate reductases for converting 6-hydroxyhexanoate to 6-hydroxyhexanal relative to the empty vector control.

The gene products of SEQ ID NO 2-6, enhanced by the gene product of sfp, accepted 6-hydroxyhexanoate as substrate as confirmed against the empty vector control (see FIG. 13), and synthesized 6-hydroxyhexanal.

Example 8

Enzyme Activity of ω-Transaminase for 6-Aminohexanol, Forming 6-Oxohexanol

A nucleotide sequence encoding an N-terminal His-tag was added to the *Chromobacterium violaceum, Pseudomonas aeruginosa, Pseudomonas syringae, Rhodobacter sphaeroides, Escherichia coli*, and *Vibrio fluvialis* genes encoding the w-transaminases of SEQ ID NOs: 7-12, respectively (see FIG. 9) such that N-terminal HIS tagged ω-transaminases could be produced. The modified genes were cloned into a pET21a expression vector under the T7 promoter. Each expression vector was transformed into a BL21 [DE3] *E. coli* host. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., 6-aminohexanol to 6-oxohexanol) were performed in a buffer composed of a final concentration of 50 mM HEPES buffer (pH=7.5), 10 mM 6-aminohexanol, 10 mM pyruvate, and 100 μM pyridoxyl 5' phosphate. Each enzyme activity assay reaction was initiated by adding cell free extract of the ω-transaminase gene product or the empty vector control to the assay buffer containing the 6-aminohexanol and then incubated at 25° C. for 4 h, with shaking at 250 rpm. The formation of L-alanine was quantified via RP-HPLC.

Each enzyme only control without 6-aminohexanol had low base line conversion of pyruvate to L-alanine See FIG. 16.

Figure 21:
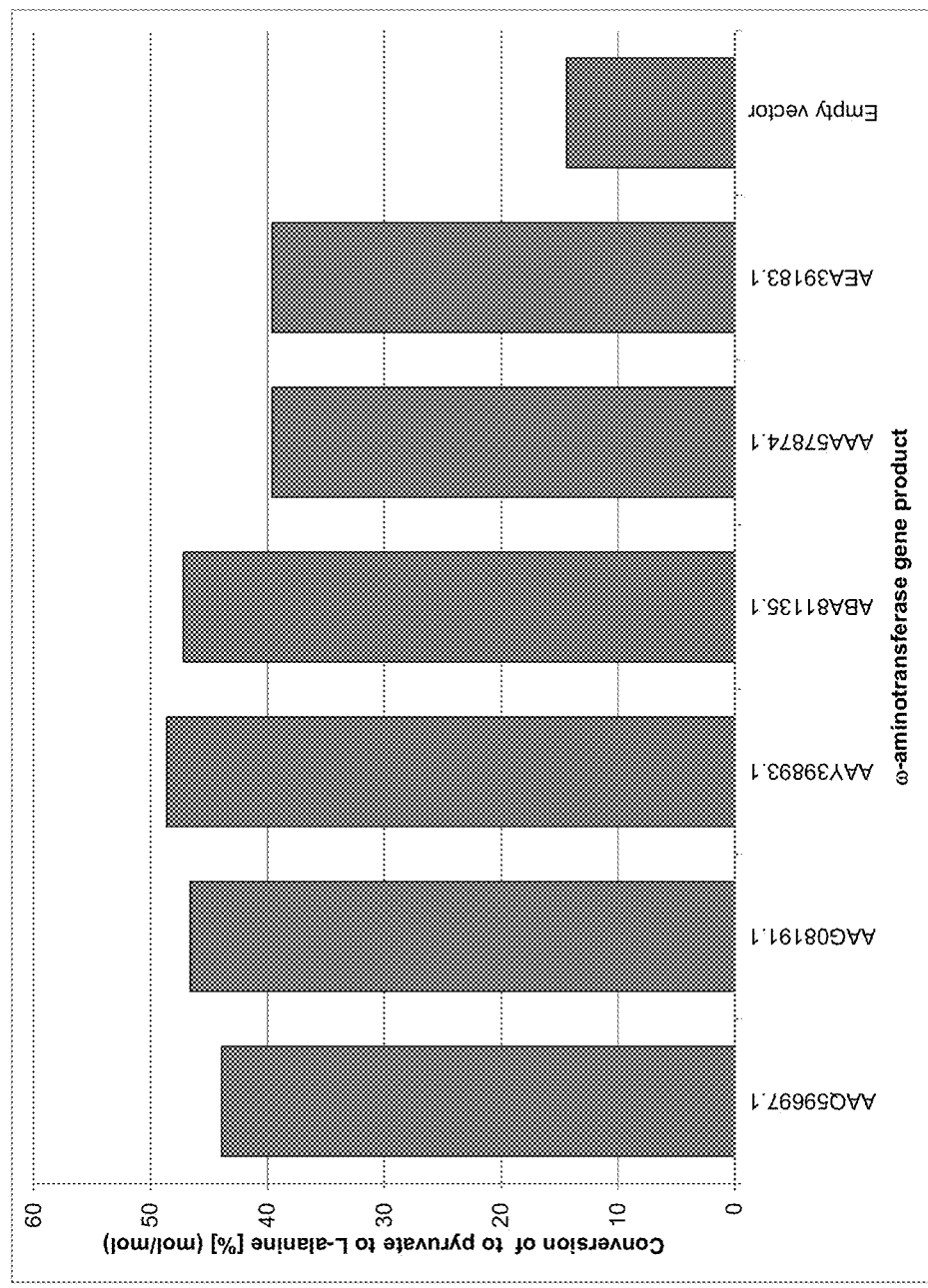
FIG. 21 is a bar graph of the percent conversion after 4 hours of pyruvate to L-alanine (mol/mol) as a measure of the ω-transaminase activity for converting 6-aminohexanol to 6-oxohexanol relative to the empty vector control.

The gene products of SEQ ID NOs: 7-12 accepted 6-aminohexanol as substrate as confirmed against the empty vector control (see FIG. 21) and synthesized 6-oxohexanol as reaction product. Given the reversibility of the ω-transaminase activity (see Example 5), it can be concluded that the gene products of SEQ ID NOs: 7-12 accept 6-aminohexanol as substrate and form 6-oxohexanol.

Example 9

Enzyme Activity of ω-Transaminase Using Hexamethylenediamine as Substrate and Forming 6-Aminohexanal A nucleotide sequence encoding an N-terminal His-tag was added to the *Chromobacterium violaceum, Pseudomonas aeruginosa, Pseudomonas syringae, Rhodobacter sphaeroides, Escherichia coli*, and *Vibrio fluvialis* genes encoding the w-transaminases of SEQ ID NOs: 7-12, respectively (see FIG. 9) such that N-terminal HIS tagged ω-transaminases could be produced. The modified genes were cloned into a pET21a expression vector under the T7 promoter. Each expression vector was transformed into a BL21 [DE3] *E. coli* host. Each resulting recombinant *E. coli* strain were cultivated at 37° C. in a 250 mL shake flask culture containing 50 mL LB media and antibiotic selection pressure, with shaking at 230 rpm. Each culture was induced overnight at 16° C. using 1 mM IPTG.

The pellet from each induced shake flask culture was harvested via centrifugation. Each pellet was resuspended and lysed via sonication. The cell debris was separated from the supernatant via centrifugation and the cell free extract was used immediately in enzyme activity assays.

Enzyme activity assays in the reverse direction (i.e., hexamethylenediamine to 6-aminohexanal) were performed in a buffer composed of a final concentration of 50 mM HEPES buffer (pH=7.5), 10 mM hexamethylenediamine, 10 mM pyruvate, and 100 μM pyridoxyl 5' phosphate. Each enzyme activity assay reaction was initiated by adding cell free extract of the ω-transaminase gene product or the empty vector control to the assay buffer containing the hexamethylenediamine and then incubated at 25° C. for 4 h, with shaking at 250 rpm. The formation of L-alanine was quantified via RP-HPLC.

Each enzyme only control without hexamethylenediamine had low base line conversion of pyruvate to L-alanine See FIG. 16.

Figure 19:
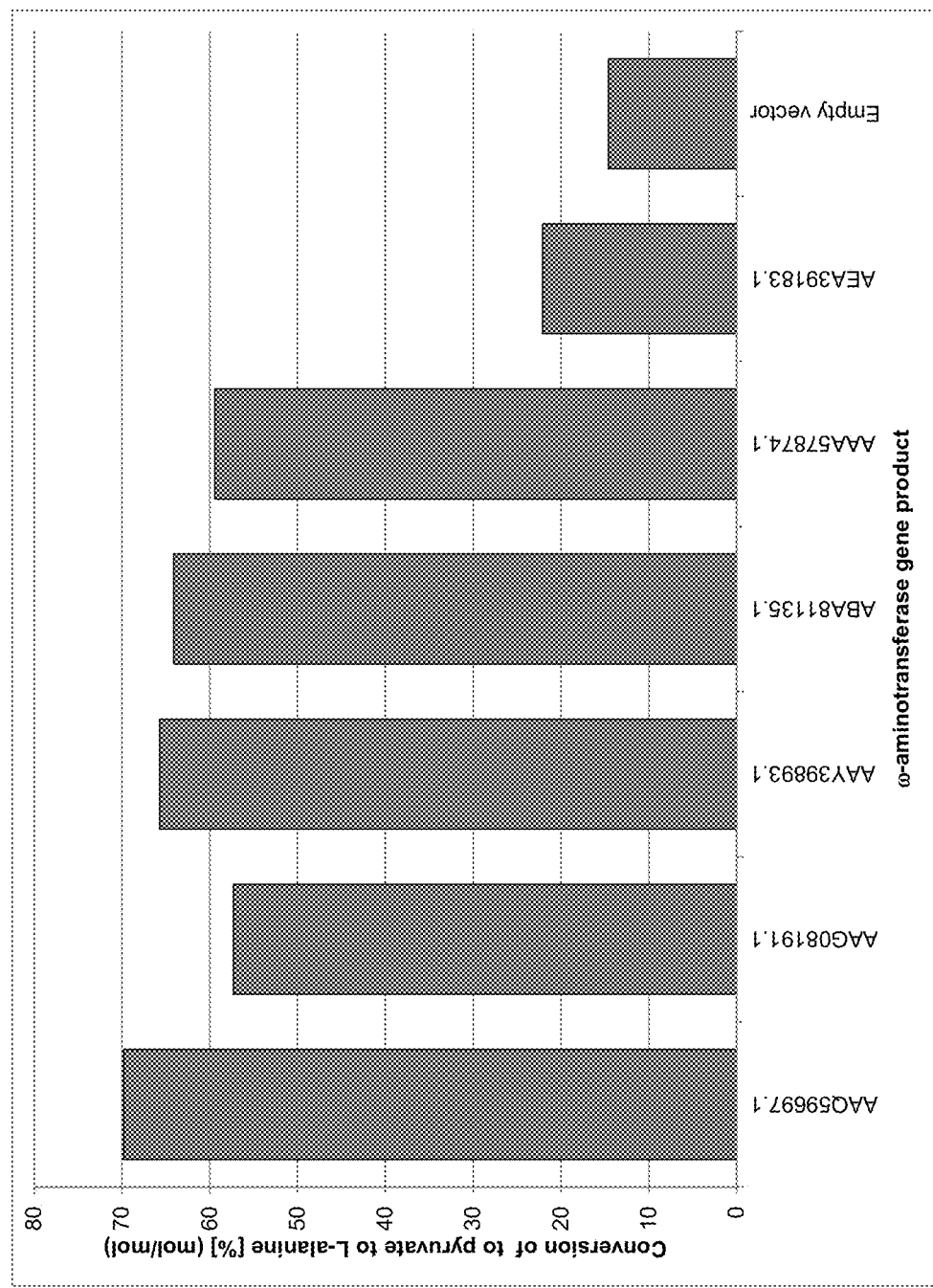
FIG. 19 is a bar graph of the percent conversion after 4 hours of pyruvate to L-alanine (mol/mol) as a measure of the ω-transaminase activity for converting hexamethylenediamine to 6-aminohexanal relative to the empty vector control.

The gene products of SEQ ID NO 7-12 accepted hexamethylenediamine as substrate as confirmed against the empty vector control (see FIG. 19) and synthesized 6-aminohexanal as reaction product. Given the reversibility of the ω-transaminase activity (see Example 5), it can be concluded that the gene products of SEQ ID NOs: 7-12 accept 6-aminohexanal as substrate and form hexamethylenediamine.

Example 10

Enzyme Activity of Carboxylate Reductase for N6-Acetyl-6-Aminohexanoate, Forming N6-Acetyl-6-Aminohexanal The activity of each of the N-terminal His-tagged carboxylate reductases of SEQ ID NOs: 4-6 (see Example 7, and FIG. 9) for converting N6-acetyl-6-aminohexanoate to N6-acetyl-6-aminohexanal was assayed in triplicate in a buffer composed of a final concentration of 50 mM HEPES buffer (pH=7.5), 2 mM N6-acetyl-6-aminohexanoate, 10 mM $MgCl_2$, 1 mM ATP, and 1 mM NADPH. The assays were initiated by adding purified carboxylate reductase and phosphopantetheine transferase or the empty vector control to the assay buffer containing the N6-acetyl-6-aminohexanoate then incubated at room temperature for 20 min. The consumption of NADPH was monitored by absorbance at 340 nm. Each enzyme only control without N6-acetyl-6-aminohexanoate demonstrated low base line consumption of NADPH. See FIG. 11.

Figure 14:
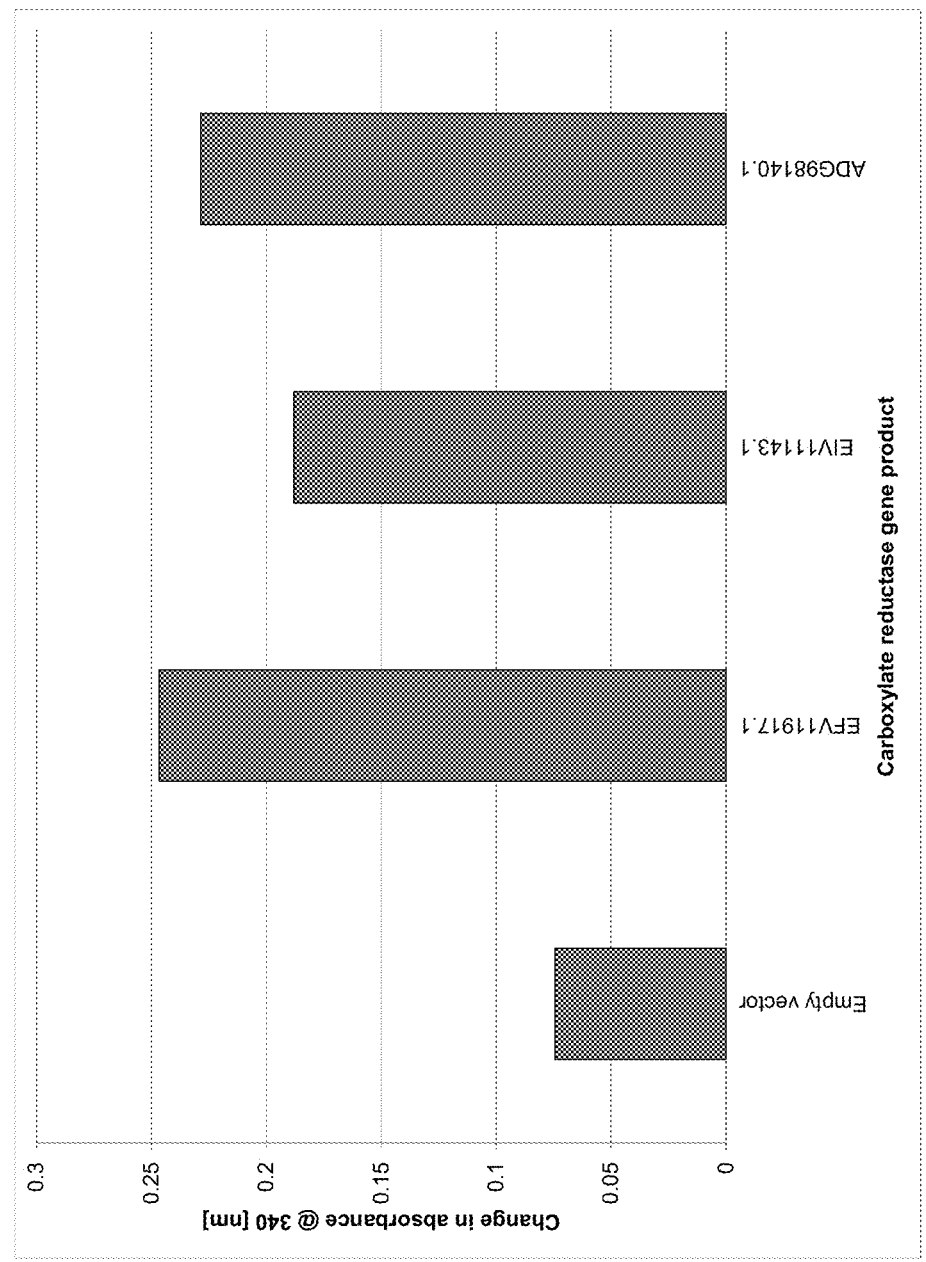
FIG. 14 is a bar graph of the change in absorbance at 340 nm after 20 minutes, which is a measure of the consumption of NADPH and the activity of carboxylate reductases for converting N6-acetyl-6-aminohexanoate to N6-acetyl-6-aminohexanal relative to the empty vector control.

The gene products of SEQ ID NO 4-6, enhanced by the gene product of sfp, accepted N6-acetyl-6-aminohexanoate as substrate as confirmed against the empty vector control (see FIG. 14), and synthesized N6-acetyl-6-aminohexanal.

Example 11

Enzyme Activity of ω-Transaminase Using N6-Acetyl-1,6-Diaminohexane, and Forming N6-Acetyl-6-Aminohexanal The activity of the N-terminal His-tagged ω-transaminases of SEQ ID NOs: 7-12 (see Example 9, and FIG. 9) for converting N6-acetyl-1,6-diaminohexane to N6-acetyl-6-aminohexanal was assayed using a buffer composed of a final concentration of 50 mM HEPES buffer (pH=7.5), 10 mM N6-acetyl-1,6-diaminohexane, 10 mM pyruvate and 100 μM pyridoxyl 5' phosphate. Each enzyme activity assay reaction was initiated by adding a cell free extract of the ω-transaminase or the empty vector control to the assay buffer containing the N6-acetyl-1,6-diaminohexane then incubated at 25° C. for 4 h, with shaking at 250 rpm. The formation of L-alanine was quantified via RP-HPLC.

Each enzyme only control without N6-acetyl-1,6-diaminohexane demonstrated low base line conversion of pyruvate to L-alanine See FIG. 16.

Figure 20:
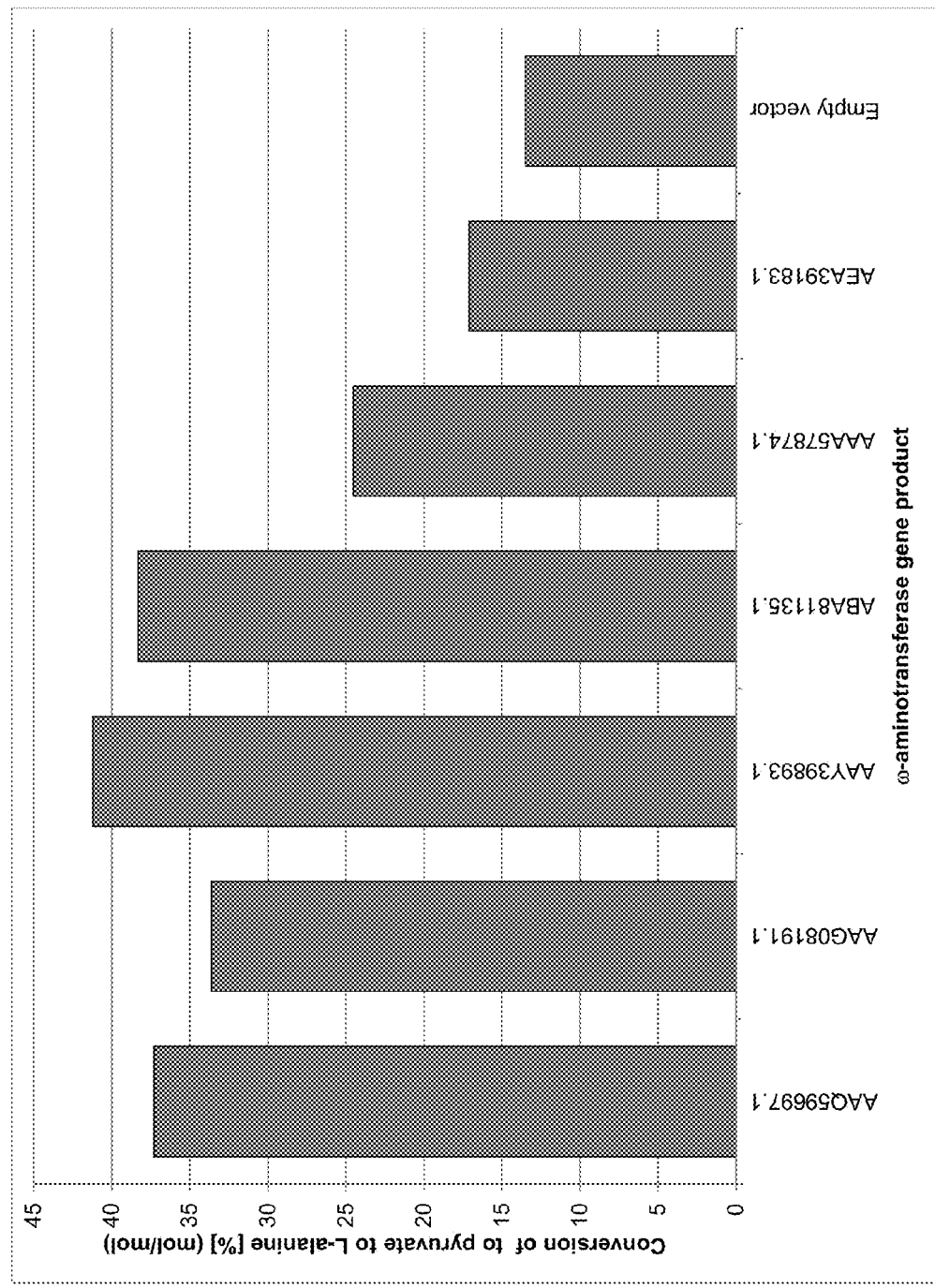
FIG. 20 is a bar graph of the percent conversion after 4 hours of pyruvate to L-alanine (mol/mol) as a measure of the ω-transaminase activity for converting N6-acetyl-1,6-diaminohexane to N6-acetyl-6-aminohexanal relative to the empty vector control.

The gene product of SEQ ID NO 7-12 accepted N6-acetyl-1,6-diaminohexane as substrate as confirmed against the empty vector control (see FIG. 20) and synthesized N6-acetyl-6-aminohexanal as reaction product.

Given the reversibility of the ω-transaminase activity (see example 5), the gene products of SEQ ID NOs: 7-12 accept N6-acetyl-6-aminohexanal as substrate forming N6-acetyl-1, 6-diaminohexane.

Example 12

Enzyme Activity of Carboxylate Reductase Using Adipate Semialdehyde as Substrate and Forming Hexanedial The N-terminal His-tagged carboxylate reductase of SEQ ID NO 6 (see Example 7 and FIG. 9) was assayed using adipate semialdehyde as substrate. The enzyme activity assay was performed in triplicate in a buffer composed of a final concentration of 50 mM HEPES buffer (pH=7.5), 2 mM adipate semialdehyde, 10 mM $MgCl_2$, 1 mM ATP and 1 mM NADPH. The enzyme activity assay reaction was initiated by adding purified carboxylate reductase and phosphopantetheine transferase or the empty vector control to the assay buffer containing the adipate semialdehyde and then incubated at room temperature for 20 min. The consumption of NADPH was monitored by absorbance at 340 nm. The enzyme only control without adipate semialdehyde demonstrated low base line consumption of NADPH. See FIG. 11.

Figure 15:
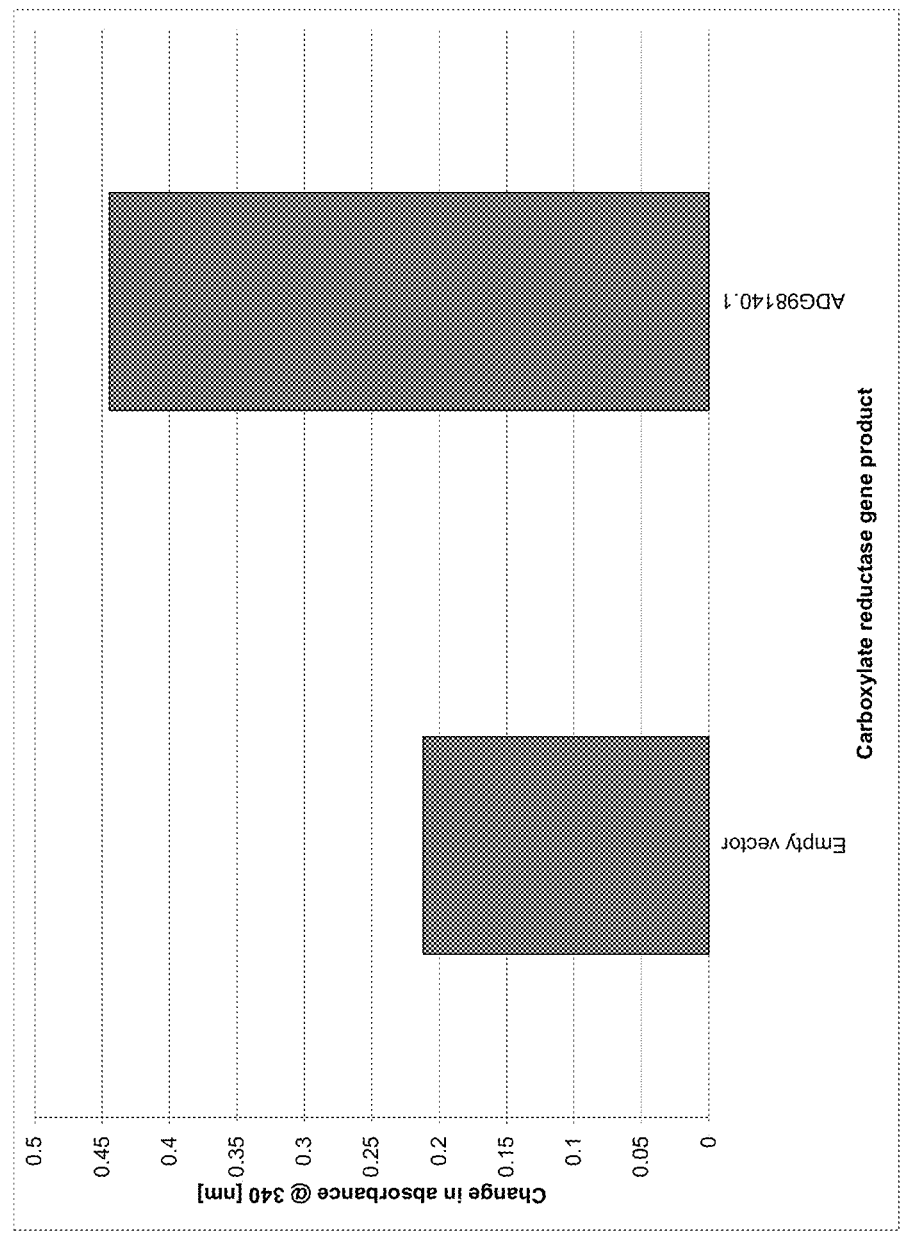
FIG. 15 is a bar graph of the change in absorbance at 340 nm after 20 minutes, which is a measure of the consumption of NADPH and activity of carboxylate reductases for converting adipate semialdehyde to hexanedial relative to the empty vector control.

The gene product of SEQ ID NO: 6, enhanced by the gene product of sfp, accepted adipate semialdehyde as substrate as confirmed against the empty vector control (see FIG. 15) and synthesized hexanedial.

Example 13

Enzyme Activity of CYP153 Monooxygenase Using Hexanoate as Substrate in Forming 6-Hydroxyhexanoate A sequence encoding a HIS tag was added to the *Polaromonas* sp. JS666, *Mycobacterium* sp. HXN-1500 and *Mycobacterium austroafricanum* genes respectively encoding (1) the monooxygenases (SEQ ID NOs: 13-15), (2) the associated ferredoxin reductase partner (SEQ ID NOs: 16-17) and the specie's ferredoxin (SEQ ID NOs: 18-19). For the *Mycobacterium austroafricanum* monooxygenase, *Mycobacterium* sp. HXN-1500 oxidoreductase and ferredoxin partners were used. The three modified protein partners were cloned into a pgBlue expression vector under a hybrid pTac promoter. Each expression vector was transformed into a BL21[DE3] *E. coli* host. Each resulting recombinant *E. coli* strain were cultivated at 37° C. in a 500 mL shake flask culture containing 50 mL LB media and antibiotic selection pressure. Each culture was induced for 24 h at 28° C. using 1 mM IPTG.

The pellet from each induced shake flask culture was harvested via centrifugation. Each pellet was resuspended and the cells made permeable using Y-per™ solution (Thermo-Scientific, Rockford, Ill.) at room temperature for 20 min. The permeabilized cells were held at 0° C. in the Y-per™ solution.

Enzyme activity assays were performed in a buffer composed of a final concentration of 25 mM potassium phosphate buffer (pH=7.8), 1.7 mM $MgSO_4$, 2.5 mM NADPH and 30 mM hexanoate. Each enzyme activity assay reaction was initiated by adding a fixed mass of wet cell weight of permeabilized cells suspended in the Y-per™ solution to the assay buffer containing the heptanoate and then incubated at 28° C. for 24 h, with shaking at 1400 rpm in a heating block shaker. The formation of 7-hydroxyheptanoate was quantified via LC-MS.

Figure 22:
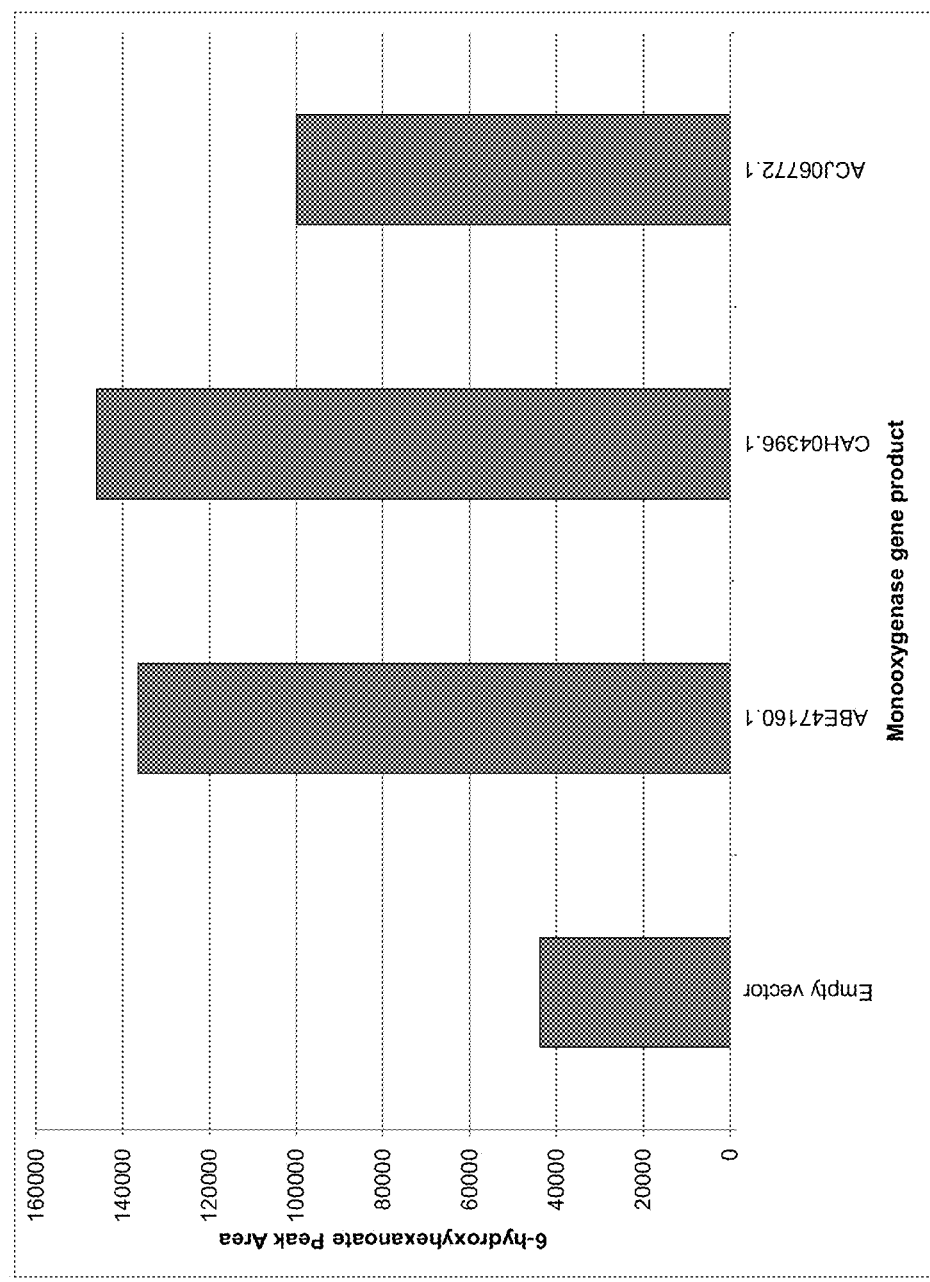
FIG. 22 is a bar graph of the change in peak area for 6-hydroxyhexanoate as determined via LC-MS, as a measure of the monooxygenase activity for converting hexanoate to 6-hydroxyhexanoate relative to the empty vector control.

The monooxygenase gene products of SEQ ID NO 13-15 along with reductase and ferredoxin partners, accepted hexanoate as substrate as confirmed against the empty vector control (see FIG. 22) and synthesized 6-hydroxyhexanoate as reaction product.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for biosynthesizing one or more products selected from the group consisting of adipic acid, 6-aminohexanoic acid, 6-hydroxyhexanoic acid, hexamethylenediamine, caprolactam, and 1,6-hexanediol, said method comprising enzymatically synthesizing hexanoyl-CoA and enzymatically forming, in one or more steps, two terminal functional groups selected from the group consisting of carboxyl, amine, and hydroxyl groups in hexanoyl-CoA to produce the one or more products.

2. The method of claim 1, wherein said hexanoyl-CoA is produced from acetyl-CoA in two cycles of CoA-dependent carbon chain elongation using (i) either a β-ketothiolase or an acetyl-CoA carboxylase and an acetoacetyl-CoA synthase, (ii) a 3-hydroxyacyl-CoA dehydrogenase or a 3-oxoacyl-CoA reductase, (iii) an enoyl-CoA hydratase, (iv) and a trans-2-enoyl-CoA reductase.

3. The method of claim 1, wherein said two terminal functional groups are the same or said two terminal functional groups are different.

4. The method of claim 3, wherein said product comprises a terminal amine group and a terminal carboxyl group or a terminal hydroxyl group and a terminal carboxyl group.

5. The method of claim 3, wherein said two terminal functional groups are amine groups or said two terminal functional groups are hydroxyl groups.

6. The method of claim 5, wherein a ω-transaminase or a deacetylase enzymatically forms the two amine groups.

7. The method of claim 5, wherein a monooxygenase, an oxidoreductase and ferredoxin or an alcohol dehydrogenase enzymatically forms the two hydroxyl groups.

8. The method of claim 7, wherein said monooxygenase has at least 70% sequence identity to any one of the amino acid sequences set forth in SEQ ID NO. 13-15.

9. The method of claim 1, wherein a thioesterase, an aldehyde dehydrogenase, a 7-oxoheptanoate dehydrogenase, or a 6-oxohexanoate dehydrogenase, enzymatically forms a terminal carboxyl group.

10. The method of claim 9, wherein said thioesterase has at least 70% sequence identity to the amino acid sequence set forth in SEQ ID NO: 1.

11. The method of claim 4, wherein a ω-transaminase enzymatically forms the amine group.

12. The method of claim 11, wherein said ω-transaminase has at least 70% sequence identity to any one of the amino acid sequences set forth in SEQ ID NO. 7-12.

13. The method of claim 1, wherein a carboxylate reductase and a phosphopantetheinyl transferase form a terminal aldehyde group as an intermediate in forming the product.

14. The method of claim 13, wherein said carboxylate reductase has at least 70% sequence identity to any one of the amino acid sequences set forth in SEQ ID NO. 2-6.

15. The method of claim 1, wherein said method is performed in a recombinant host.

16. The method of claim 15, wherein the principal carbon source fed to the fermentation derives from biological or non-biological feedstocks.

17. The method of claim 16, wherein the biological feedstock is, or derives from, monosaccharides, disaccharides, lignocellulose, hemicellulose, cellulose, lignin, levulinic acid, formic acid, triglycerides, glycerol, fatty acids, agricultural waste, condensed distillers' solubles, or municipal waste; or wherein the non-biological feedstock is, or derives from, natural gas, syngas, $CO_2/H_2$, methanol, ethanol, benzoate, non-volatile residue (NVR) caustic wash waste stream from cyclohexane oxidation processes, or terephthalic acid/isophthalic acid mixture waste streams.

18. The method of claim 15, wherein the host is a prokaryote.

19. The method of claim 18, wherein said prokaryote is from the genus *Escherichia*; from the genus *Clostridia*; from the genus *Corynebacteria*; from the genus *Cupriavidus*; from the genus *Pseudomonas*; from the genus *Delftia*; from the genus *Bacillus*; from the genus *Lactobacillus*; from the genus *Lactococcus* or from the genus *Rhodococcus*.

20. The method of claim 15, wherein the host is a eukaryote.

21. The method of claim 20, wherein said eukaryote is from the genus *Aspergillus*; from the genus *Saccharomyces*; from the genus *Pichia*; from the genus *Yarrowia*; from the genus *Issatchenkia*; from the genus *Debaryomyces*; from the genus *Arxula*; or from the genus *Kluyveromyces*.

22. The method of claim 15, wherein said host comprises one or more of the following attenuated enzymes: polyhydroxyalkanoate synthase, an acetyl-CoA thioesterase, a phosphotransacetylase forming acetate, an acetate kinase, a lactate dehydrogenase, a menaquinol-fumarate oxidoreductase, a 2-oxoacid decarboxylase producing isobutanol, an alcohol dehydrogenase forming ethanol, a triose phosphate isomerase, a pyruvate decarboxylase, a glucose-6-phosphate isomerase, NADH-consuming transhydrogenase, an NADH-specific glutamate dehydrogenase, a NADH/NADPH-utilizing glutamate dehydrogenase, a pimeloyl-CoA dehydrogenase; an acyl-CoA dehydrogenase accepting C6 building blocks and central precursors as substrates; a butaryl-CoA dehydrogenase; or an adipyl-CoA synthetase.

23. The method of claim 15, wherein said host overexpresses one or more genes encoding: an acetyl-CoA synthetase, a 6-phosphogluconate dehydrogenase; a transketolase; a puridine nucleotide transhydrogenase; a glyceraldehyde-3P-dehydrogenase; a malic enzyme; a glucose-6-phosphate dehydrogenase; a glucose dehydrogenase; a fructose 1,6 diphosphatase; a L-alanine dehydrogenase; a L-glutamate dehydrogenase; a formate dehydrogenase; a L-glutamine synthetase; a diamine transporter; a dicarboxylate transporter; and/or a multidrug transporter.

24. The method of claim 4, wherein a ω-transaminase enzymatically forms the amine group.

25. The method of claim 19, wherein said prokaryote is selected from the group consisting of *Escherichia coli, Clostridium ljungdahlii, Clostridium autoethanogenum, Clostridium kluyveri, Corynebacterium glutamicum, Cupriavidus necator, Cupriavidus metallidurans, Pseudomonas fluorescens, Pseudomonas putida, Pseudomonas oleavorans, Delftia acidovorans, Bacillus subtillis, Lactobacillus delbrueckii, Lactococcus lactis*, and *Rhodococcus equi*.

26. The method of claim 21, wherein said eukaryote is selected from the group consisting of *Aspergillus niger, Saccharomyces cerevisiae, Pichia pastoris, Yarrowia lipolytica, Issathenkia orientalis, Debaryomyces hansenii, Arxula adenoinivorans*, and *Kluyveromyces lactis*.

* * * * *

UNITED STATES PATENT AND TRADEMARK OFFICE
CERTIFICATE OF CORRECTION

PATENT NO.        : 9,102,960 B2                                Page 1 of 1
APPLICATION NO.   : 14/106124
DATED             : August 11, 2015
INVENTOR(S)       : Adriana Leonora Botes et al.

It is certified that error appears in the above-identified patent and that said Letters Patent is hereby corrected as shown below:

In the Claims:

Column 97, line 16, "(iv) and" should read as -- and (iv) --

Column 98, line 39, "puridine" should read as -- pyridine --

Signed and Sealed this
Tenth Day of May, 2016

Michelle K. Lee
*Director of the United States Patent and Trademark Office*